(12) United States Patent
Schraga

(10) Patent No.: US 9,480,799 B2
(45) Date of Patent: Nov. 1, 2016

(54) RETRACTABLE NEEDLE ASSEMBLY UTILIZING A STANDARD INTERFACE AND SYRINGE UTILIZING THE SAME

(75) Inventor: Steven Schraga, Surfside, FL (US)

(73) Assignee: STAT MEDICAL DEVICES, INC., North Miami Beach, FL (US)

(*) Notice: Subject to any disclaimer, the term of this patent is extended or adjusted under 35 U.S.C. 154(b) by 954 days.

(21) Appl. No.: 13/100,838

(22) Filed: May 4, 2011

(65) Prior Publication Data
US 2011/0213304 A1  Sep. 1, 2011

Related U.S. Application Data

(63) Continuation-in-part of application No. 12/752,186, filed on Apr. 1, 2010, now Pat. No. 8,986,249.

(60) Provisional application No. 61/167,741, filed on Apr. 8, 2009.

(51) Int. Cl.
| | | |
|---|---|---|
| A61M 5/00 | (2006.01) | |
| A61M 5/32 | (2006.01) | |
| A61M 5/315 | (2006.01) | |
| A61M 5/50 | (2006.01) | |
| A61M 5/31 | (2006.01) | |

(52) U.S. Cl.
CPC ............ *A61M 5/3234* (2013.01); *A61M 5/002* (2013.01); *A61M 5/31515* (2013.01); *A61M 5/502* (2013.01); *A61M 5/508* (2013.01); *A61M 2005/3123* (2013.01); *A61M 2005/3231* (2013.01); *A61M 2005/3235* (2013.01); *A61M 2005/3236* (2013.01); *A61M 2005/3239* (2013.01)

(58) Field of Classification Search
CPC .. A61M 5/3234; A61M 5/508; A61M 5/322; A61M 2005/3235; A61M 2005/3231; A61M 2005/3239; A61M 2005/5073; A61M 5/50
USPC .......................... 604/110, 194–196, 220, 225
See application file for complete search history.

(56) References Cited

U.S. PATENT DOCUMENTS

| | | | |
|---|---|---|---|
| 4,650,468 A | | 3/1987 | Jennings, Jr. |
| 4,929,238 A | | 5/1990 | Baum |
| 4,946,441 A | | 8/1990 | Laderoute et al. |
| 4,994,034 A | * | 2/1991 | Botich et al. ................. 604/110 |
| 5,002,533 A | | 3/1991 | Jullien |
| 5,019,044 A | | 5/1991 | Tsao |
| 5,049,133 A | * | 9/1991 | Pascual ......................... 604/110 |
| 5,053,010 A | | 10/1991 | McGary et al. |
| 5,098,402 A | | 3/1992 | Davis |
| 5,125,898 A | * | 6/1992 | Kaufhold et al. ............ 604/110 |
| 5,127,906 A | | 7/1992 | Landry et al. |

(Continued)

FOREIGN PATENT DOCUMENTS

| | | |
|---|---|---|
| EP | 2 251 054 | 11/2010 |
| GB | 2 266 667 | 11/1993 |
| KR | 10-2004-0101698 | 12/2004 |

*Primary Examiner* — Emily Schmidt
(74) *Attorney, Agent, or Firm* — Greenblum & Bernstein, P.L.C.

(57) ABSTRACT

An injection device including a barrel, a hollow plunger having a portion structured and arranged to move within the barrel, a needle unit, and a safety system that one of automatically causes the needle unit to retract into the plunger when the plunger reaches a substantially fully depressed position. This Abstract is not intended to define the invention disclosed in the specification, nor intended to limit the scope of the invention in any way.

15 Claims, 70 Drawing Sheets

(56) References Cited

U.S. PATENT DOCUMENTS

| | | |
|---|---|---|
| 5,167,635 A | 12/1992 | Haber et al. |
| 5,188,599 A | 2/1993 | Botich et al. |
| 5,188,600 A | 2/1993 | Jullien |
| 5,242,401 A | 9/1993 | Colsky |
| 5,267,977 A | 12/1993 | Feeney, Jr. |
| 5,308,329 A | 5/1994 | Mazur et al. |
| 5,328,475 A | 7/1994 | Chen |
| 5,336,198 A | 8/1994 | Silver et al. |
| 5,344,403 A | 9/1994 | Lee |
| 5,376,080 A | 12/1994 | Petrussa |
| 5,401,249 A | 3/1995 | Shields |
| 5,403,286 A | 4/1995 | Lockwood, Jr. |
| 5,498,241 A | 3/1996 | Fabozzi |
| 5,569,203 A | 10/1996 | Chen |
| 5,591,131 A | 1/1997 | Chen |
| 5,591,138 A | 1/1997 | Vaillancourt |
| 5,814,017 A | 9/1998 | Kashmer et al. |
| 5,858,000 A | 1/1999 | Novacek et al. |
| 6,010,486 A | 1/2000 | Carter et al. |
| 6,074,370 A | 6/2000 | Pressly, Sr. et al. |
| 6,074,373 A | 6/2000 | Sudo et al. |
| 6,083,199 A | 7/2000 | Thorley et al. |
| 6,179,812 B1 * | 1/2001 | Botich et al. .................. 604/110 |
| 6,183,440 B1 | 2/2001 | Bell |
| 6,210,371 B1 | 4/2001 | Shaw |
| D452,000 S | 12/2001 | Crawford et al. |
| 6,368,303 B1 | 4/2002 | Caizza |
| 6,375,640 B1 | 4/2002 | Teraoka |
| 6,461,328 B2 | 10/2002 | Wang et al. |
| 6,517,516 B1 | 2/2003 | Caizza |
| 6,632,198 B2 | 10/2003 | Caizza |
| 6,648,849 B2 | 11/2003 | Tenhuisen et al. |
| 6,840,291 B2 | 1/2005 | Caizza et al. |
| 7,090,656 B1 | 8/2006 | Botich et al. |
| 7,144,387 B2 | 12/2006 | Millerd |
| 7,150,725 B2 | 12/2006 | Wilkinson |
| 7,322,963 B2 | 1/2008 | Goh |
| 7,413,560 B2 | 8/2008 | Chong et al. |
| 7,428,773 B2 | 9/2008 | Newby et al. |
| 7,500,967 B2 | 3/2009 | Thorley et al. |
| 7,604,613 B2 | 10/2009 | Crawford et al. |
| 7,803,132 B2 | 9/2010 | Janek et al. |
| 7,846,135 B2 | 12/2010 | Runfola |
| 7,935,087 B2 | 5/2011 | Judd et al. |
| 8,002,745 B2 | 8/2011 | Kaal et al. |
| 8,012,132 B2 | 9/2011 | Lum et al. |
| 8,021,333 B2 | 9/2011 | Kaal et al. |
| 8,052,654 B2 | 11/2011 | Kaal et al. |
| 8,114,050 B2 | 2/2012 | Kaal et al. |
| 8,147,450 B2 | 4/2012 | Yang |
| 2003/0004491 A1 * | 1/2003 | Tenhuisen et al. .......... 604/502 |
| 2004/0254529 A1 | 12/2004 | Fitzgerald |
| 2005/0159705 A1 * | 7/2005 | Crawford et al. ........... 604/110 |
| 2006/0084913 A1 | 4/2006 | Lo |
| 2008/0154212 A1 | 6/2008 | Schraga |
| 2010/0262119 A1 | 10/2010 | Schraga |
| 2011/0125130 A1 | 5/2011 | Schraga |
| 2011/0213304 A1 | 9/2011 | Schraga |

* cited by examiner

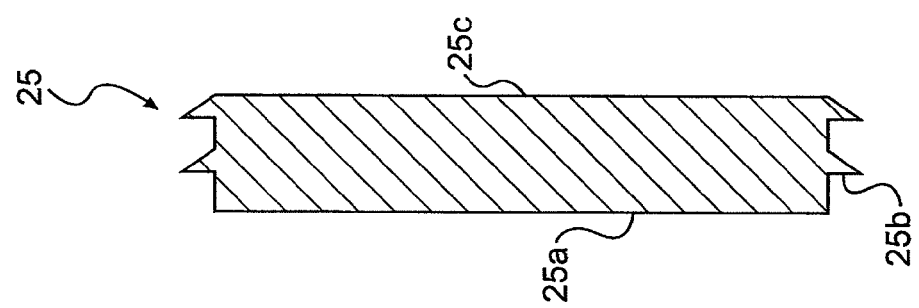
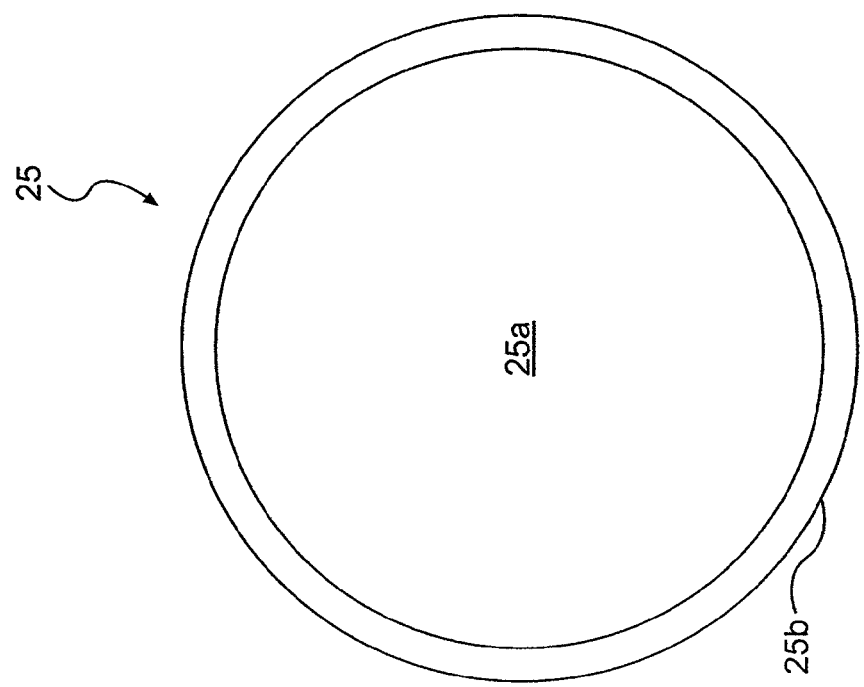
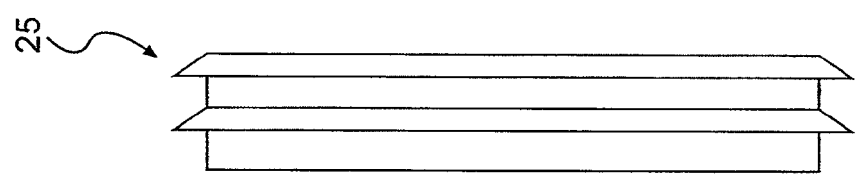
FIG. 14
FIG. 13
FIG. 12

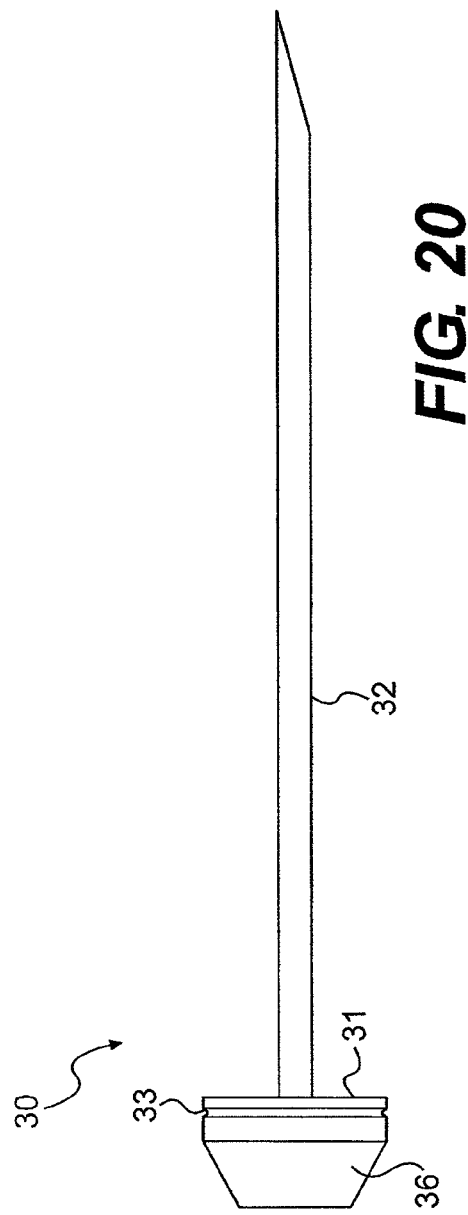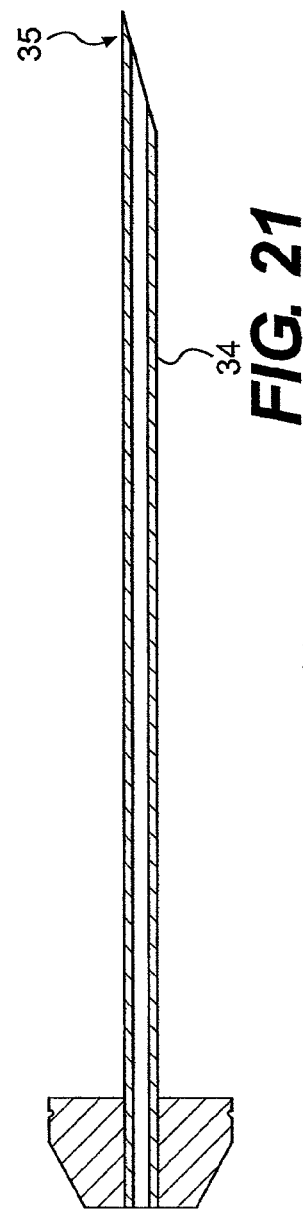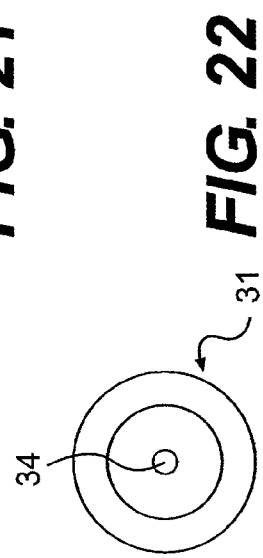

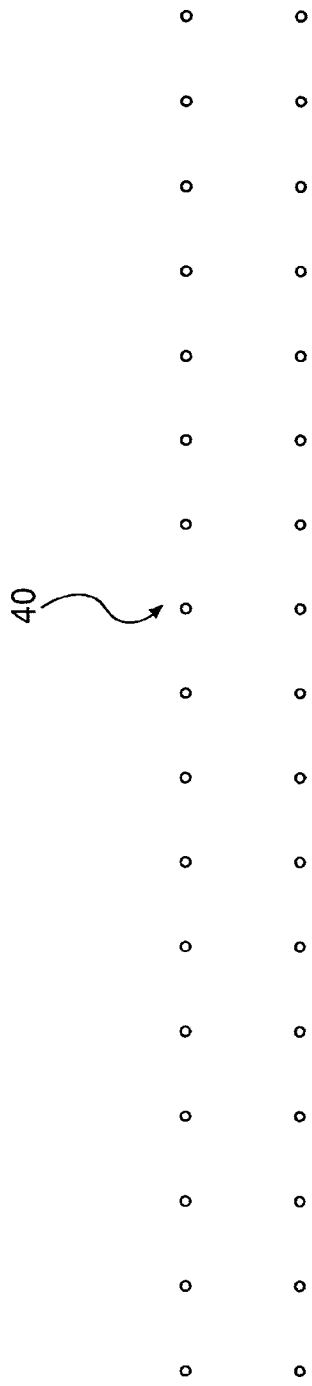

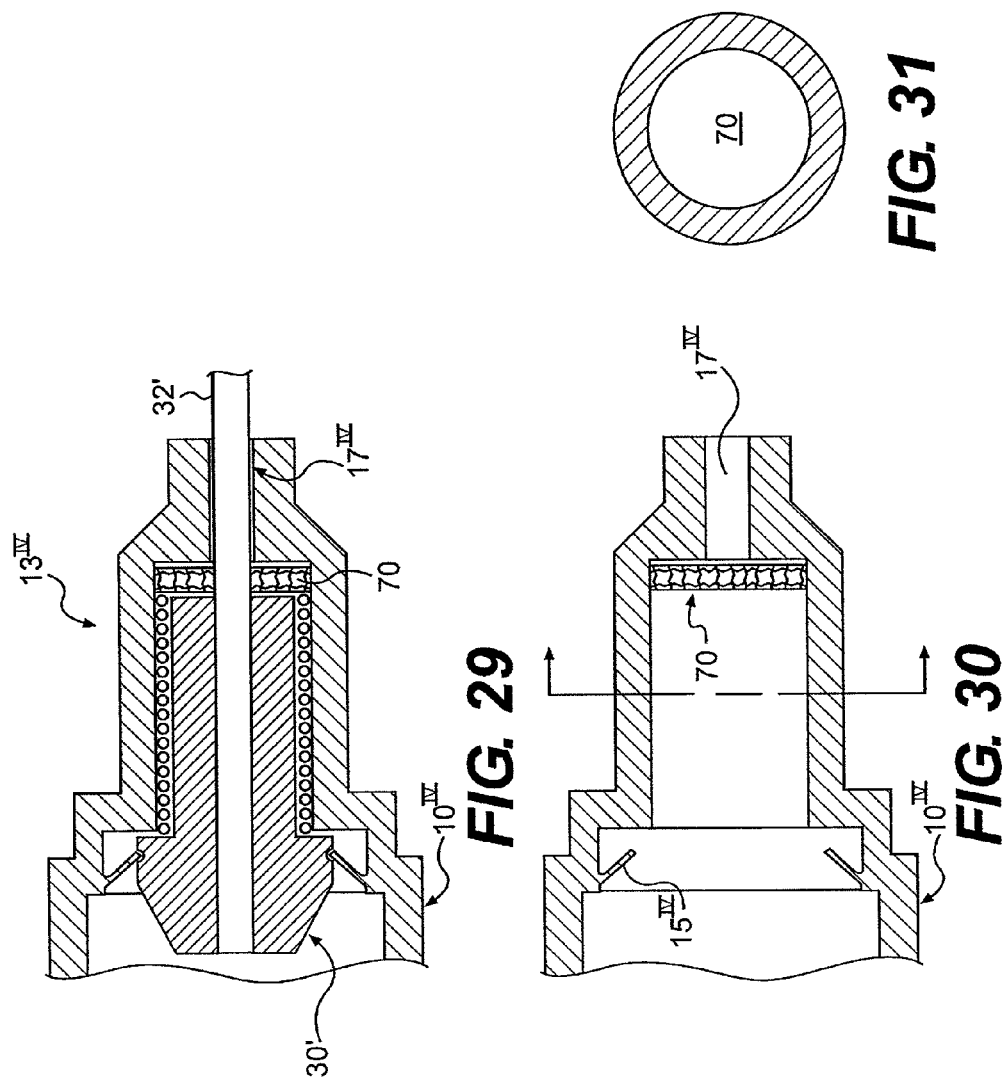

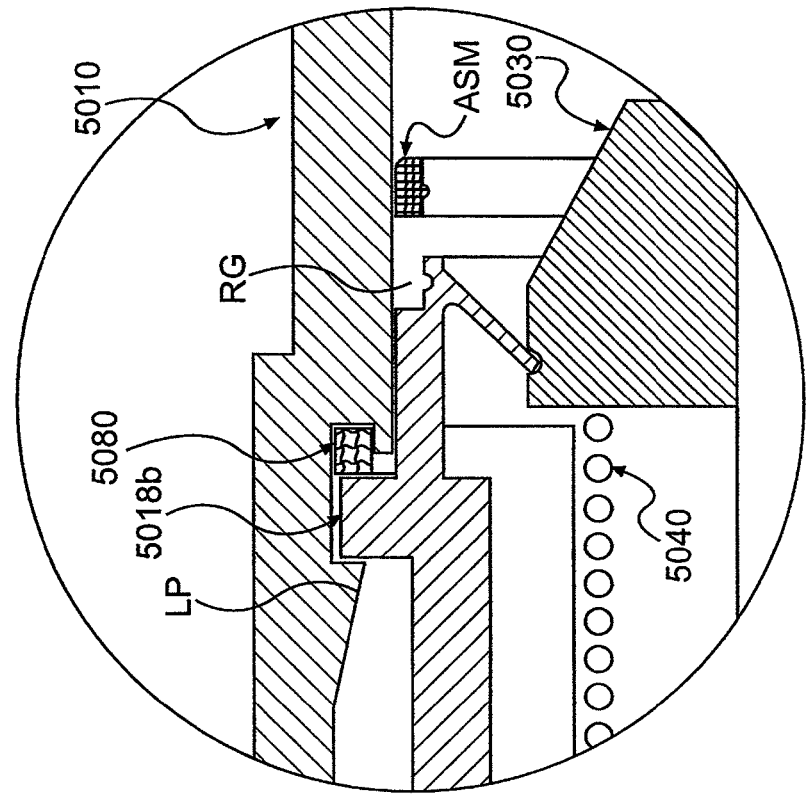
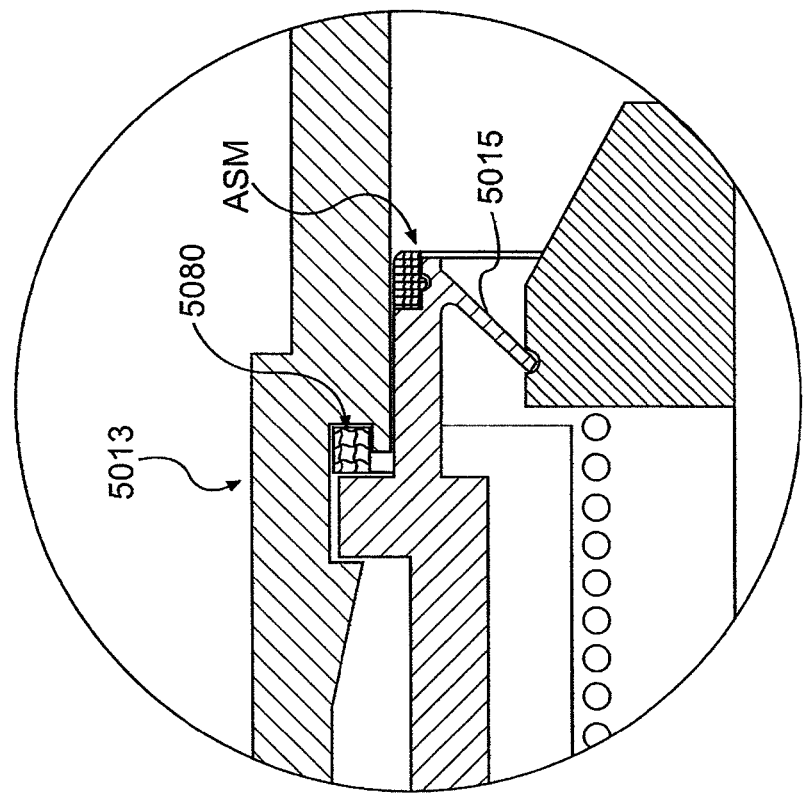

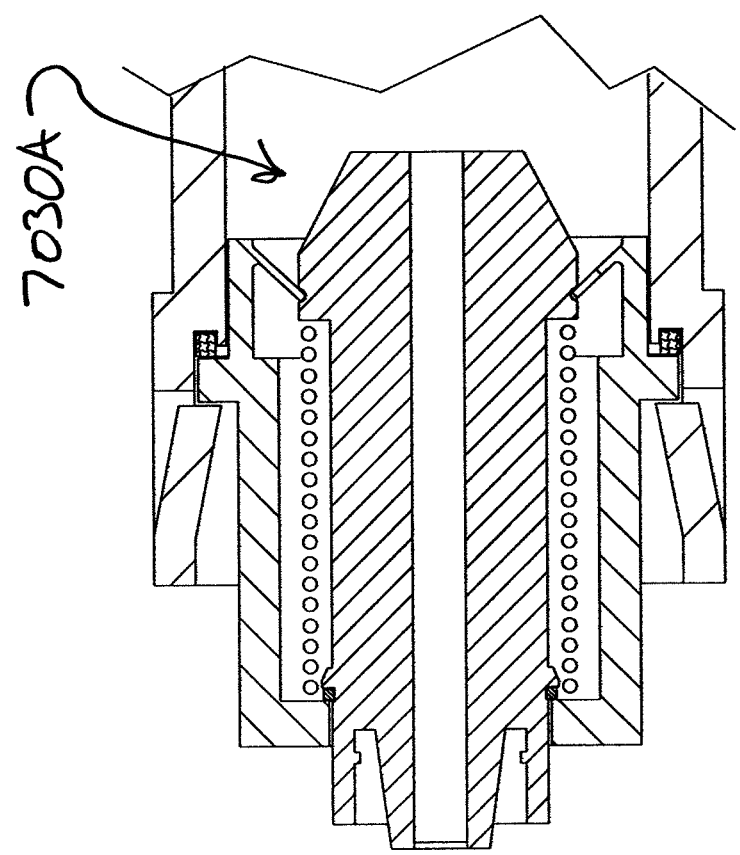
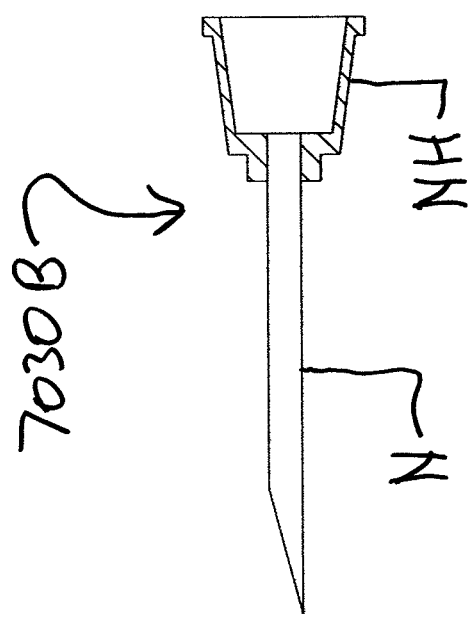
FIG. 66

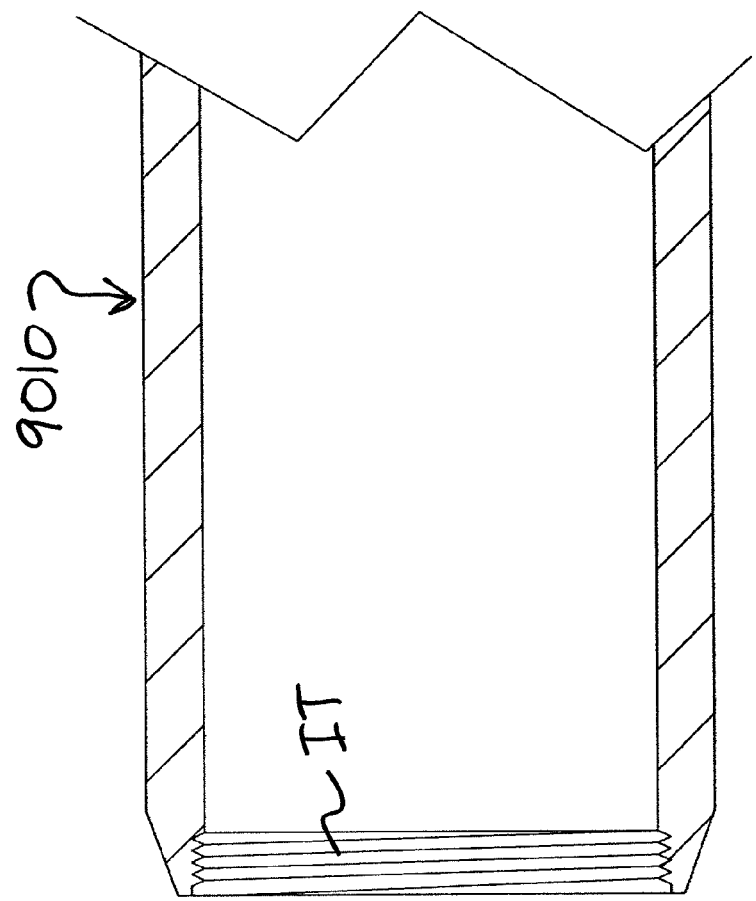
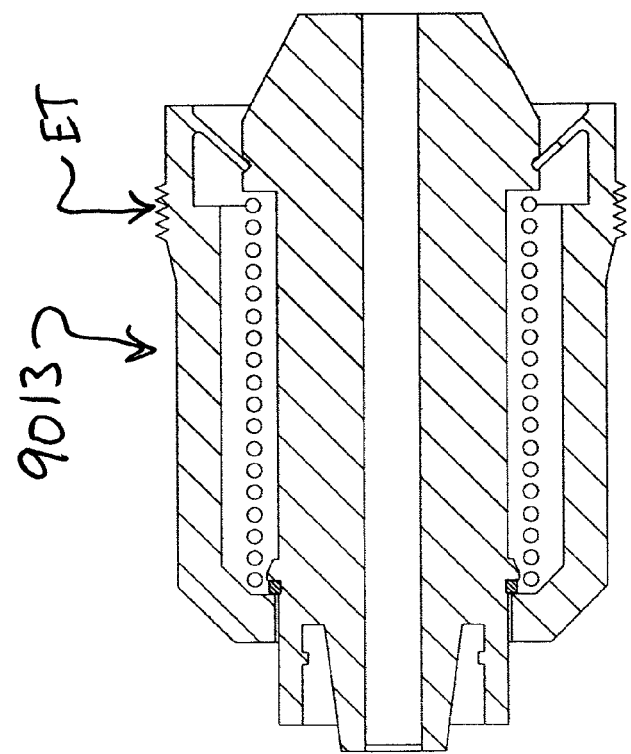
FIG. 80

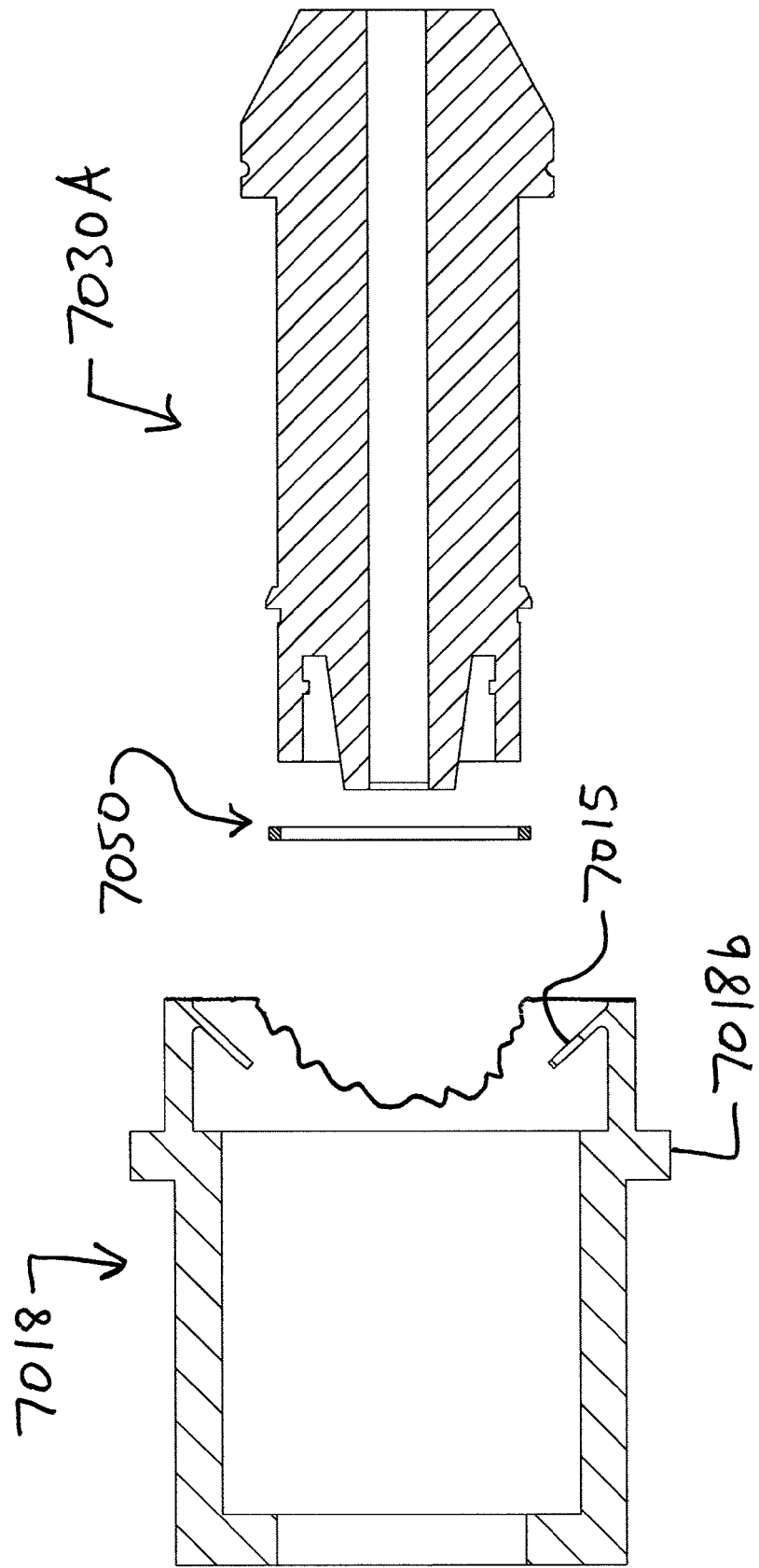

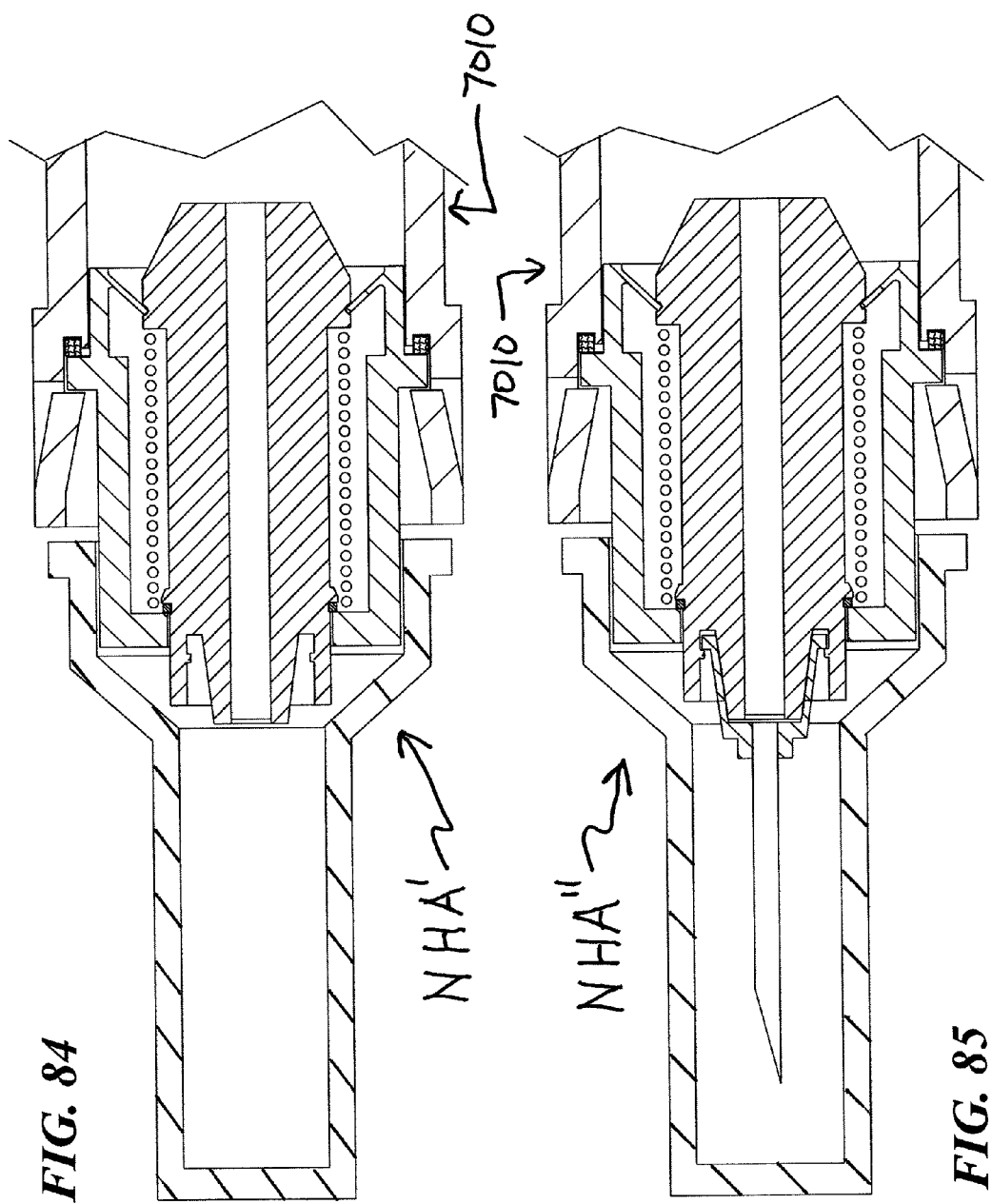

RETRACTABLE NEEDLE ASSEMBLY UTILIZING A STANDARD INTERFACE AND SYRINGE UTILIZING THE SAME

CROSS-REFERENCE TO RELATED APPLICATIONS

The instant application is a Continuation-in-part (CIP) application of U.S. application Ser. No. 12/752,186 filed Apr. 1, 2010, which is a US non-provisional application based on U.S. provisional application No. 61/167,741, filed Apr. 8, 2009. The disclosure of each of these applications is hereby expressly incorporated by reference in their entireties.

BACKGROUND OF THE INVENTION

1. Field of the Invention

This invention relates generally to syringes, e.g., hypodermic syringes, such are utilized for injection of medicament into the body tissues of human and animal patients. More specifically, this invention relates to a hypodermic syringe having a plunger, piston and needle support structure or needle unit that permits retraction of the needle support and its needle into the plunger of the syringe to prevent the possibility of inadvertent needle pricks and which incorporates a frangible plunger seal that may be broken or separated away to prevent subsequent use or re-use of the syringe.

This invention also relates to single-use syringes which automatically retracts a standard interface needle into the syringe when the plunger is substantially fully depressed which is more easily and/or less costly to produce.

This invention also relates to syringes which can be used only once, i.e., single-use syringes, and/or to syringes which utilize a built-in safety system which cannot be easily overridden by a user thereof.

This invention also relates to syringes which utilize one or more features disclosed in U.S. Ser. No. 12/951,925 filed on Nov. 22, 2010 or in combination with one or more features disclosed herein.

2. Discussion of Background Information

In hospitals, nursing home facilities and the like, injection of medicament into the body tissues of patients is done on a daily basis. Typical hypodermic syringes are provided with a barrel having a needle that is fixed or removably attached at one end thereof. A plunger typically having an elastomeric piston is movable within the barrel to load the barrel with liquid medicament by suction as the plunger and piston are moved within the barrel in a direction away from the needle. After the needle has penetrated the body tissues of the patient, as the direction of movement of the plunger and piston are reversed and the piston is forced toward the needle, medicament contained within the barrel will be injected through the needle into the body tissues.

After hypodermic syringes have been used in this manner, those syringes that are disposable present a significant problem to users, e.g., hospital or nursing home staff, because the possibility of inadvertent needle pricks subject personnel to the possibility of cross-contamination by, among other things, virile or bacterial contaminants that might be present on the needle after its use. In an effort to avoid the possibility of inadvertent needle pricks special waste containers are often provided at hospital facilities into which the used disposable hypodermic syringes are placed. These containers and the syringes contained therein are then disposed of in a specifically organized manner to insure against the possibility of inadvertent infectious contamination of nursing personnel. Further, refuse handlers and other persons who might inadvertently come into contact with the used hypodermic syringes are also subject to the same hazards. Often times the needles themselves are bent over so as to minimize the possibility of inadvertent needle pricks and to preclude the possibility of subsequent use of disposable hypodermic syringes.

In certain situations, medicaments are injected into patients and not quickly thereafter discarded properly. Instead, the used syringe is placed in a temporary position. After the procedure has ended, the syringe can be manually recovered for disposal. However, between the time of use and the time of disposal, there is the possibility that inadvertent needle pricks will occur. Accordingly, it is desirable to provide a suitable way protecting personnel, e.g., nursing personnel, paramedics and other persons, from the hazards of inadvertent needle pricks as they go about their daily tasks.

It is therefore desirable to provide a syringe that includes a system for rendering the needle thereof to a protected, completely encapsulated condition such that it is less likely to cause, after use, an inadvertent needle prick during its handling or during its disposal. It is also desirable to provide a syringe having the capability of causing the automatic retraction of the needle to a position inside the plunger of the syringe and maintaining the needle in its retracted position so that the needle of the syringe is always enclosed after its use, thus precluding the possibility that the needle might cause an accidental needle prick as the syringe is subsequently handled. It is also desirable to provide a syringe of the disposable type that is provided with facility for rendering it completely inoperative such that it can not be subsequently used. Additionally, it is desirable to provide for a syringe which also has minimal dead-space so that it can be ideally used for injecting very expensive medicaments with minimal waste. Finally, it is desirable to provide for a syringe which also has a system for selectively locking the plunger in a substantially fully depressed position so that the syringe can have dual, multiple, and/or parallel safety systems, i.e., one system can include causing the needle unit to retract into the plunger and another system can include locking the plunger in a substantially fully depressed position.

SUMMARY OF THE INVENTION

According to one non-limiting aspect of the invention there is provided a single-use injection device comprising a barrel, a plunger having a portion structured and arranged to move within the barrel, a needle connecting arrangement that one of: comprises a needle connecting interface adapted to mate with a needle interface and an end integrally formed with the barrel; comprises a spring biased needle connecting member having an interface adapted to mate with a needle interface and being movable from an initial position to a retracted position within the barrel; comprises a needle connecting interface adapted to mate with a needle interface and an end that can be non-removably connected with the barrel; comprises a luer-lock interface which can retract into the barrel when the plunger is substantially fully depressed; comprises a movable member which includes a standard interface and which can retract into the barrel when the plunger is substantially fully depressed; comprises a movable member which includes a standard interface and which can retract into the plunger; comprises a movable member which includes an interface to which a needle member can be removably connected and which can retract into the barrel by a spring upon a movement of the plunger; comprises a body connectable to one end of the barrel and a movable member which includes an interface to which a needle member can be connected and which can retract into the barrel by a spring upon a movement of the plunger; comprises a body installable on one end of the barrel and a movable member which includes an interface to which a needle member can be connected, a retention arrangement allowing the movable member to be retained in an initial position, and which can retract into the barrel by a spring; and comprises an assembly which includes a body connectable to the barrel, a member comprising a needle connecting interface and a retention element, and a spring biasing the member toward a retracted position.

In embodiments, the plunger is a hollow plunger. In embodiments, the plunger comprises a piston arranged at a proximal area of the plunger and an actuating end arranged in front of the piston. In embodiments, the plunger further comprises at least one of: the piston being an elastomer or rubber piston; a hollow space sized and configured to receive therein an injection needle; and a locking member adapted to lock with a locking member arranged on the barrel. In embodiments, the barrel and the plunger each comprise a synthetic resin material. In embodiments, the installable needle can be of any type whether packaged individually or in bulk or otherwise maintained in a sealed or sterile condition.

In embodiments, the barrel comprises at least one releasable retaining member. In embodiments, the at least one releasable retaining member comprises plural radially oriented releasable retaining members. In embodiments, the barrel comprises at least one deflectable retaining member. In embodiments, the at least one deflectable retaining member comprises plural radially oriented releasable retaining members.

In embodiments, the device further comprises at least one of: a locking arrangement that is structured and arranged to lock a portion of the needle connecting arrangement to a portion of the plunger; and a locking arrangement selectively locking a portion of the plunger to the barrel upon the plunger reaching a substantially fully depressed position.

In embodiments, when the plunger is moved to a full injection position, a member arranged within the needle connecting arrangement is automatically caused to retract into the plunger. In embodiments, when the plunger is moved to a full injection position, a member arranged within the needle connecting arrangement is automatically caused to retract into the barrel.

In embodiments, the device may further comprising a system providing an indication to the user in regards to a depressed position of the plunger. In embodiments, the device may further comprise a system providing an indication to the user that at least one of the plunger has reached a full injection position and the further forward movement of the plunger will cause a member coupled to a needle to automatically retract into the plunger.

According to another non-limiting embodiment of the invention, there is provided a single-use injection device comprising a barrel, a hollow plunger having a portion structured and arranged to move within the barrel, and a needle connecting arrangement comprising a spring and a needle member having a connecting interface, the needle member being movable automatically by the spring from an initial position to a retracted position within the barrel or the plunger.

According to another non-limiting embodiment of the invention, there is provided a single-use injection device comprising a barrel, a hollow plunger having a portion structured and arranged to move within the barrel and a needle connecting arrangement comprises a spring biased needle connecting member having an interface adapted to mate with a standard needle interface and being movable from an initial position to a retracted position within the barrel or the plunger.

In embodiments, the standard needle interface is a luer-lock interface. In embodiments, the standard needle interface relies substantially only upon contact between tapered surfaces. In embodiments, the standard needle interface relies substantially only upon friction fit contact.

According to another non-limiting embodiment of the invention, there is provided a method of using any of the injection devices described above, wherein the method comprises installing a needle member having a needle and a connecting interface on the injection device and moving the plunger relative to the barrel so as to cause medicine to exit through the needle. The needle member is capable of retracting into the plunger.

According to another non-limiting embodiment of the invention, there is provided a syringe which utilizes one or more features disclosed in U.S. Ser. No. 12/752,186 filed Apr. 1, 2010. The disclosure of this application is hereby expressly incorporated by reference hereto in its entirety.

According to another non-limiting embodiment of the invention, there is provided a syringe which utilizes one or more features disclosed in U.S. Ser. No. 12/951,925 filed on Nov. 22, 2010. The disclosure of this application is hereby expressly incorporated by reference hereto in its entirety.

According to another non-limiting embodiment of the invention, there is provided a syringe which utilizes one or more features disclosed in U.S. Ser. No. 12/752,186 filed Apr. 1, 2010 in combination with one or more features disclosed herein.

According to another non-limiting embodiment of the invention, there is provided a syringe which utilizes one or more features disclosed in U.S. Ser. No. 12/951,925 filed on Nov. 22, 2010 in combination with one or more features disclosed herein.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 1 shows the device with a safety cap installed thereon. The device is in an initial prior-use and/or packaged configuration;

FIG. 12 shows a side view of the inner seal used on the plunger shown in FIG. 1;

FIG. 13 shows a front end view of the inner seal shown in FIG. 12;

FIG. 14 shows a side cross-section view of the inner seal shown in FIG. 12;

FIG. 20 shows a side view of the needle unit used in the device shown in FIG. 1;

FIG. 21 shows a side cross-section view of the needle unit shown in FIG. 20;

FIG. 22 shows a rear end view of the needle unit shown in FIG. 20;

FIG. 23 shows a side cross-section view of the spring used in the device shown in FIG. 1;

FIG. 24 shows a rear end view of the spring shown in FIG. 23;

FIG. 29 shows an enlarged partial view of another modified version of the device of FIGS. 1 and 6. In this embodiment, the device of FIGS. 1 and 6 is modified to eliminate the needle sealing guide and to instead include a puncturable sealing washer to provided sealing between the needle and the syringe body;

FIG. 30 shows a side cross-section view of the device shown in FIG. 29 with the needle unit and spring removed;

FIG. 31 shows a cross-section view through the section (indicated by arrows) shown in FIG. 30;

In FIG. 35, the inner seal is axially retained within the plunger. In FIG. 34, the inner seal has been moved back sufficiently to cause the inner seal to break the frangible projection of the plunger;

In FIG. 36, the frangible projection of the plunger has annular v-shaped recesses which weaken the projection so that it breaks (via shearing forces) in a predictable manner;

In FIG. 48, the seal member is shown in the groove. In FIG. 49, the seal member is shown removed from the groove;

FIGS. 62 and 63 show enlarged views of an optional configuration for a front portion of the injection device in accordance with the invention. This embodiment is similar to that of FIG. 42 except that tapered locking projections are used to axially and non-removably retain the needle assembly on the barrel. Furthermore, an additional real seal member is used to provide additional sealing between the needle assembly and the barrel. In FIG. 62, the additional seal is shown in an installed position. In FIG. 63, the additional seal is shown in a non-installed position.

FIG. 66 shows the embodiment of FIG. 65 with the second component about to be connected to the first component;

FIG. 80 shows the embodiment of FIG. 79 before the front portion of the syringe is threadably connected to the front end of the syringe main body;

FIG. 83 shows certain parts of the embodiment of FIG. 65 in an unconnected/unassembled state;

FIG. 84 shows one way in which a user can mount a front portion of on a syringe. According to this embodiment, the user can then remove the safety cover and install a needle member in the manner shown in FIG. 67; and FIG. 85 shows one way in which a user can mount a front portion of on a syringe. According to this embodiment, the user can then remove the safety cover and use the syringe.

DETAILED DESCRIPTION OF THE INVENTION

Figure 1:
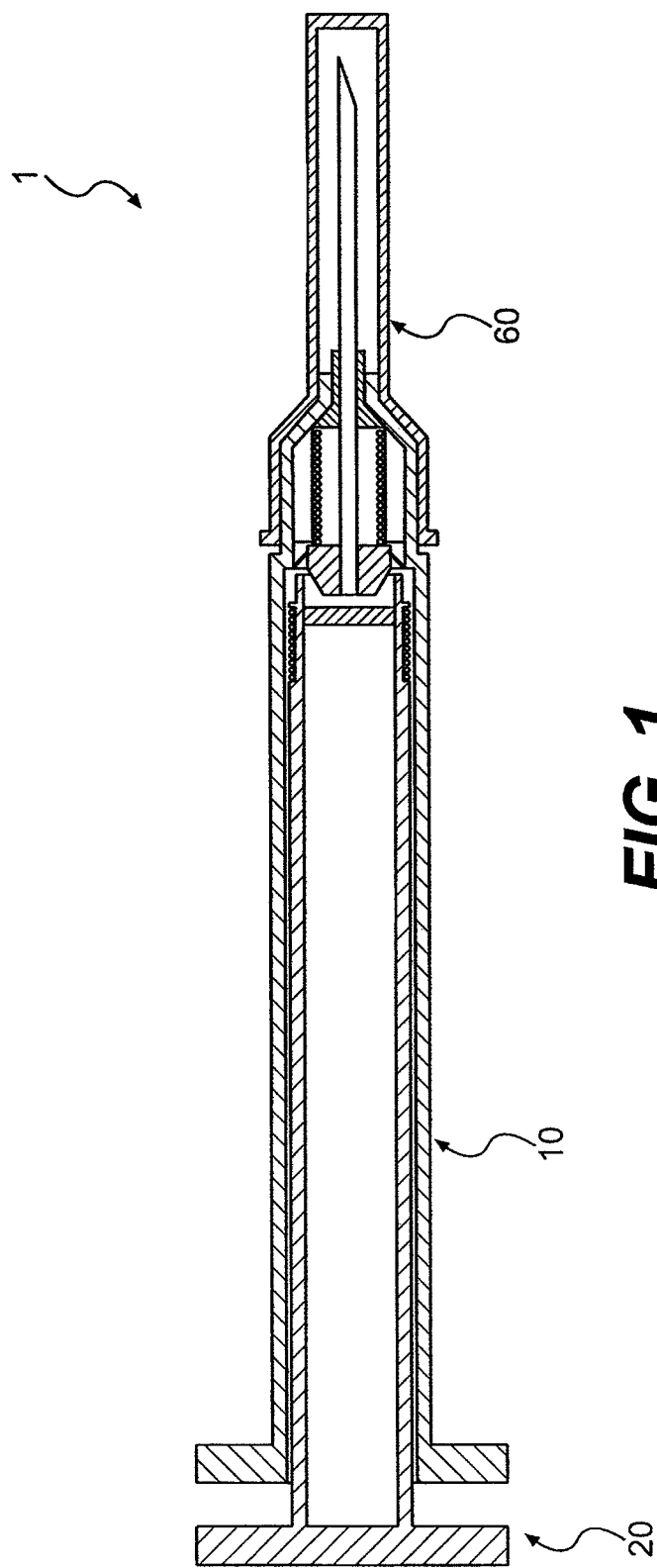
FIG. 1 shows a side cross-section view of a first non-limiting embodiment of the device according to the invention. The needle is not shown in cross-section.

Referring now to the drawings and first to FIGS. 1-17 and 20-26 which shows a first embodiment of an injection device 1. In embodiments, the device is a retractable hypodermic syringe. The syringe includes a generally elongate cylindrical barrel 10 having a transverse flange 11 arranged at a distal end of the barrel 10. The barrel 10 includes a main generally cylindrical section 12. A proximal end of the barrel 10 includes a reduced diameter section 13. A safety cap 60 is removably disposed on a proximal end of the syringe body 10.

Figure 2:
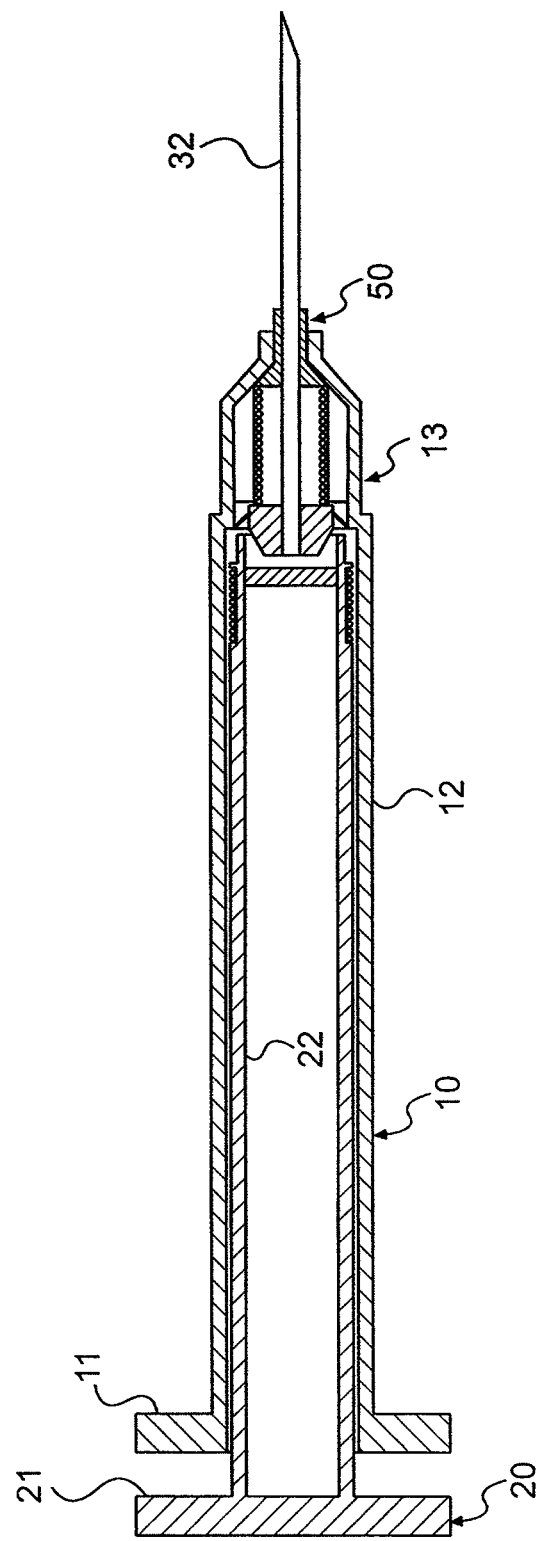
FIG. 2 shows the device of FIG. 1 after the safety cap is removed and in a ready-to-use position.

A needle support 30 has a hub portion 31 that is substantially axially retained within a proximal area of the body 10 (see FIG. 3) and includes a rear end surface which can contact an inner seal 25 of a plunger 20 as will be described in detail below. The needle support 30 also has a main needle portion 32 that has a rear end fixed within a needle hub 31 and a proximal end that is pointed or a puncturing end which extends out past the proximal end of the syringe body 10. A sealing guide member 50 provides sealing between the needle 32 and the syringe body 10, also allows the needle 32 to slide into the syringe 1 as will be described below. A spring 40 is arranged within the section 13 and the syringe body 10, and in the configuration shown in FIG. 2, is fully or nearly fully compresses. The spring 40 biases the needle unit 30 towards a distal end of the syringe 1.

Substantially arranged within the barrel 10 of the syringe is movably disposed a plunger 20. The plunger 20, like the syringe body 10, includes an end flange 21 which is typically engaged by the thumb of the user while the transverse flange 11 is engaged by the fingers of the user in order to enable the plunger 20 to be forced into the barrel 10 for the purpose of expelling the medicament from the barrel 10 through the needle 32. The plunger 20 additionally includes a generally cylindrical space 22 which is sized to receive therein the needle unit 30 (see FIG. 5). A piston 23 (see FIG. 9) is arranged on a proximal end of the plunger 10. The plunger 20 also utilizes a proximal engaging end 24 which is sized and configured to engage with deflectable retaining members 15 (see FIGS. 6 and 7) when the plunger 20 is fully depressed. An inner seal or sealing member 25 is arranged within the plunger 20. As is apparent from FIGS. 6 and 7, the seal 25 has frangible circumferential projections which are sized and configured to break and/or shear off when the plunger 20 is depressed to the point where the seal 25 contacts the hub 31. Before the projections of the seal 25 break, they provide sealing between the seal 25 and the plunger 20. This sealing ensures that no medication passes into the plunger space 22 until the seal 25 is broken.

Figure 6:
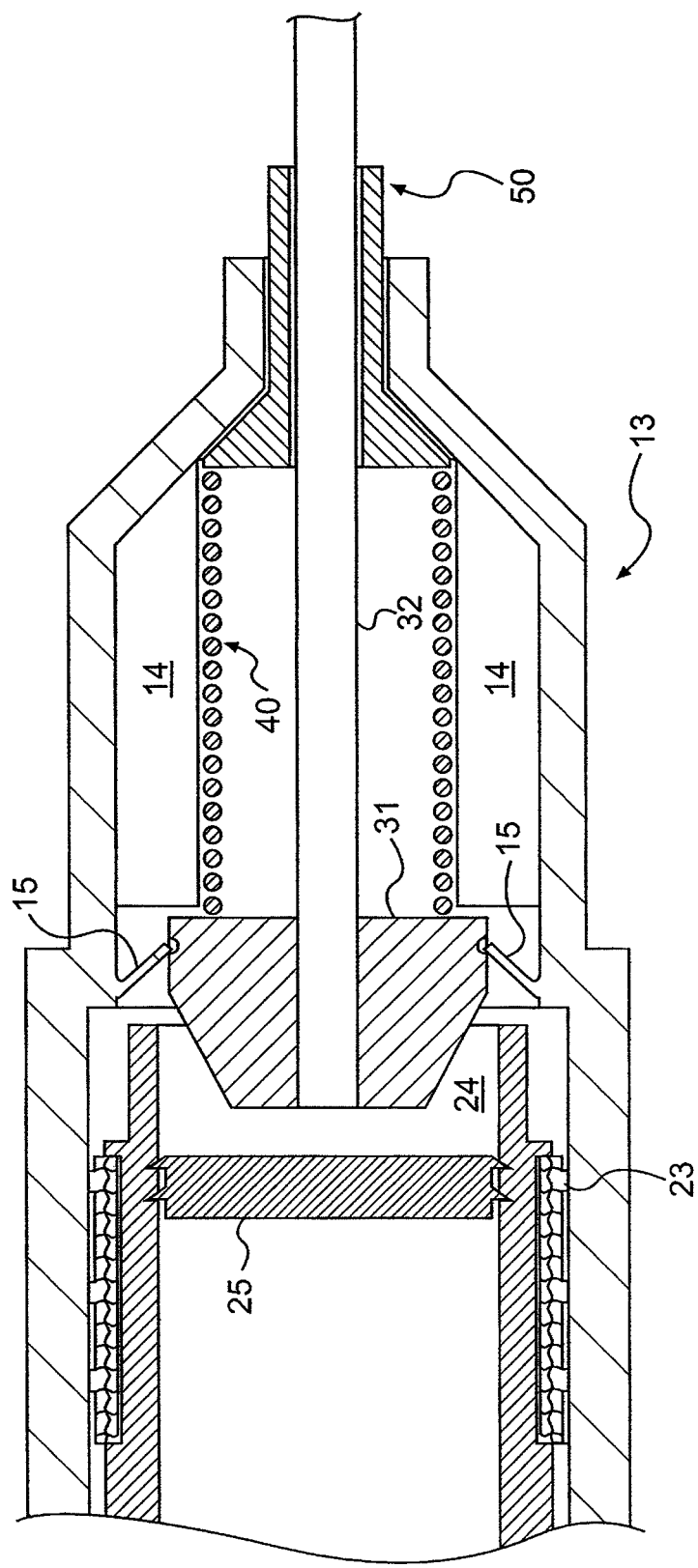
FIG. 6 shows an enlarged partial view of the device of FIG. 4 just before the plunger reaches the fully depressed position.
Figure 7:
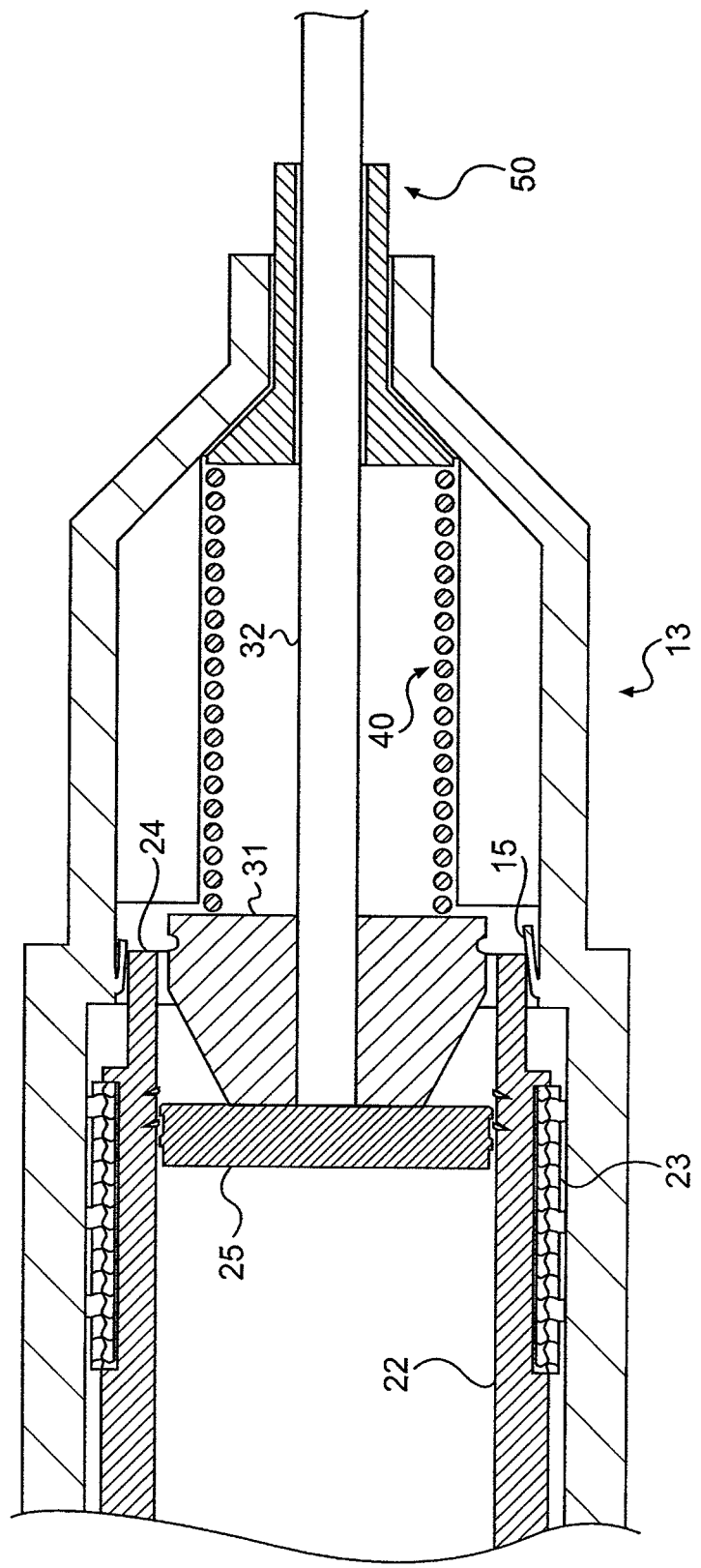
FIG. 7 shows an enlarged partial view of the device of FIG. 4 just as the plunger reaches the fully depressed position thereby causing deflection of the retaining members and breaking of the frangible plunger seal caused by movement of the plunger against a rear end of the needle hub.

As is apparent from FIGS. 6 and 7, to unsure that the needle unit 30 is prevented from moving forwards when the plunger 20 is fully depressed, a plurality of stop projections or ribs 14 are arranged within the section 13 of the syringe body 10.

Figure 3:
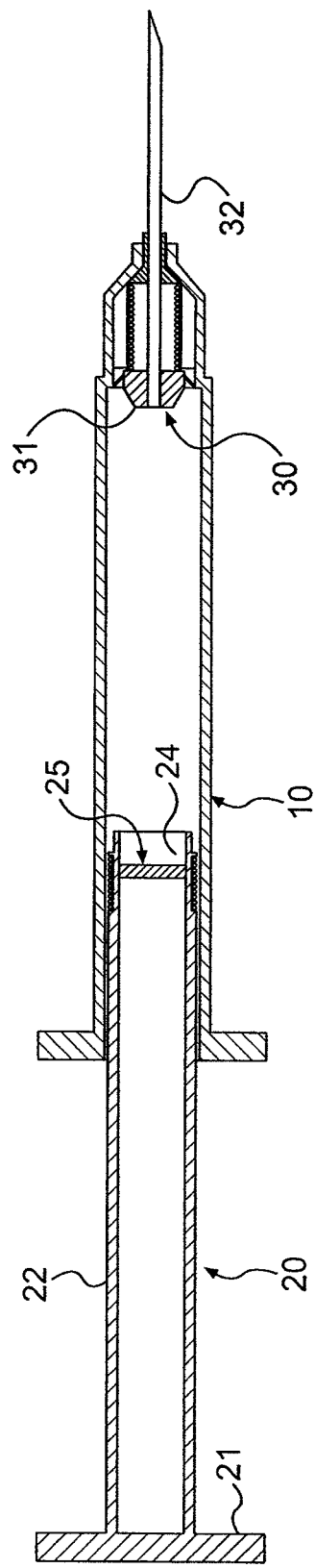
FIG. 3 shows the device of FIG. 2 with the plunger retracted as would occur when medicine is caused to be suctioned into the syringe via the needle.
Figure 4:
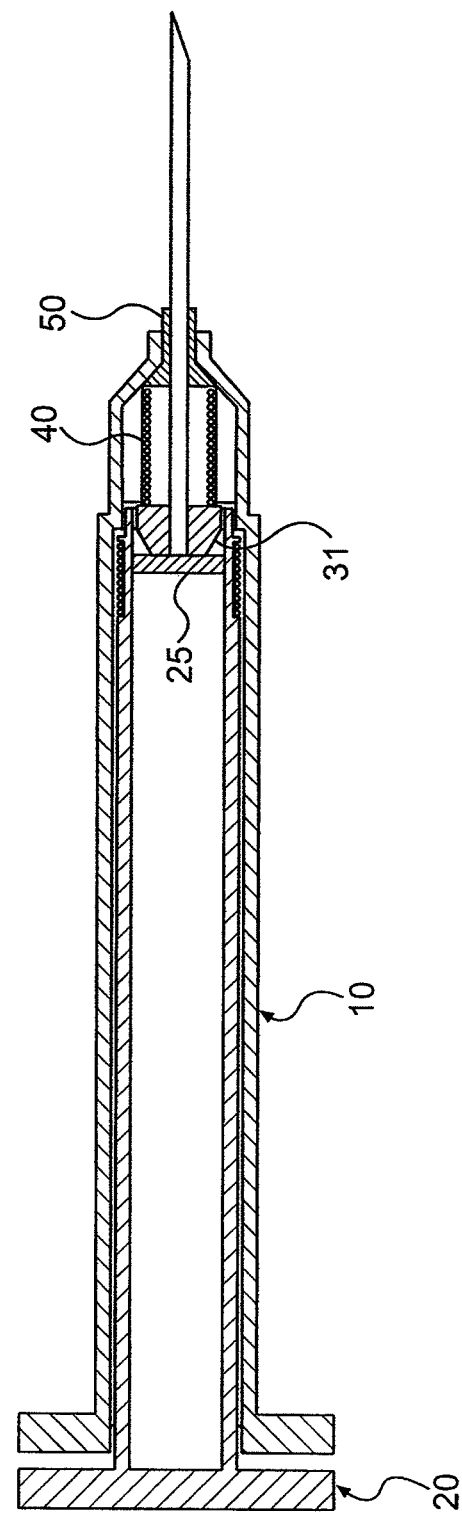
FIG. 4 shows the device with the plunger fully depressed as would occur during injection. In this position, the leading end of the plunger has moved deflectable retaining members out of locking engagement with the needle hub. Moreover, a rear end of the needle hub has caused an inner seal, i.e., a frangible plunger seal, to come out of sealing engagement with the needle hub.
Figure 5A:
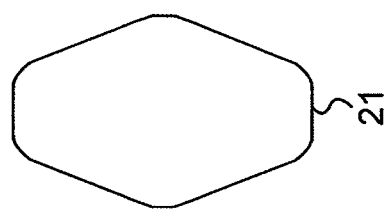
FIG. 5a shows a rear end view of the device of FIG. 5.
Figure 5:
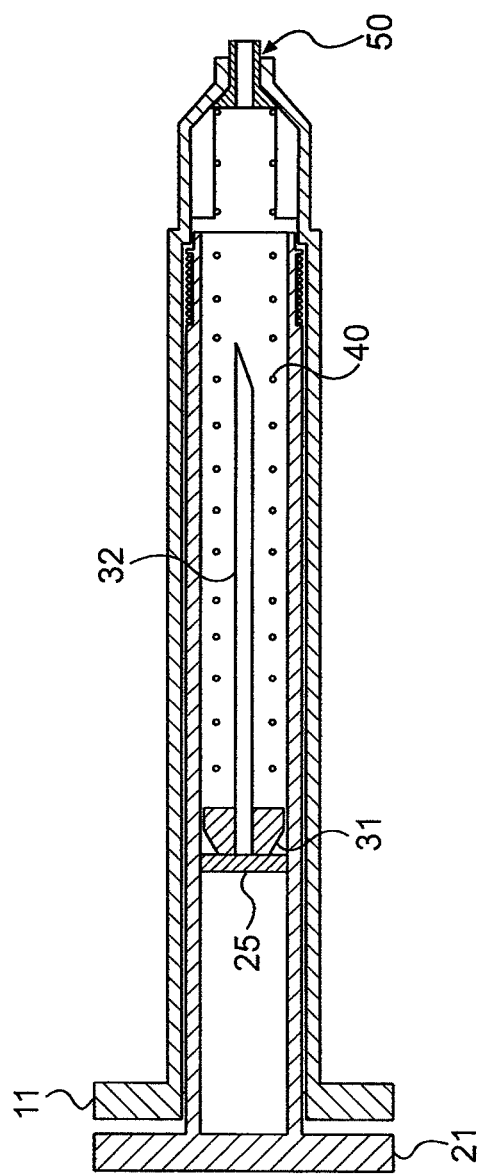
FIG. 5 shows the device after the needle unit is caused to automatically retract into the plunger under the biasing force of a spring. The configuration shown in FIG. 5 occurs automatically when the plunger reaches the position shown in FIG. 4.

The operation of the device shown FIGS. 1-7 will now be described. Once the user obtains the device 1 shown in FIG. 1, he or she can then remove the safety cap 60. The device 1 so shown in FIG. 2 can now be used for, e.g., injection. This can occur when the user injects the needle 32 into a medication container and withdraws the plunger 20 as shown in FIG. 3. This causes medication fluid to fill the space in the body 10 between the plunger piston 23 and seal 25 and the sealing member 50. As this point, the user can move the plunger 20 forwards slightly to remove any air in the syringe 1. The needle 32 can then be injected into, e.g., tissue. Then, the user will depress the plunger 20 to cause the medication to pass out of the needle 32. Once fully or nearly fully depressed, the proximal end 24 of the plunger 20 contacts the deflectable retaining members 15 (see FIGS. 6 and 7) and causes them to deflect out of locking and/or retaining engagement with the hub 31. Since engagement between the deflectable retaining members 15 and the hub 31 is the only mechanism which prevents the spring 40 from moving the needle unit 30 backwards, once this engagement is removed, the needle unit 30 will be forced backwards by the spring 40. Also, once fully or nearly fully depressed, the seal 25 of the plunger 20 contacts the rear surface of the hub 31 (see FIGS. 6 and 7). Since the ribs 14 prevent any forward movement of the hub 31, contact between the seal 25 and the hub 31 causes the frangible sealing projections of the seal 25 to shear or break. At this point, the spring 40 automatically expands axially and pushes the needle unit 30 and seal 25 into the space 22 disposed inside the plunger 20 as shown in FIG. 5. This action withdraws the needle 32 into the syringe and renders the device 1 unusable. The device 1 of FIG. 5 can then be safely disposed of without the user having to worry about being accidently pricked by the needle 32, which is safely disposed inside the plunger 20.

In embodiments, the engagement between the deflectable retaining members 15 and the hub 31 is removed or disengages prior to the sealing engagement between the seal 25 and the plunger 20. In other embodiments, the engagement between the deflectable retaining members 15 and the hub 31 is removed or disengages just prior to the sealing engagement between the seal 25 and the plunger 20. In embodiments, the engagement between the deflectable retaining members 15 and the hub 31 is not removed or disengaged until after the frangible sealing engagement between the seal 25 and the plunger 20 is broken. In embodiments, the engagement between the deflectable retaining members 15 and the hub 31 is not removed or disengaged until just after the frangible sealing engagement between the seal 25 and the plunger 20 is broken. In embodiments, the force required to unlock or remove the engagement between the deflectable retaining members 15 and the hub 31 is less than that required to break the sealing engagement between the seal 25 and the plunger 20. In embodiments, the force required to unlock or remove the engagement between the deflectable retaining members 15 and the hub 31 is greater than that required to break the sealing engagement between the seal 25 and the plunger 20. In embodiments, the force required to unlock or remove the engagement between the deflectable retaining members 15 and the hub 31 is substantially equal to that required to break the sealing engagement between the seal 25 and the plunger 20. In embodiments, a noise is produced (providing an auditory signal to the user) when the engagement between the deflectable retaining members 15 and the hub 31 is removed. In embodiments, a noise is produced (providing an auditory signal to the user) when the sealing engagement between the seal 25 and the plunger 20 is broken. In embodiments, a visual indication is produced (providing a visual signal to the user) when the engagement between the deflectable retaining members 15 and the hub 31 is removed. In embodiments, a visual indication is produced (providing a visual signal to the user) when the sealing engagement between the seal 25 and the plunger 20 is broken. Such visual indicators can be facilitated by making the plunger 20 and body 10 substantially transparent and/or translucent.

Figure 8:
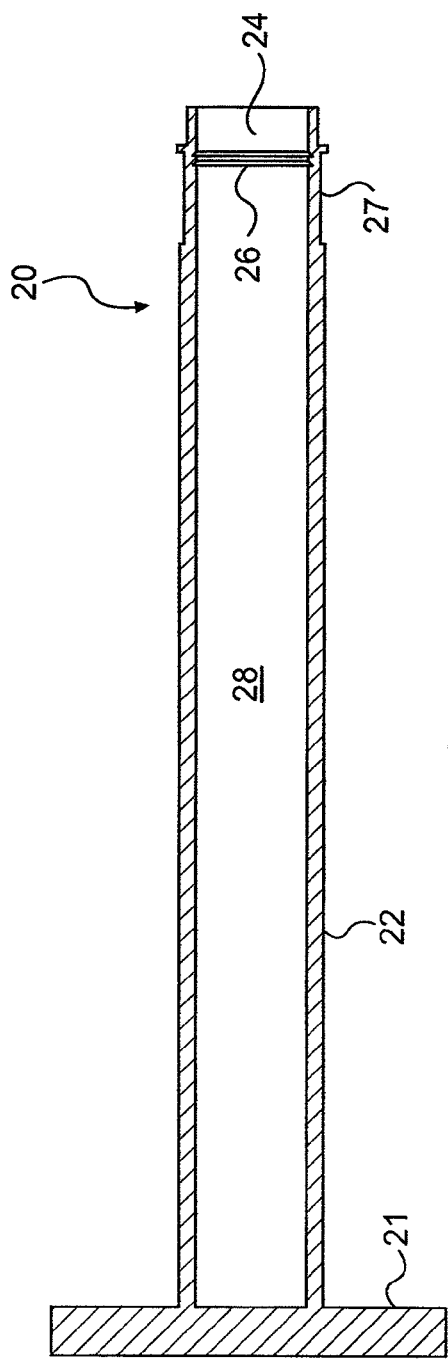
FIG. 8 shows a side cross-section view of the plunger used on the first non-limiting embodiment shown in FIG. 1 and with the plunger piston and inner seal removed.
Figure 9:
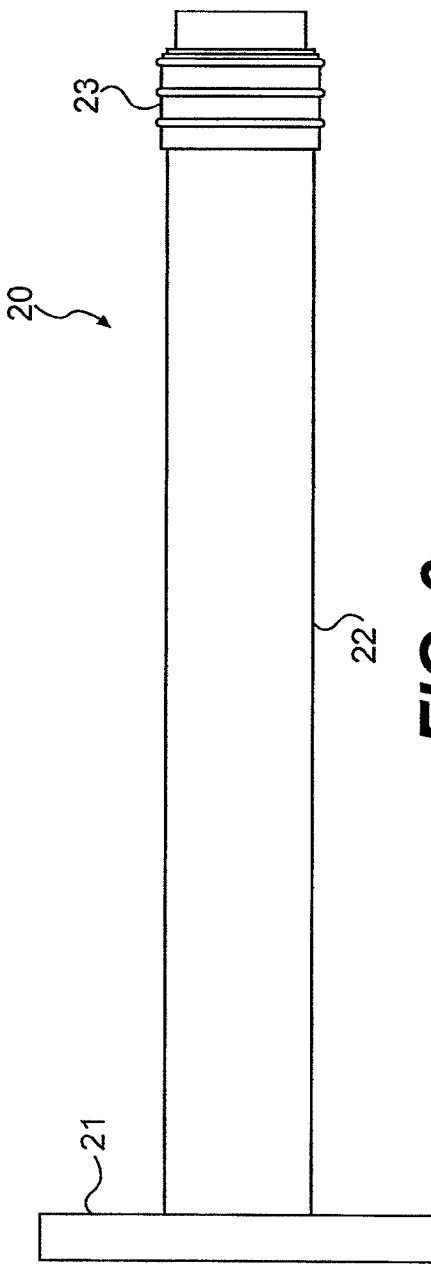
FIG. 9 shows a side view of the plunger of FIG. 8 with the plunger piston installed thereon.
Figure 11:
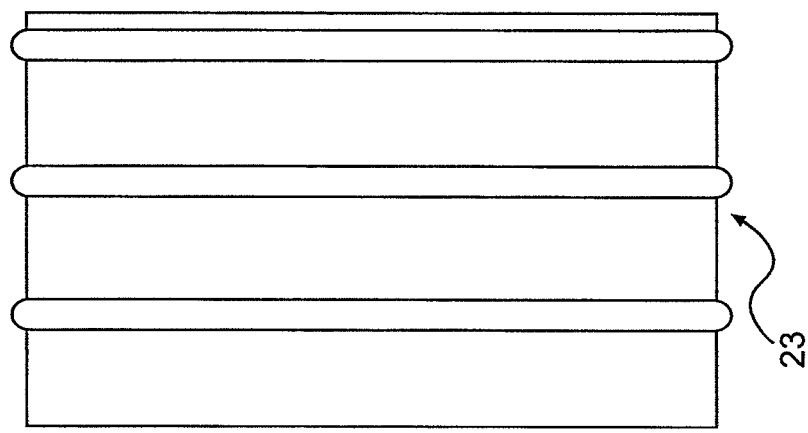
FIG. 11 shows a side view of the plunger piston shown in FIG. 10.
Figure 10:
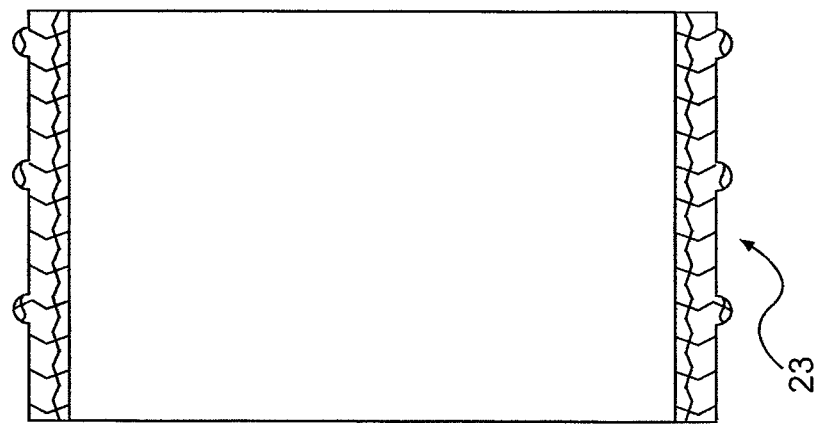
FIG. 10 shows a side cross-section view of the plunger piston used on the plunger shown in FIG. 9.

FIGS. 8 and 9 show views of the plunger 20 used on the first non-limiting embodiment shown in FIG. 1. The plunger 20, in embodiments, is a one-piece integrally formed member to which is axially secured a piston 23 and an inner seal 25. The plunger 20 includes a distal flange 21, a main cylindrical section 22, a generally cylindrical proximal end 24, one or more inner generally circumferential tapered recesses 26, a generally cylindrical recess 27 sized and configured to receive therein and axially retain the piston 23, and a generally cylindrical space 28.

FIGS. 8 and 9 show views of the piston 23 used on the plunger of FIGS. 8 and 9. The piston 23, in embodiments, is a one-piece integrally formed member to which is axially secured within the recess 27 of the plunger 20. In embodiments, it can be substantially similar at pistons conventionally used in syringes which include plural external circumferential sealing projections.

FIGS. 12-14 show views of the inner seal 25 used on the plunger of FIGS. 8 and 9. The seal 25, in embodiments, is a one-piece integrally formed member to which is axially secured to an inner portion of the plunger 20. In embodiments, the seal 25 includes a distal or rear surface 25a, one or more tapered external circumferential projections 25b, and a proximal surface 25c. The one or more tapered external circumferential projections 25b each extend into one of the recesses 26 of the plunger 20. The tapered external circumferential projections 25b are designed to be frangible and sized and configured to shear upon experiencing a predetermined force applied to the surface 25c. The shape, i.e., rearward orientation, of the tapered external circumferential projections 25b is such that a force applied to the surface 25c will cause the projections 25b to grip recesses 26 by a greater amount and such that a force applied to the surface 25a will cause the projections 25b to grip recesses 26 by a lesser amount. In embodiments, a force applied to the surface 25a will cause the projections 25b to start to move out of engagement with the recesses 26 by a significant amount without breaking.

Figure 15:
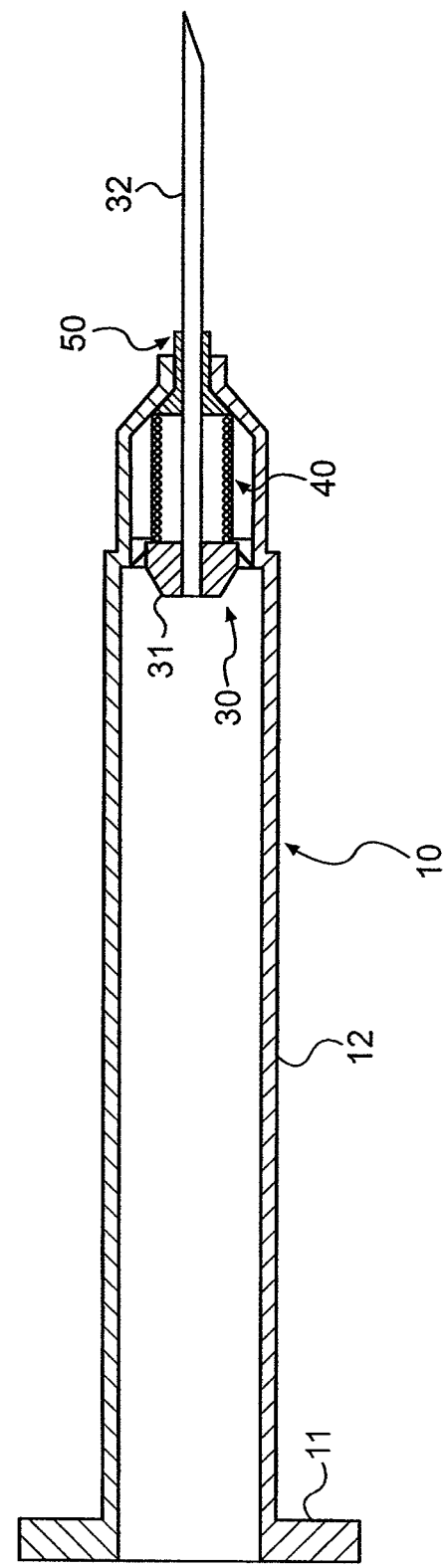
FIG. 15 shows a side cross-section view of the device shown in FIG. 1 with the plunger removed.
Figure 16:
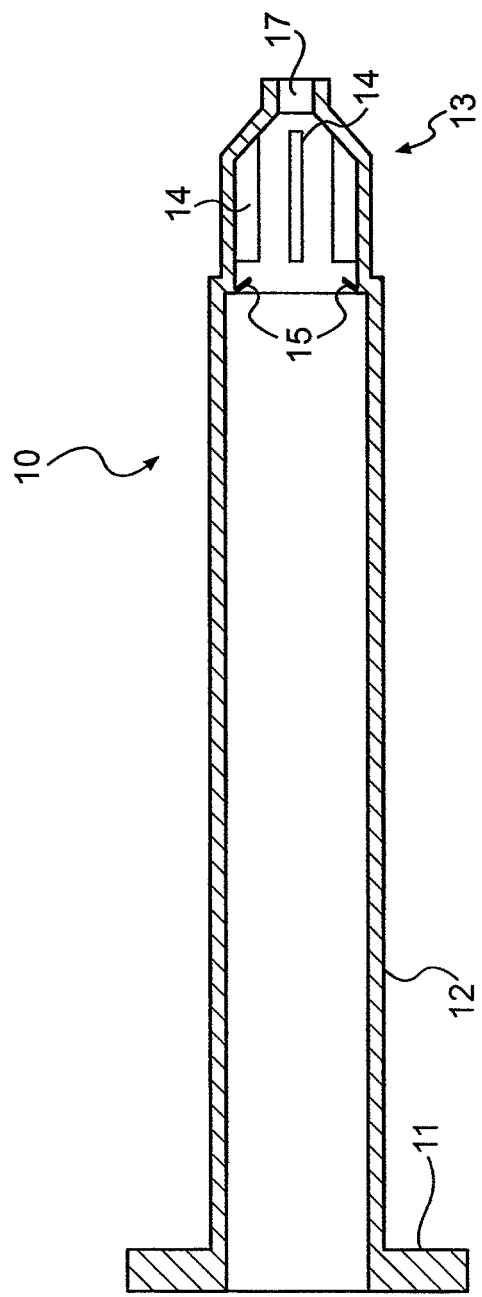
FIG. 16 shows a side cross-section view of the syringe body used in the device shown in FIG. 1.
Figure 19:
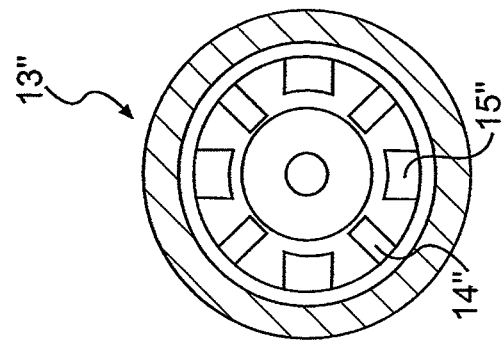
FIG. 19 shows a rear end view of still another embodiment of the syringe body.
Figure 18:
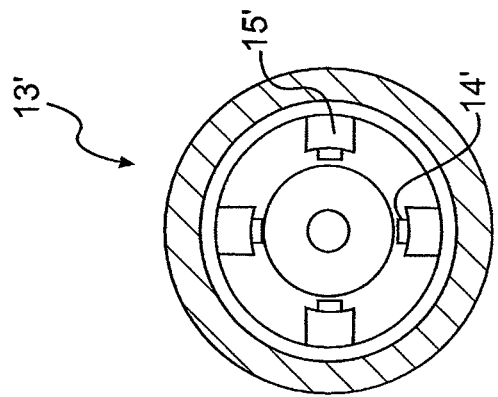
FIG. 18 shows a rear end view of another embodiment of the syringe body.
Figure 17:
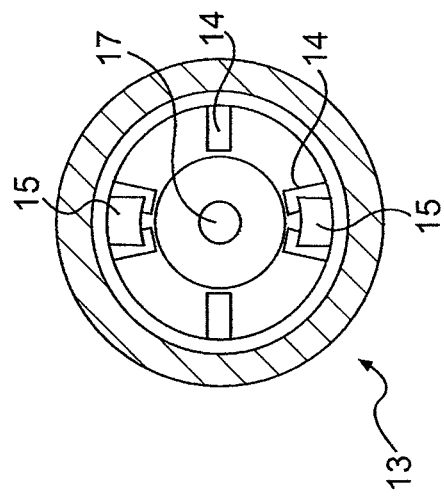
FIG. 17 shows a rear end view of the syringe body shown in FIG. 16.

FIGS. 15-17 show how the syringe body 10 used on the device of FIG. 1 receives therein the seal guide 50, the needle member 30 and the spring 40 before receiving therein the plunger 20 of FIGS. 8 and 9. The body 10, in embodiments, is a one-piece integrally formed member. The body 10 includes a distal flange 11, a main cylindrical section 12, a generally cylindrical proximal end 13, one or more inner radially oriented spaced-apart ribs 14, plural deflectable retaining members 15 which are equally spaced-apart and which are sized and configured to engage with the circumferential recess 33 of the needle unit 30 (see FIG. 20), and a generally cylindrical opening 17 sized and configured to receive therein (in a sealing and/or press-fit manner) the generally cylindrical surface 50a of the sealing guide 50 (see FIG. 26). In embodiments, two oppositely arranged deflectable retaining members 15 are utilized. In embodiments, three equally spaced deflectable retaining members 15 are utilized. In embodiments, between four and eight equally spaced deflectable retaining members 15 are utilized. FIG. 18 shows an optional embodiment wherein section 13' utilizes four equally spaced deflectable retaining members 15' and four ribs 14' which have the same orientation. FIG. 19 shows an optional embodiment wherein section 13" utilizes four equally spaced deflectable retaining members 15" and four ribs 14" which are offset with respect to one another. These systems/configurations can be utilized on any of the herein disclosed device embodiments.

FIGS. 20-22 show views of the needle unit 30 used on the device 1 of FIG. 1. The needle unit 30, in embodiments, can be a one-piece integrally formed member. The needle unit 30, in embodiments, utilizes a one-piece needle hub 31 and a one-piece needle 32 that has a distal end secured (e.g., press-fit) within an opening the hub 31. The needle hub 31, in embodiments, also utilizes a tapered section 36 and a circumferential groove or recess 33 which can receive therein the free ends of the deflectable gripping members 15 (see FIG. 6). In embodiments, the needle 32 has a main lumen 34 and a puncturing end 35. In embodiments, the needle 32 can be substantially similar at pistons conventionally used in syringes which include plural external circumferential sealing projections.

FIGS. 23 and 24 show views of the spring 40 used on the embodiment of FIG. 1. FIG. 23 shows the spring 40 in an expanded or relaxed position. In the position shown in FIG. 1, the spring 40 is fully or nearly fully compressed. Expansion of the spring 40 causes the needle unit 30 to retract fully into the plunger 20 (see FIG. 5).

Figure 25:
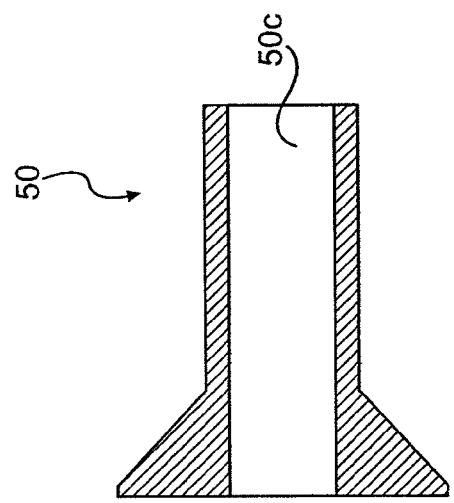
FIG. 25 shows a side cross-section view of the needle sealing guide member used in the device shown in FIG. 1.
Figure 26:
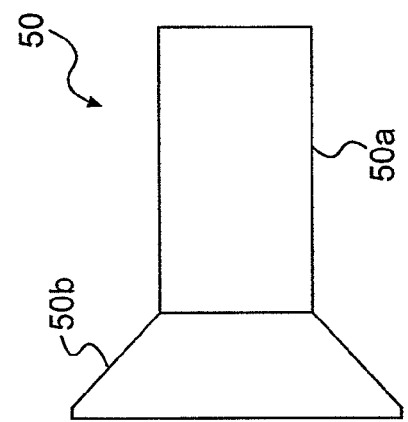
FIG. 26 shows a side view of the needle sealing guide member shown in FIG. 25.

FIGS. 25 and 26 show views of the sealing guide 50 used on the embodiment of FIG. 1. The seal 50 has a generally cylindrical section 50a, a tapered section 50b, and a generally cylindrical opening 50c. The generally cylindrical section 50a is sized and configured to sealingly and frictionally engage with opening 17 in the body 10. The tapered section

50b is sized and configured to sealingly and frictionally engage with a corresponding tapered surface of the body 10. The generally cylindrical opening 50c is sized and configured to sealingly engage with the needle 32. The seal 50, in embodiments, can be a one-piece integrally formed member.

Figure 27:
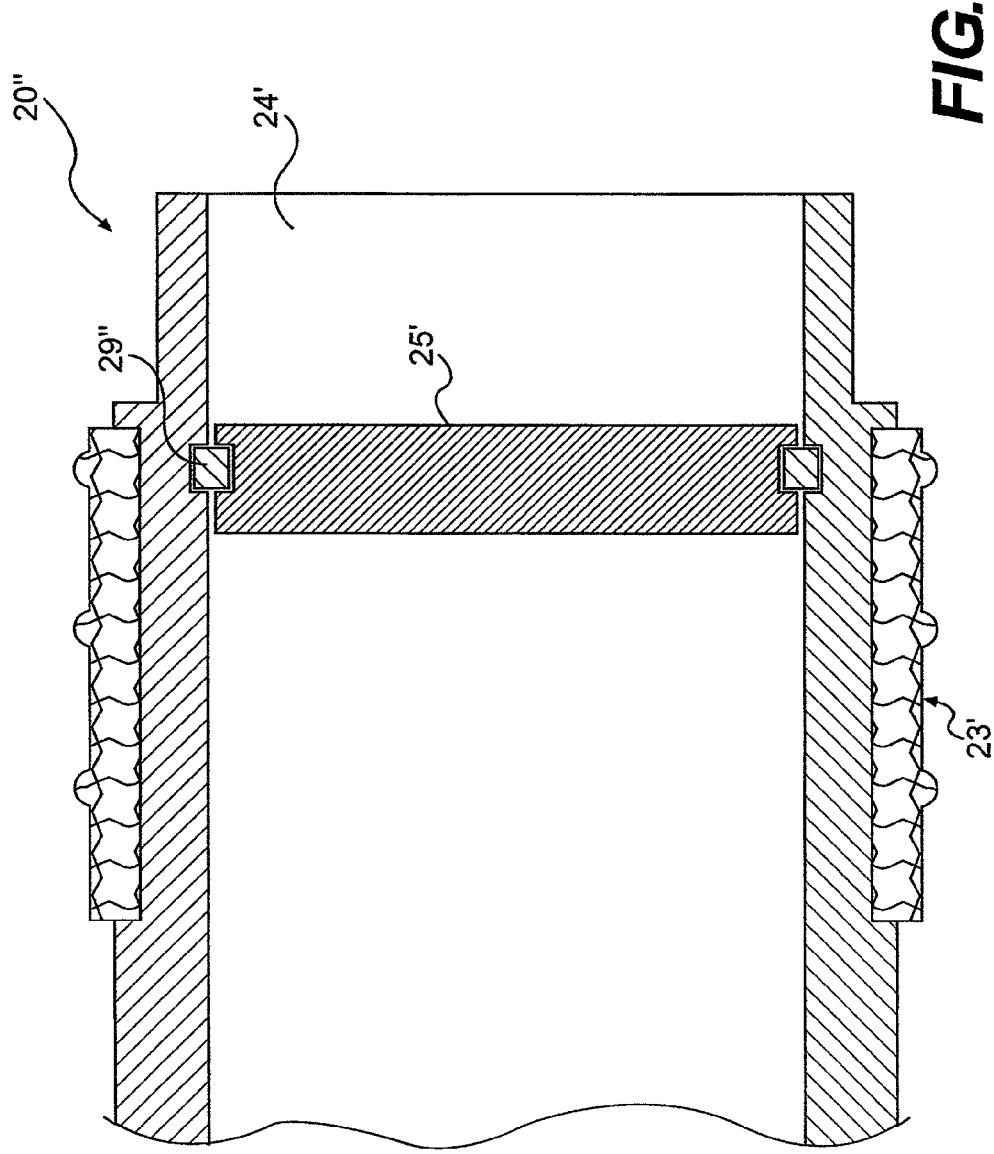
FIG. 27 shows an enlarged partial view of another embodiment of a plunger which can be used on a device of the type shown in FIG. 1. The plunger is similar to that used in FIG. 1 except that the inner seal is axially retained within the plunger via a separately formed ring.

FIG. 27 shows an enlarged partial view of another embodiment of a plunger 20' which can be used on a device of the type shown in FIG. 1. The plunger 20' is similar to that used in FIG. 1 except that the inner seal 25' is axially retained within the plunger 20' via a separately formed ring 29'. The ring 29' is seated in a circumferential recess formed in the seal 25'. In embodiments, a distal circumferential shoulder is sized and configured to break when the plunger 20' is fully depressed. In embodiments, a ring 29' is a frangible ring and is sized and configured to break when the plunger 20' is fully depressed. As with the previous embodiments, the plunger 20' includes a proximal engaging end 24' and a piston 23'. This system/configuration can be utilized on any of the herein disclosed device embodiments.

Figure 28:
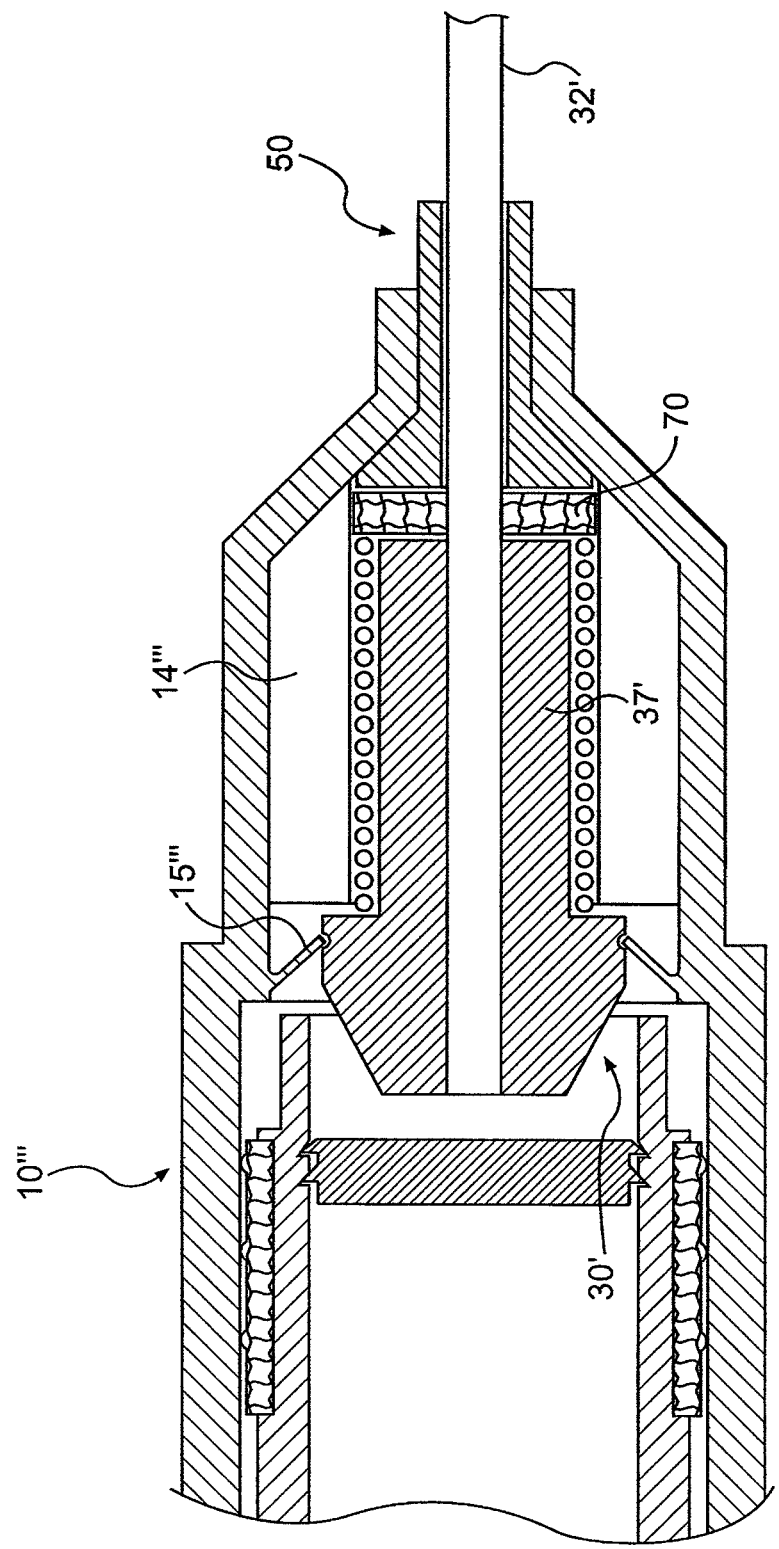
FIG. 28 shows an enlarged partial view of a modified version of the device of FIGS. 1 and 6. In this embodiment, the device of FIGS. 1 and 6 is modified to include a puncturable sealing washer to provided sealing between the needle and the syringe body.

FIG. 28 shows an enlarged partial view of a modified version of the device of FIG. 1. In this embodiment, the device of FIG. 1 is modified to include a puncturable sealing washer 70 to provided sealing between the needle 32' and the guide 50 and/or syringe body 10". The needle unit 30' is also modified to include a generally cylindrical section 37'. As with the previous embodiments, the device utilizes ribs 14" and deflectable retaining members 15". This system/configuration can be utilized on any of the herein disclosed device embodiments.

FIGS. 29-31 show views of another modified version of the device of FIG. 1. In this embodiment, the device of FIG. 28 is modified to remove the ribs and the guide seal and instead sealing is provided between the opening 17$^{IV}$ of the syringe body 10$^{IV}$ and the needle 32'. As with the previous embodiments, the device utilizes deflectable retaining members 15$^{IV}$. This system/configuration can be utilized on any of the herein disclosed device embodiments.

Figure 32:
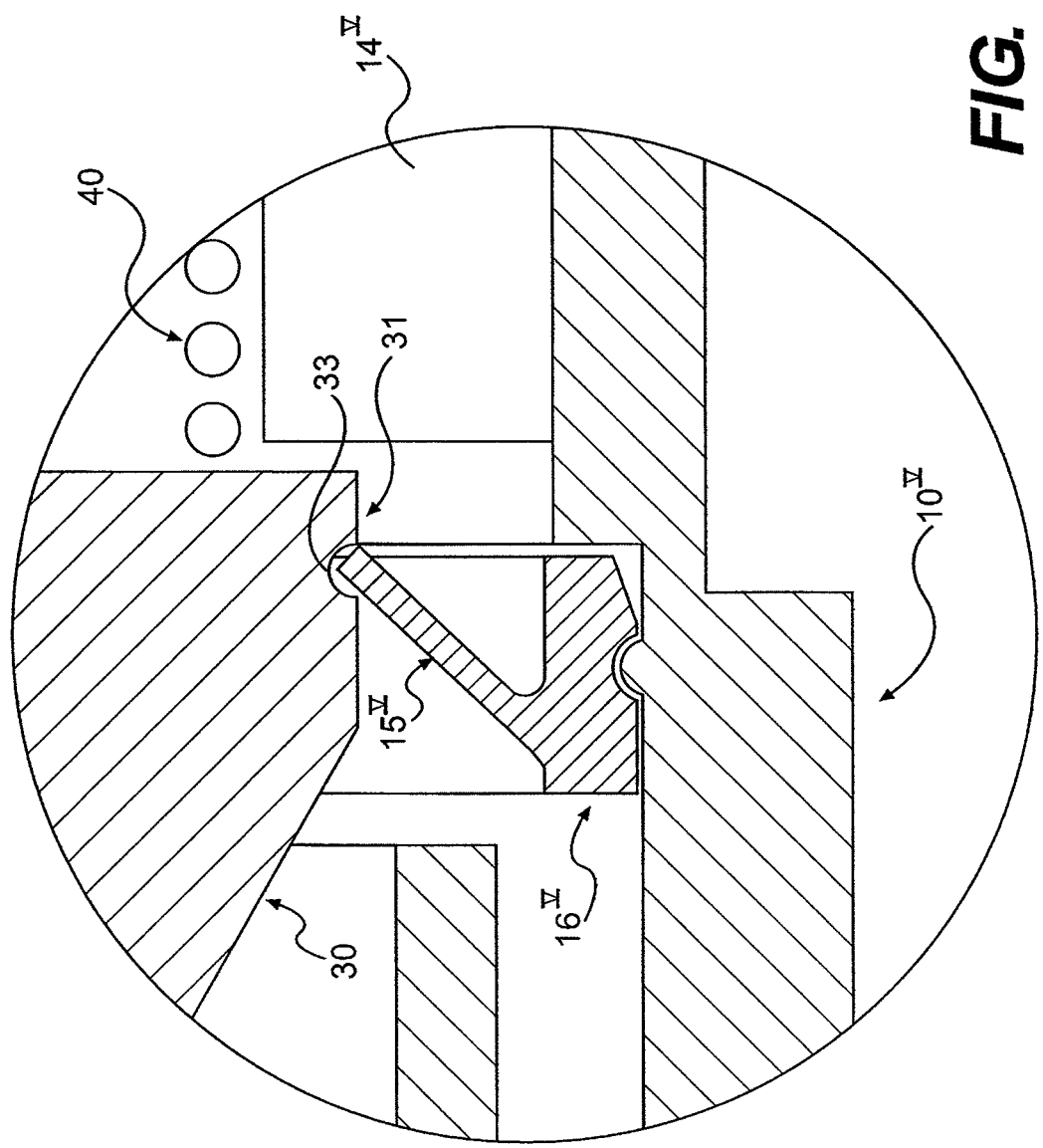
FIG. 32 shows an enlarged partial view of another modified version of the device of FIG. 1. In this embodiment, the device of FIG. 1 is modified to replace the integrally formed deflectable retaining members with a separately formed ring which is axially retained in the syringe body and which has the deflectable retaining members.

FIG. 32 shows an enlarged partial view of another modified version of the device of FIG. 1. In this embodiment, the device of FIG. 1 is modified to replace the integrally formed deflectable retaining members with a separately formed ring 16$^{V}$ which is axially retained in the syringe body 10$^{V}$ via a projection and recess securing arrangement. The ring 16$^{V}$ is a one-piece member that has the deflectable retaining members 15$^{V}$. This system/configuration can be utilized on any of the herein disclosed device embodiments.

Figure 33:
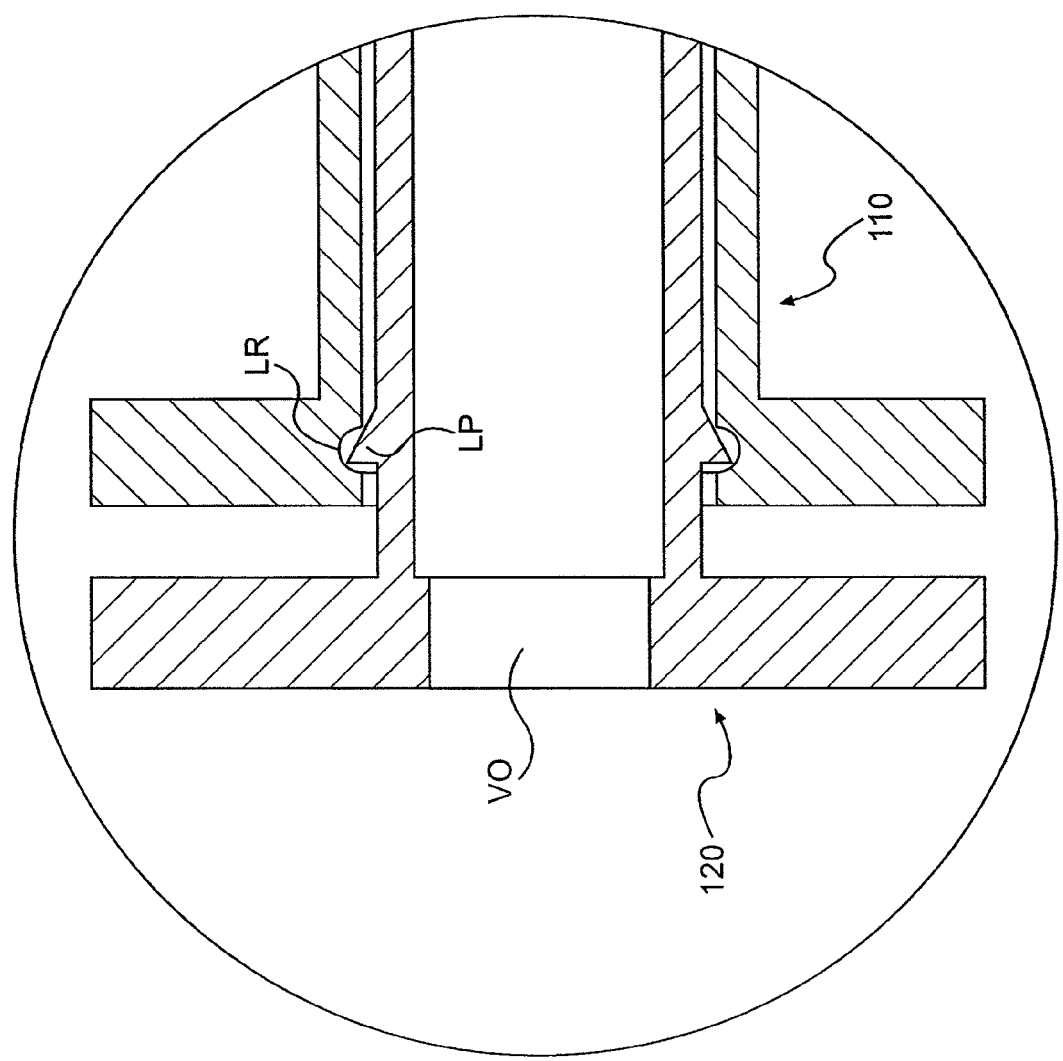
FIG. 33 shows an enlarged partial view of another modified version of the device of FIG. 1. In this embodiment, the device of FIG. 1 is modified to include a locking system to prevent re-use of the device as well as an optional vent opening. The locking system locks the plunger to the syringe body when the plunger is fully or nearly fully depressed.

FIG. 33 shows an enlarged partial view of another modified version of the device of FIG. 1. In this embodiment, the device of FIG. 1 is modified to include a locking system to prevent re-use of the device as well as an optional vent opening. The locking system has the form of one or more projections LP and one or more recesses LR adapted to receive therein the locking projection LP. The locking system locks the plunger 120 to the syringe body 110 when the plunger 120 is fully or nearly fully depressed. Other configurations can also be utilized such as arranging the locking projections LP on the syringe body 110 and the locking recesses LR on the plunger 120. The projection LP can be, in embodiments, continuous or intermittent and the recess LR can be a circumferential recess. The device can also be modified to utilize an optional vent opening VO in the plunger 120. The locking system prevents re-use of the device. The systems shown in FIG. 33 can be utilized on any of the herein disclosed device embodiments.

Figure 35:
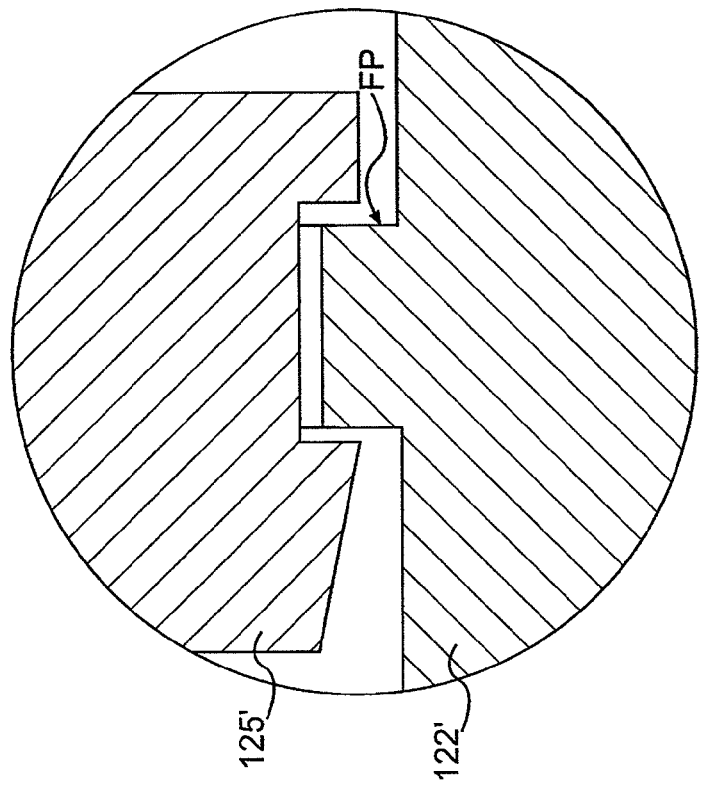
FIGS. 34 and 35 each show an enlarged partial view of another embodiment of a plunger which can be used on a device of the type shown in FIG. 1. The plunger is similar to that used in FIG. 1 except that the inner seal is axially retained within the plunger via a recess and frangible projection system.
Figure 34:
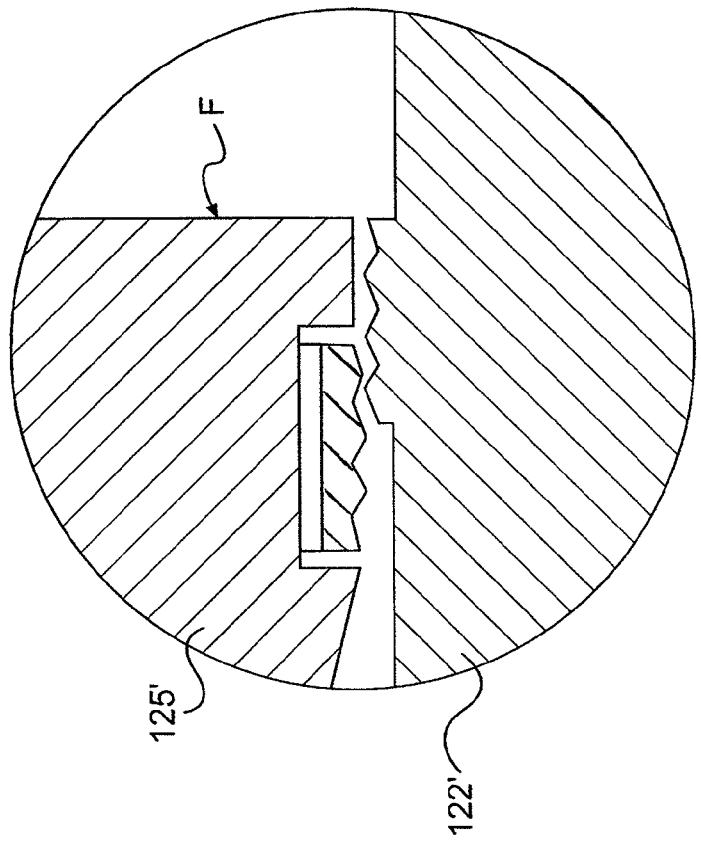

FIGS. 34 and 35 each show an enlarged partial view of another embodiment of a plunger which can be used on a device of the type shown in FIG. 1. The plunger is similar to that used in FIG. 1 except that the inner seal 125' is axially retained within the plunger body 122' via a recess and frangible projection FP. In FIG. 35, the inner seal 125' is axially retained within the plunger. In FIG. 34, the inner seal 125' has been moved back sufficiently under the action of a force F to cause the inner seal 125' to break the frangible projection FP of the plunger. The systems shown in FIGS. 34 and 35 can be utilized on any of the herein disclosed device embodiments.

Figure 36:
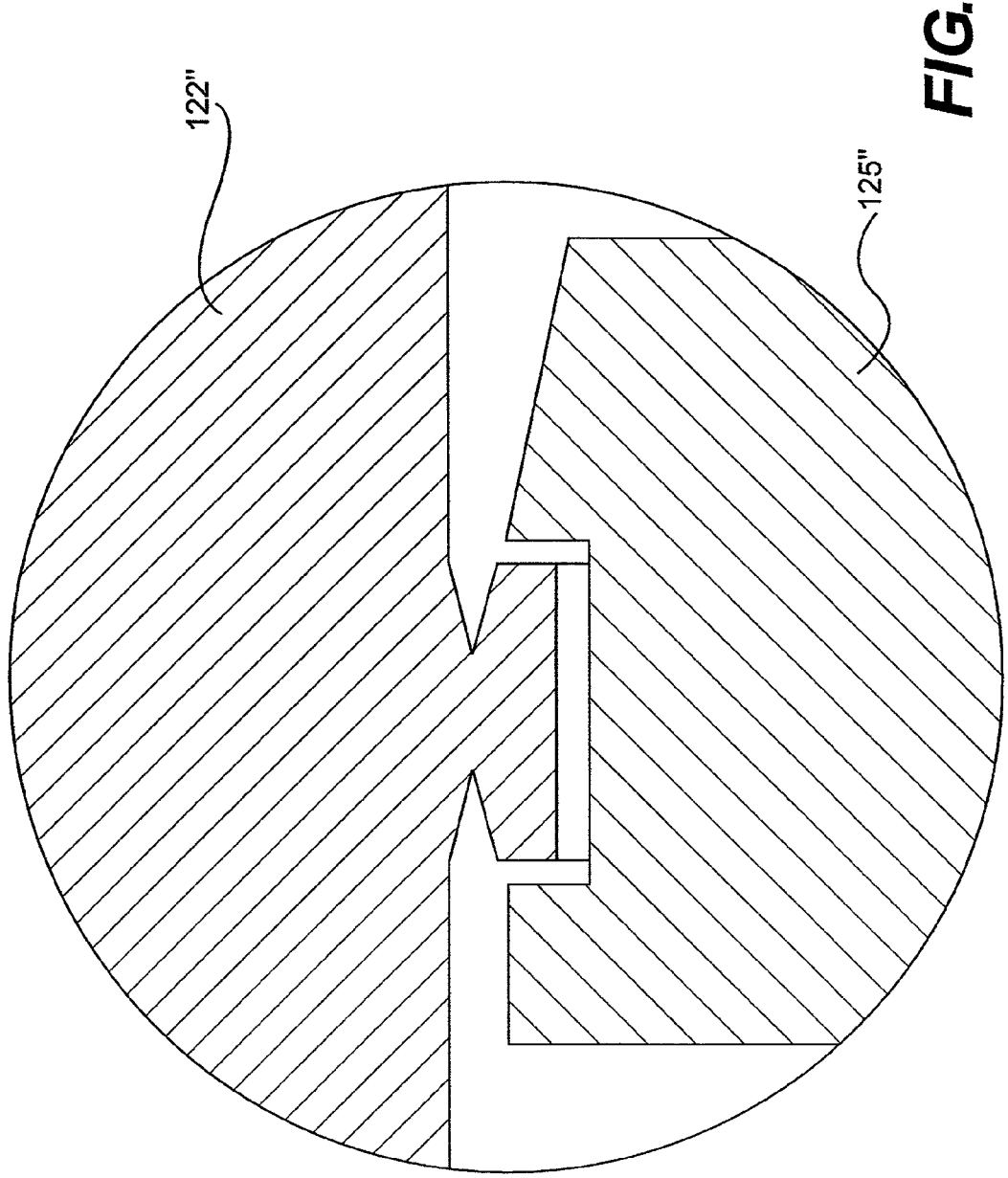
FIG. 36 shows an enlarged partial view of another embodiment of a plunger which can be used on a device of the type shown in FIG. 1. The plunger is similar to that used in FIG. 1 except that the inner seal is axially retained within the plunger via a recess and frangible projection system.

FIG. 36 shows an enlarged partial view of another embodiment of a plunger which can be used on a device of the type shown in FIG. 1. The plunger is similar to that used in FIG. 1 except that the inner seal 125" is axially retained within the plunger body 122" via a recess and a selectively weakened frangible projection FP'. In FIG. 36, the frangible projection FP' of the plunger has annular v-shaped recesses which weaken the projection FP' so that it breaks (via shearing forces) in a predictable manner. The system shown in FIG. 36 can be utilized on any of the herein disclosed device embodiments.

Figure 37:
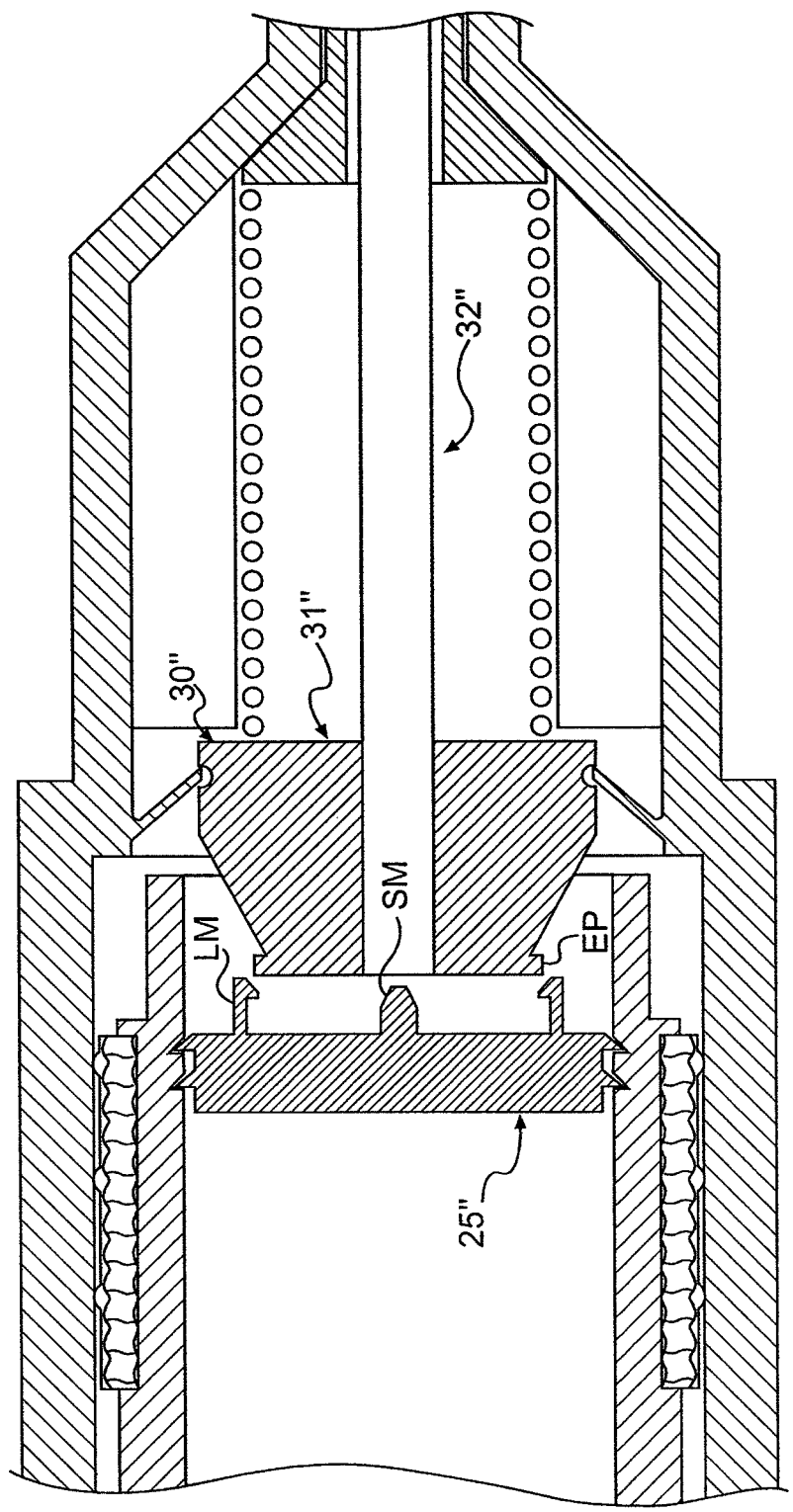
FIG. 37 shows an enlarged partial view of another non-limiting embodiment of a device. The device is similar to that of FIG. 1, except that it utilizes a sealing member that utilizes a sealing member which can extend into the opening of the needle which prevents medication from passing into the needle when it is inserted into the distal end of the needle. The device also utilizes plural locking members which lock to the needle unit when the plunger is moved to the fully depressed position.

FIG. 37 shows an enlarged partial view of another non-limiting embodiment of a device. The device is similar to that of FIG. 1, except that it utilizes a sealing member 25" that utilizes a sealing member SM which can extend into the distal opening of the needle 32" so as to prevent medication from passing into the needle 32" when it is inserted into the distal end of the needle 32". The device also utilizes plural locking members LM which lock to a circumferential engaging projection EP of the needle unit 31" when the plunger is moved to the fully depressed position (indicated by arrow). Once locked to each other, the seal 25" and needle unit 30" retract into the plunger as a unit. The system shown in FIG. 37 can be utilized on any of the herein disclosed device embodiments.

Referring now to the drawings and to FIGS. 38-46 which shows another embodiment of an injection device 1000. The device 1000 is made of two main components or assemblies. One component is a syringe/plunger assembly SBA which includes a syringe barrel 1010 and a plunger 1020. Another component is a needle or needle-hub assembly NHA which includes a needle assembly body 1018, a biasing member 1040 and a needle member 1030. In embodiments, the device is a retractable hypodermic syringe. The syringe includes a generally elongate cylindrical barrel 1010 having a transverse flange 1011 arranged at a distal end of the barrel 1010. The barrel 1010 includes a main generally cylindrical section 1012. A proximal end of the barrel 1010 includes an increased diameter section 1013. A safety cap 1060 is removably disposed on a proximal end of the device 1000.

Figure 44:
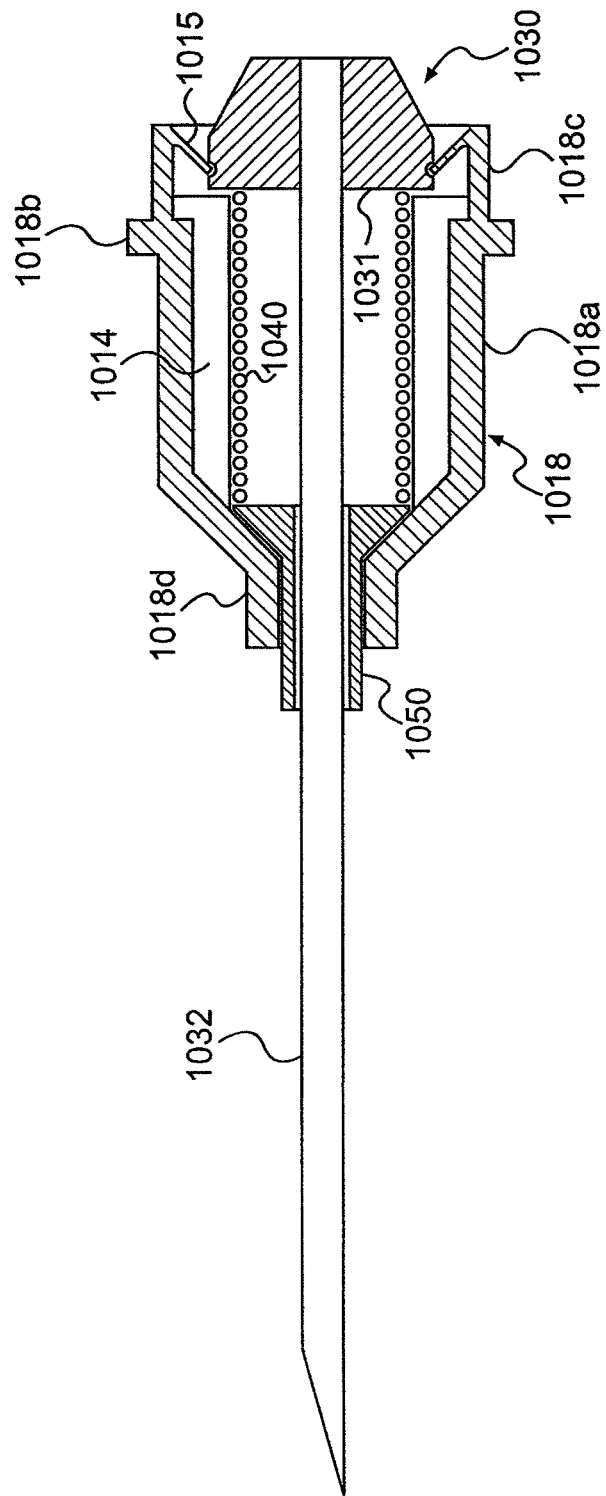
FIG. 44 shows an enlarged view of the needle assembly shown in FIG. 39.
Figure 45:
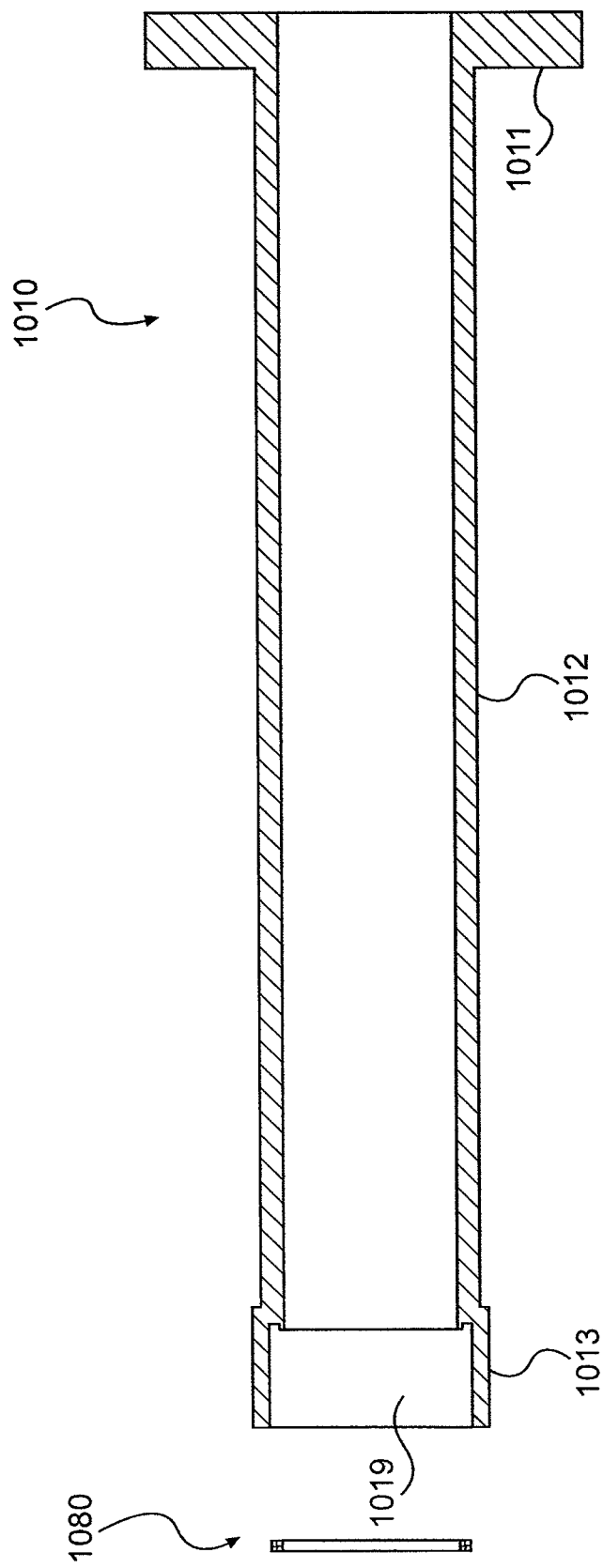
FIG. 45 shows an enlarged view of the barrel shown in FIG. 39. The seal is shown in an un-installed state.
Figure 46:
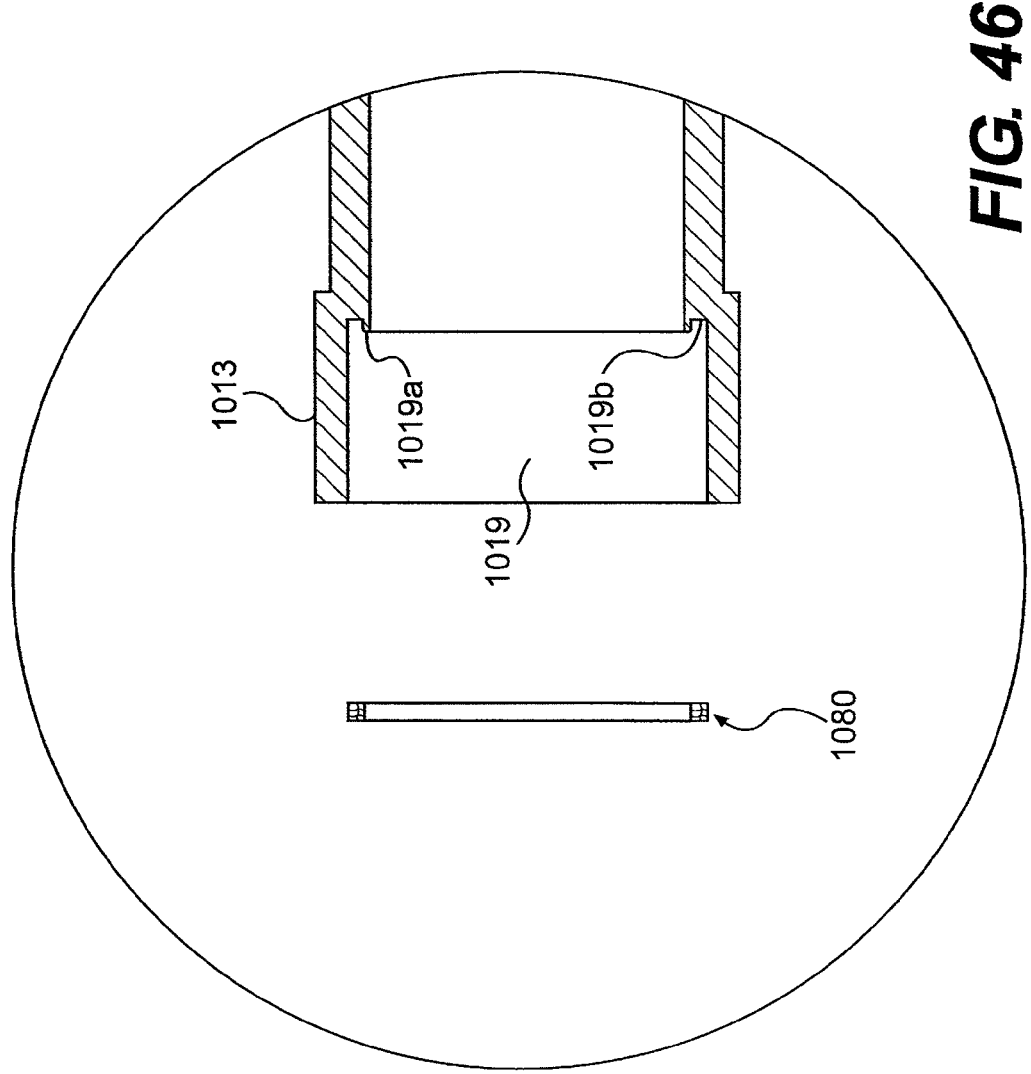
FIG. 46 shows an enlarged view of a front portion of FIG. 45.

A needle support 1030 has a hub portion 1031 that is substantially axially retained within a distal area of the body 1018 (see FIG. 44) and includes a rear end surface which can contact an inner seal 1025 of a plunger 1020, in a manner similar to that used in the embodiment of FIG. 1. The needle support 1030 also has a main needle portion 1032 that has a rear end fixed within a needle hub 1031 and a proximal end that is pointed or a puncturing end which extends out past the proximal end of the body 1018. A sealing guide member 1050 provides sealing between the needle 1032 and the proximal end 1018d of the body 1018, also allows the needle 1032 to slide into the syringe 1000 as will be described below. A biasing member having the form of a spring 1040 is arranged within the body 1018, and in the configuration shown in FIG. 44, is fully or nearly fully compressed. The spring 1040 biases the needle unit 1030 towards a distal end of the syringe 1000.

Figure 39:
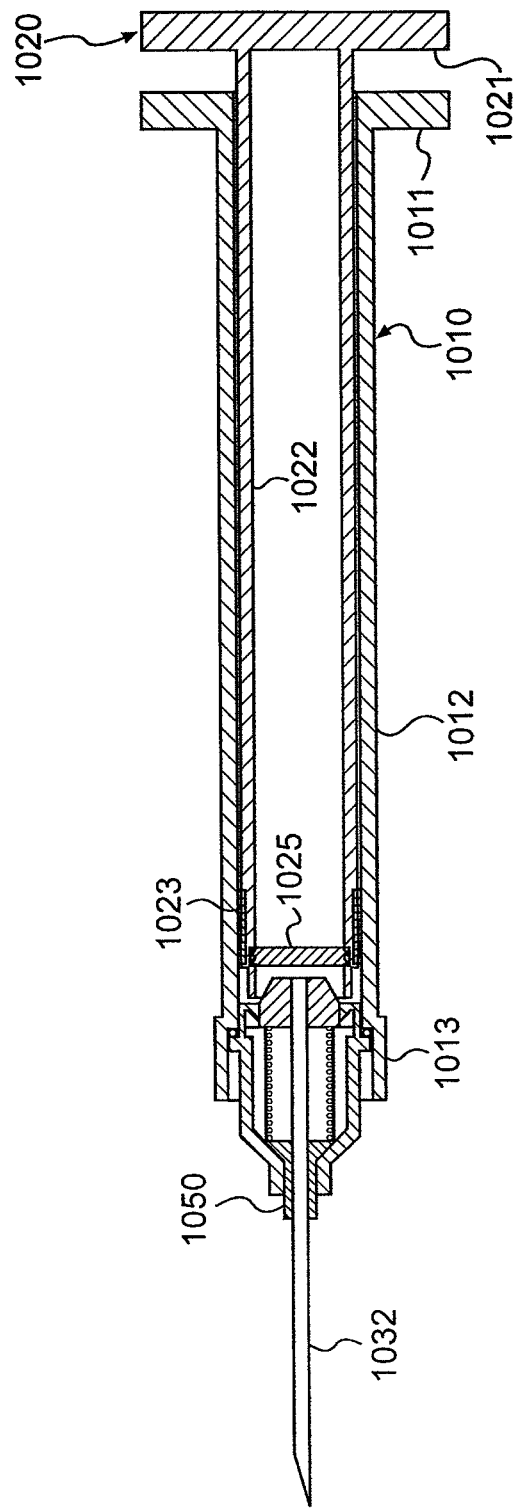
FIG. 39 shows the device of FIG. 38 when the needle assembly is fully installed on the barrel/plunger assembly and after the protective cover is removed. This is also a ready-to-use configuration.
Figure 40:
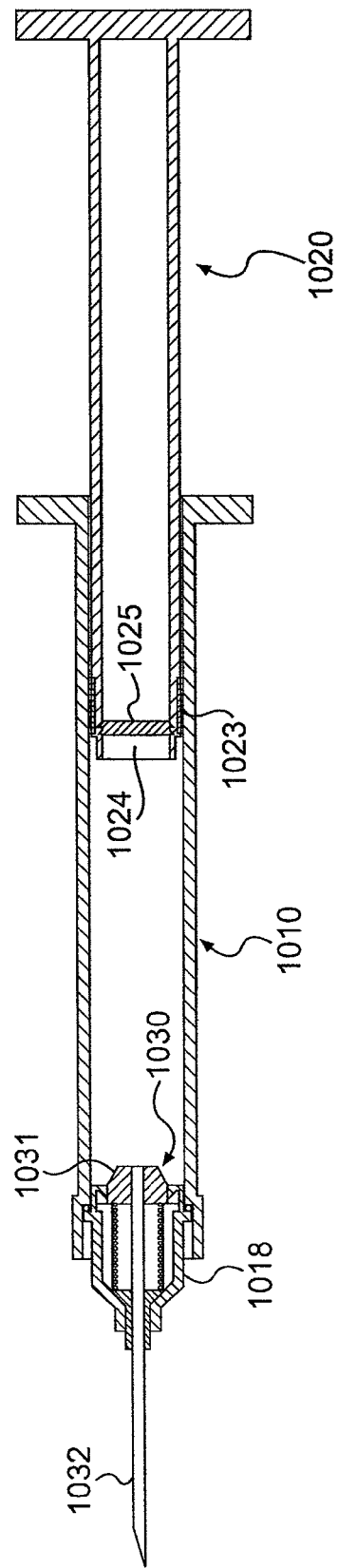
FIG. 40 shows the device of FIG. 39 after the plunger is withdrawn which would typically occur when a fluid or medicine is being force into or cause to enter the barrel through the needle.
Figure 41:
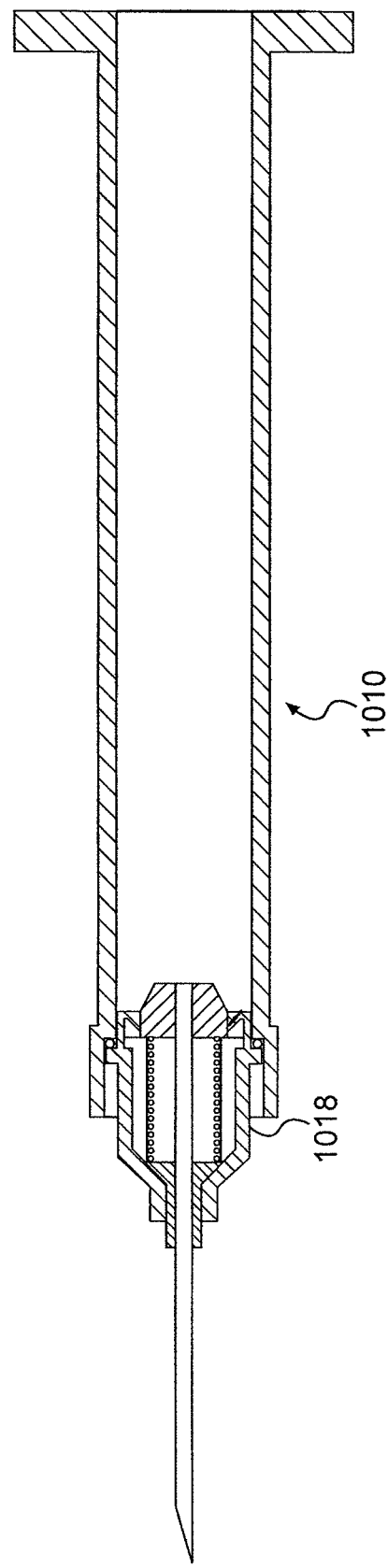
FIG. 41 shows the device of FIG. 39 with the plunger removed.

With reference to FIGS. 39 and 40, it can be seen that substantially arranged within the barrel 1010 of the syringe is movably disposed a plunger 1020. The plunger 1020, like the syringe body 1010, includes an end flange 1021 which is typically engaged by the thumb of the user while the transverse flange 1011 is engaged by the fingers of the user in order to enable the plunger 1020 to be forced into the barrel 1010 for the purpose of expelling the medicament from the barrel 1010 through the needle 1032. The plunger 1020 additionally includes a generally cylindrical space 1022 which is sized to receive therein the needle unit 1030 (similar to that shown in FIG. 5). A piston 1023 is arranged on a proximal end of the plunger 1010. The plunger 1020 also utilizes a proximal engaging end 1024 which is sized and configured to engage with deflectable retaining members 1015 (similar to that shown in FIGS. 6 and 7) when the plunger 1020 is fully depressed. An inner seal or sealing member 1025 is arranged within the plunger 1020. In a similar manner to that of FIGS. 6 and 7, the seal 1025 has frangible circumferential projections which are sized and configured to break and/or shear off when the plunger 1020 is depressed to the point where the seal 1025 contacts the hub 1031. Before the projections of the seal 1025 break, they provide sealing between the seal 1025 and the plunger 1020. This sealing ensures that no medication or fluid passes into the plunger space 1022 until the seal 1025 is broken.

Figure 42:
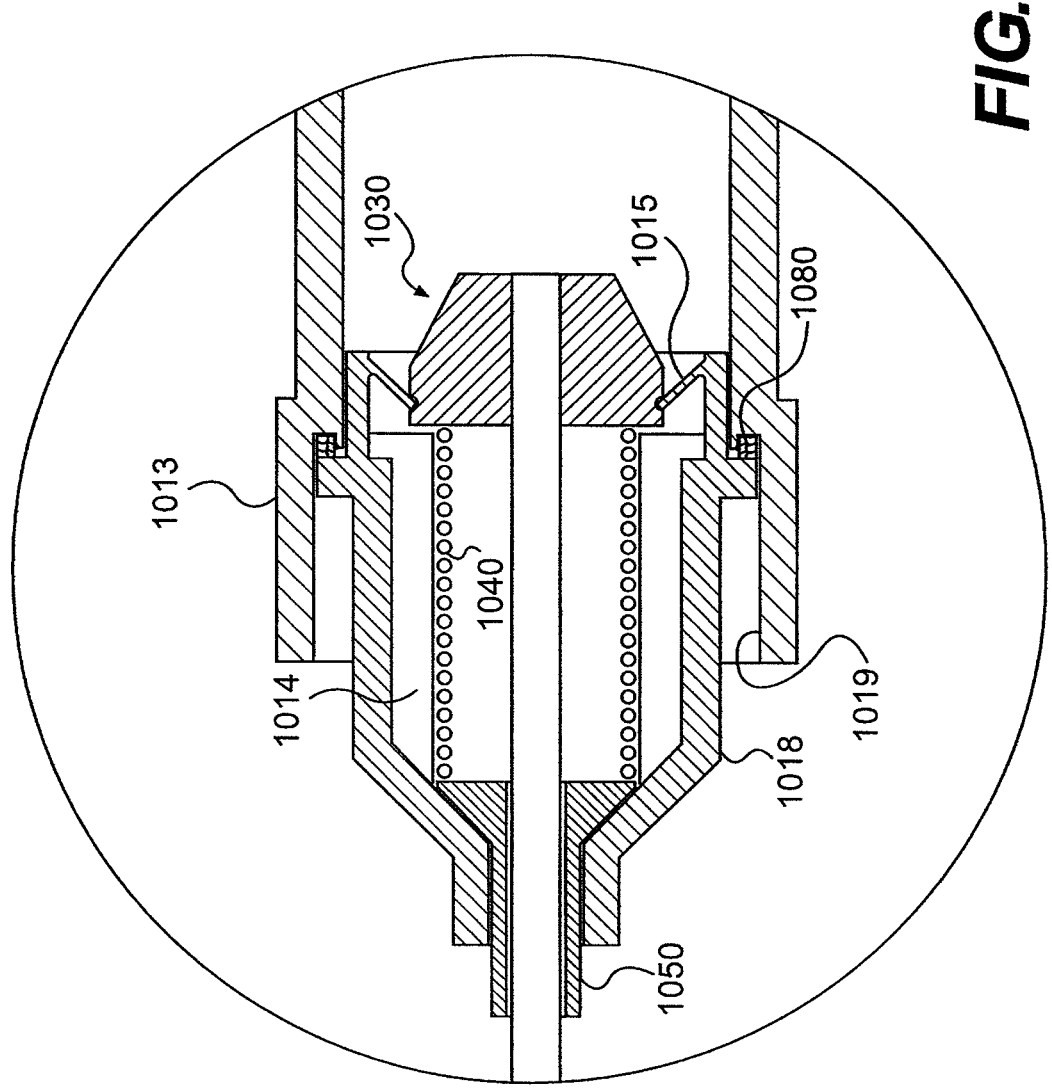
FIG. 42 shows an enlarged view of a front portion of FIG. 39.
Figure 43:
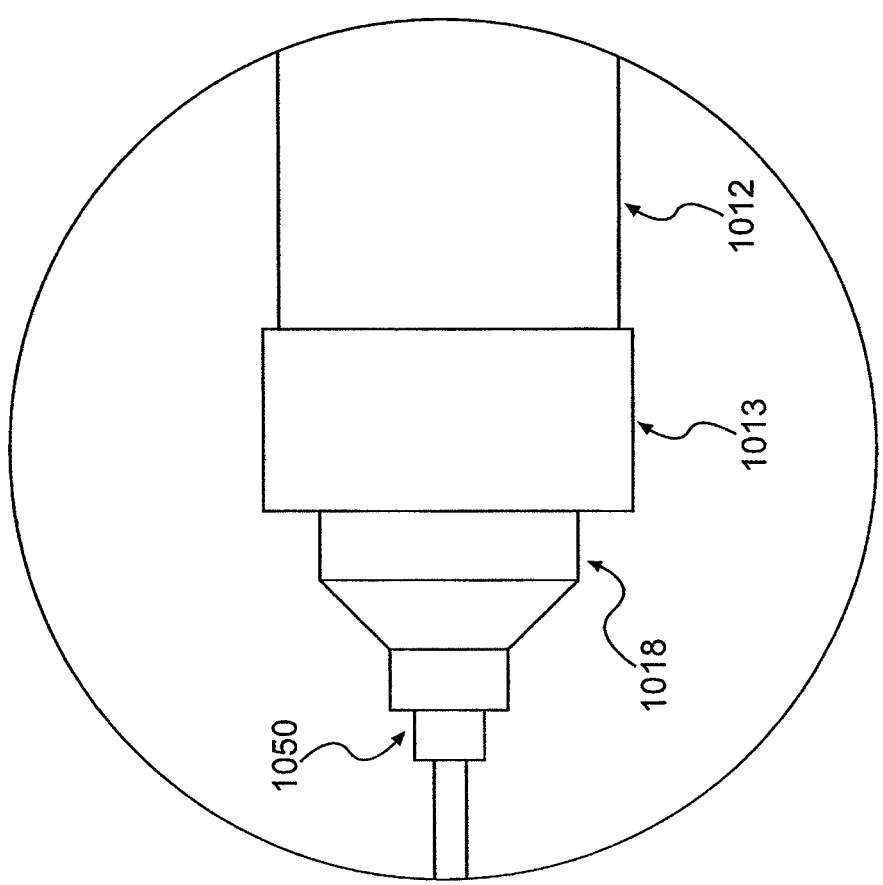
FIG. 43 shows a non cross-section view of FIG. 42.

As was the case in FIGS. 6 and 7, to unsure that the needle unit 1030 is prevented from moving forwards when the plunger 1020 is fully depressed, a plurality of stop projections or ribs 1014 are arranged within the body 1018 (see FIG. 42). However, unlike the embodiment of FIG. 1, because the instant embodiment provides for a separate and installable needle assembly, sealing is needed between the needle assembly and the barrel. Such sealing is provided by a sealing member 1080. As can be seen in FIGS. 42-46, the sealing member 1080 is sized and configured to slide within spacing 1019 and to seat in an annular groove 1019b defined by the surface 1019 and an annular projection 1019a. Sealing is ensured when the seal 1080 is caused to be compressed between flange 1018b and the groove 1019b. Non-limiting materials for the sealing member 1080 can include those typically used for sealing in syringes or other similar medical devices.

When the needle assembly is installed on the barrel 1010 as shown in FIG. 39, the generally cylindrical surface 1018c is sized and configured to frictionally engage with an inner cylindrical surface of the barrel 1010. In embodiments, both of these surfaces are slightly tapered to provide for better sealing. Also when the needle assembly is installed on the barrel 1010 as shown in FIG. 39, the flange 1018b arranged on main cylindrical surface 1018a of the body 1018 is sized and configured to frictionally engage with an inner slightly tapered surface 1019 of the barrel 1010. This ensures that the needle assembly is essentially wedged into the front end of the barrel 1010 and has the following functions: prevents leaking during injection, ensures that the needle assembly does not come out of frictional engagement with the barrel, and causes compression of the seal 1080.

Figure 38:
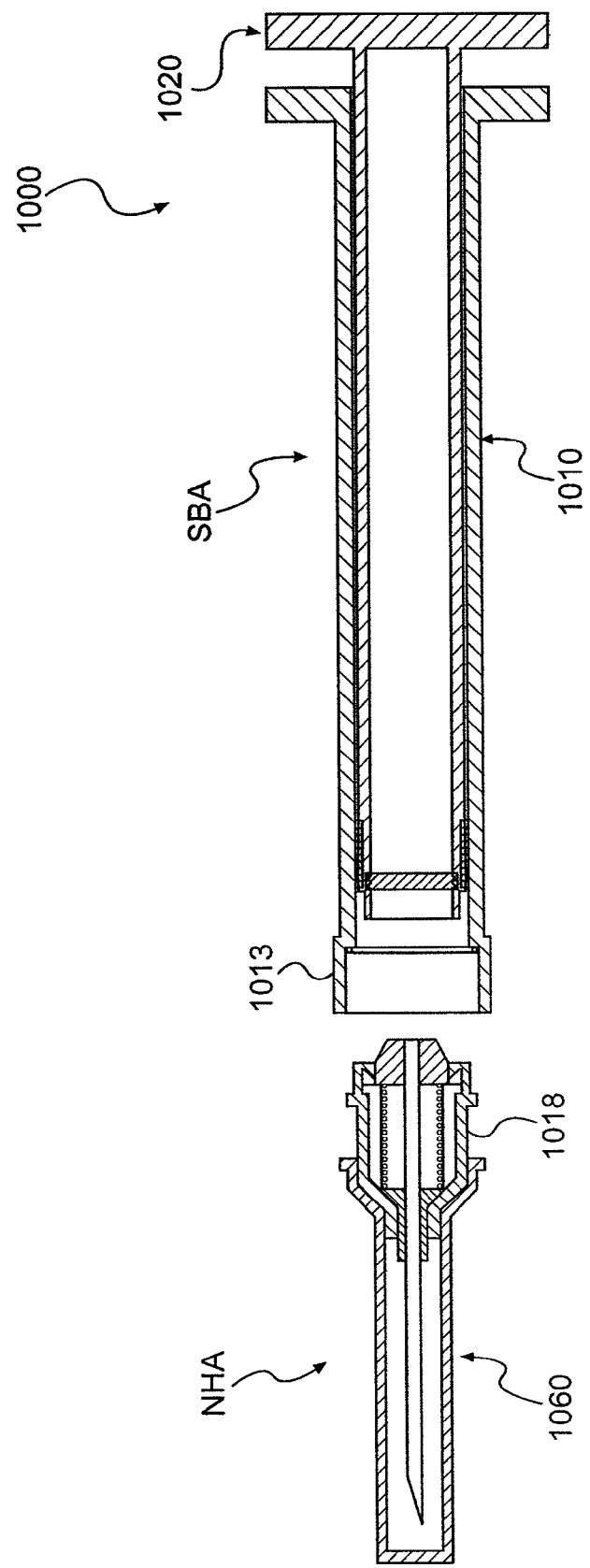
FIG. 38 shows a side cross section view of another embodiment of the invention. This embodiment is similar to that of FIG. 1 except that a needle assembly portion (on left side) of the injection device is separated from the barrel/plunger assembly (on right side). The injection end of the barrel is configured to receive different needle assemblies which have the same rear interface, i.e., that part which connects to the barrel/plunger assembly. In this embodiment, a user can select from a number of different needle sizes and types and install the desired needle assembly on the injection device barrel/plunger assembly prior to use. The needle assembly is frictionally engaged with the barrel when full installed and can be such that it is non removable once installed.

The operation of the device shown FIGS. 38-46 will now be described. Once the user obtains the desired needle assembly NHA and is ready to install it on a syringe body assembly SBA as shown in FIG. 38, he or she can grip the safety cap 1060 and install the needle assembly NHA on the syringe assembly SBA. Once assembled, the user can remove the safety cover 1060. The device so shown in FIG. 39 can now be used for, e.g., injection. This can occur when the user injects the needle 1032 into a medication container and withdraws the plunger 1020 as shown in FIG. 40. This causes medication fluid to fill the space in the body 1010 between the plunger piston 1023 and seal 1025 and the sealing member 1050. As this point, the user can move the plunger 1020 forwards slightly to remove any air in the syringe. The needle 1032 can then be injected into a surface, e.g., tissue. Then, the user will depress the plunger 1020 to cause the medication to pass out of the needle 1032. Once fully or nearly fully depressed, the proximal end 1024 of the plunger 1020 contacts the deflectable retaining members 1015 (see e.g., FIGS. 6 and 7) and causes them to deflect out of locking and/or retaining engagement with the hub 1031. Since engagement between the deflectable retaining members 1015 and the hub 1031 is the only mechanism which prevents the spring 1040 from moving the needle unit 1030 backwards, once this engagement is removed, the needle unit 1030 will be forced backwards by the spring 1040. Also, once fully or nearly fully depressed, the seal 1025 of the plunger 1020 contacts the rear surface of the hub 1031. Since the ribs 1014 prevent any forward movement of the hub 1031, contact between the seal 1025 and the hub 1031 causes the frangible sealing projections of the seal 1025 to shear or break. At this point, the spring 1040 automatically expands axially and pushes the needle unit 1030 and seal 1025 into the space 1022 disposed inside the plunger 1020. This action withdraws the needle 1032 into the syringe and renders the device 1000 unusable. The once-used device 1000 can then be safely disposed of without the user having to worry about being accidently pricked by the needle 1032, which is safely disposed inside the plunger 1020.

In embodiments, the engagement between the deflectable retaining members 1015 and the hub 1031 is removed or disengages prior to the sealing engagement between the seal 1025 and the plunger 1020. In other embodiments, the engagement between the deflectable retaining members 1015 and the hub 1031 is removed or disengages just prior to the sealing engagement between the seal 1025 and the plunger 1020. In embodiments, the engagement between the deflectable retaining members 1015 and the hub 1031 is not removed or disengaged until after the frangible sealing engagement between the seal 1025 and the plunger 1020 is broken. In embodiments, the engagement between the deflectable retaining members 1015 and the hub 1031 is not removed or disengaged until just after the frangible sealing engagement between the seal 1025 and the plunger 1020 is broken. In embodiments, the force required to unlock or remove the engagement between the deflectable retaining members 1015 and the hub 103s less than that required to break the sealing engagement between the seal 1025 and the plunger 1020. In embodiments, the force required to unlock or remove the engagement between the deflectable retaining members 1015 and the hub 1031 is greater than that required to break the sealing engagement between the seal 1025 and the plunger 1020. In embodiments, the force required to unlock or remove the engagement between the deflectable retaining members 1015 and the hub 1031 is substantially equal to that required to break the sealing engagement between the seal 1025 and the plunger 1020. In embodiments, a noise is produced (providing an auditory signal to the user) when the engagement between the deflectable retaining members 1015 and the hub 1031 is removed. In embodiments, a noise is produced (providing an auditory signal to the user) when the sealing engagement between the seal 1025 and the plunger 1020 is broken. In embodiments, a visual indication is produced (providing a visual signal to the user) when the engagement between the deflectable retaining members 1015 and the hub 1031 is removed. In embodiments, a visual indication is produced (providing a visual signal to the user) when the sealing engagement between the seal 1025 and the plunger 1020 is broken. Such visual indicators can be facilitated by making the plunger 1020 and body 1010 substantially transparent and/or translucent.

Figure 47:
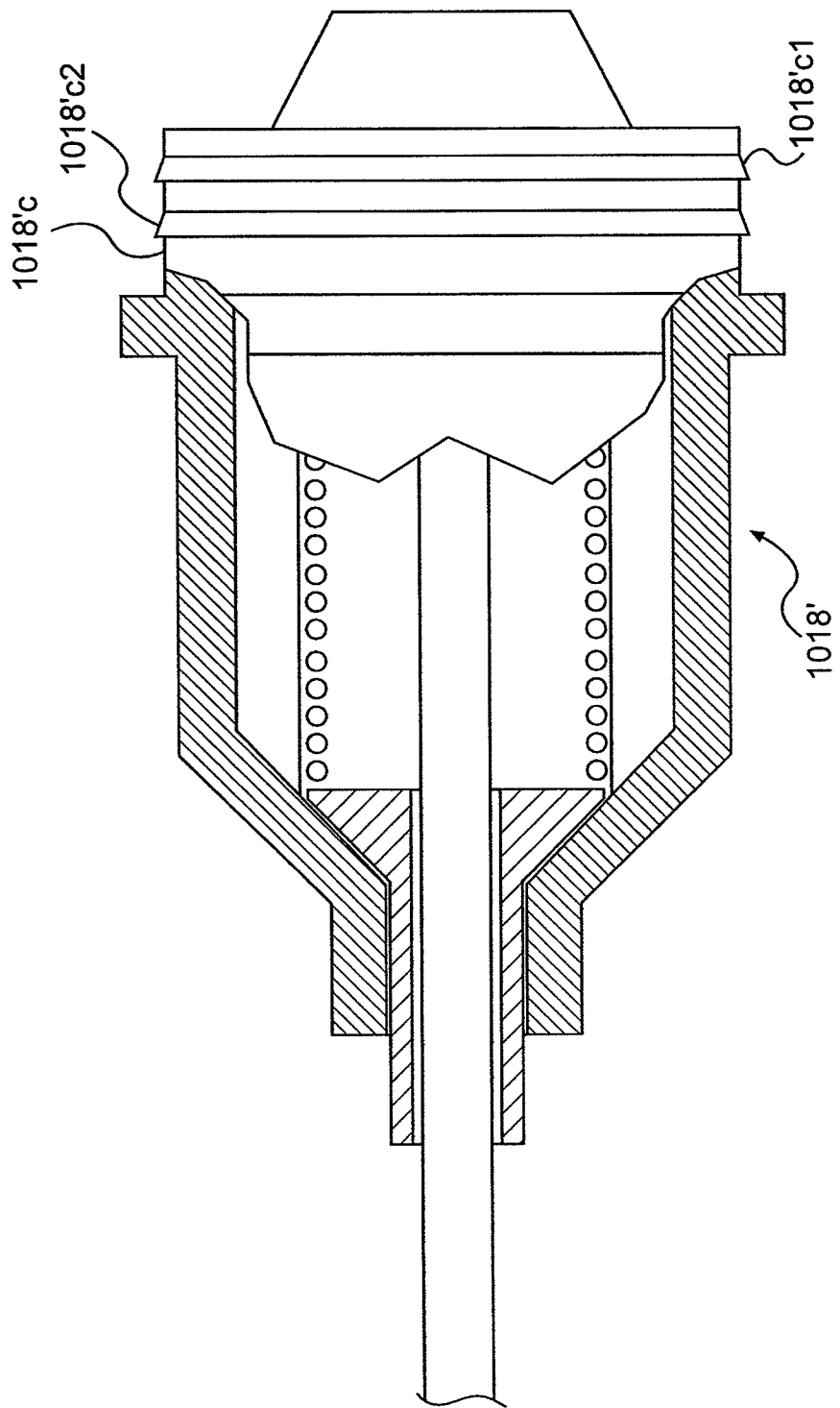
FIG. 47 shows an enlarged view of an optional needle assembly which can be used in accordance with the invention. This embodiment is similar to that of FIG. 44 except that a rear cylindrical surface includes plural frictional sealing projections to provide additional sealing and frictional retention with the barrel.

FIG. 47 shows an enlarged view of an optional needle assembly which can be used in accordance with the invention. This embodiment is similar to that of FIG. 44 except that a rear cylindrical surface 1018'*c* of the body 1018' includes plural frictional sealing projections 1018'*c*1 and 1018'*c*2 to provide additional sealing and frictional retention with the barrel 1010. This sealing/frictional engagement can be used with any of the embodiments shown or described with reference to FIGS. 38-63.

Figure 48:
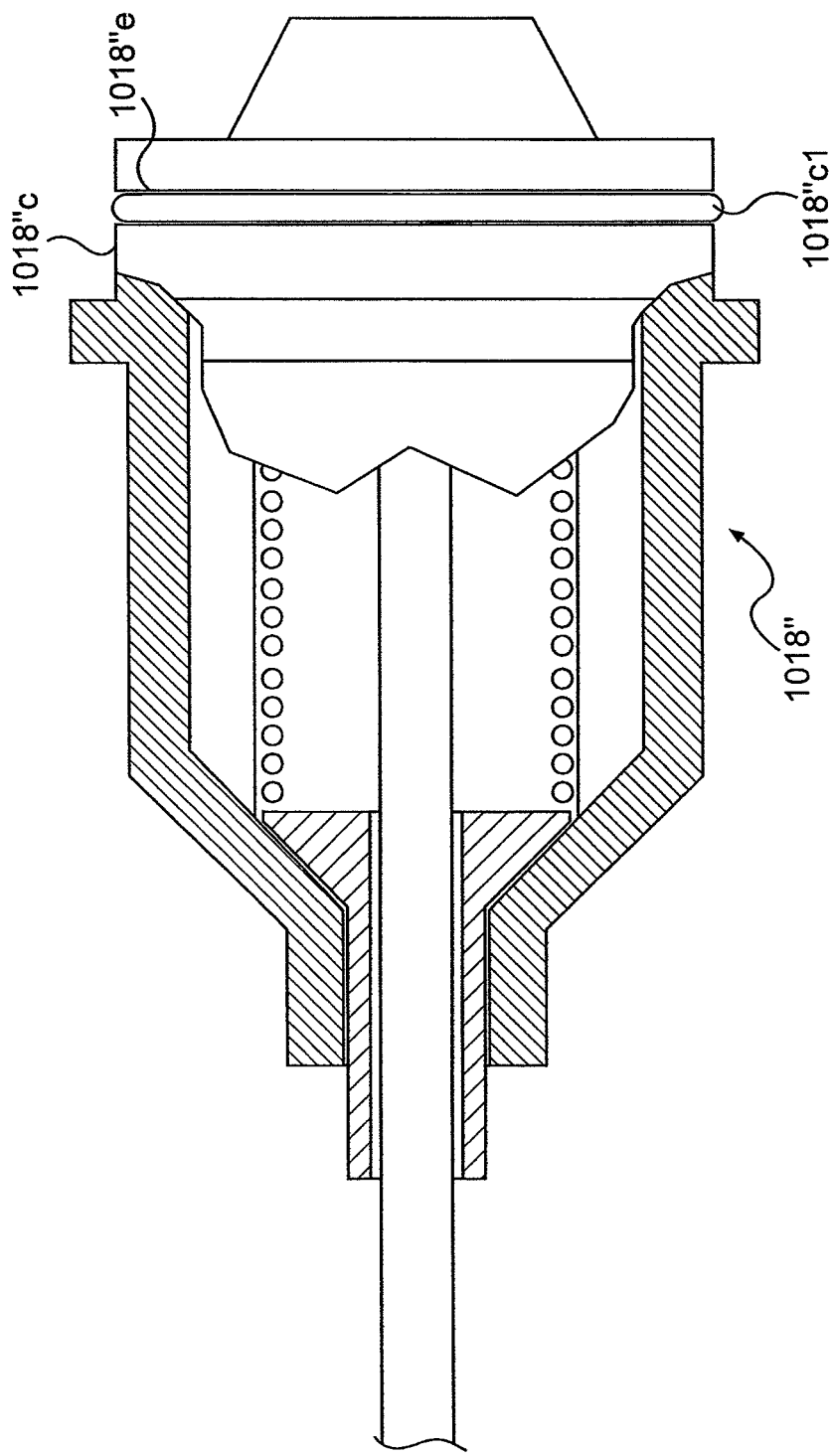
FIGS. 48 and 49 show enlarged views of another optional needle assembly which can be used in accordance with the invention. This embodiment is similar to that of FIG. 44 except that a rear cylindrical surface includes a groove and an installable seal member to provide additional sealing and frictional retention with the barrel.
Figure 49:
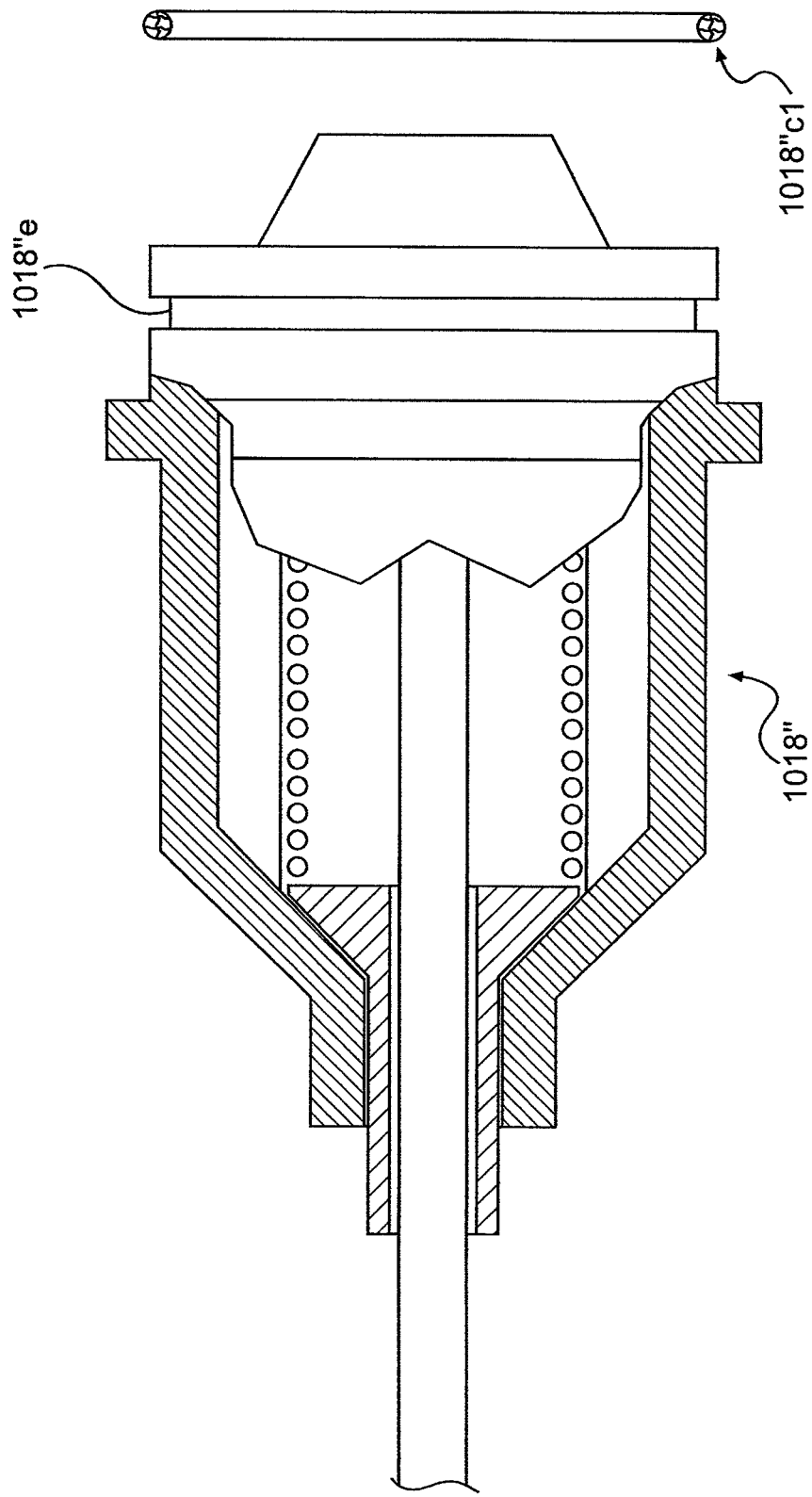

FIGS. 48 and 49 show enlarged views of another optional needle assembly which can be used in accordance with the invention. This embodiment is similar to that of FIG. 44 except that a rear cylindrical surface 1018"*c* includes a groove 1018"*e* and an installable seal member or O-ring 1018"*c*1 to provide additional sealing and frictional retention with the barrel. In FIG. 48, the seal member 1018"*c*1 is shown in the groove 1018"*e*. In FIG. 49, the seal member 1018"*c*1 is shown removed from the groove 1018"*e*. This sealing/frictional engagement can be used with any of the embodiments shown or described with reference to FIGS. 38-63.

Figure 50:
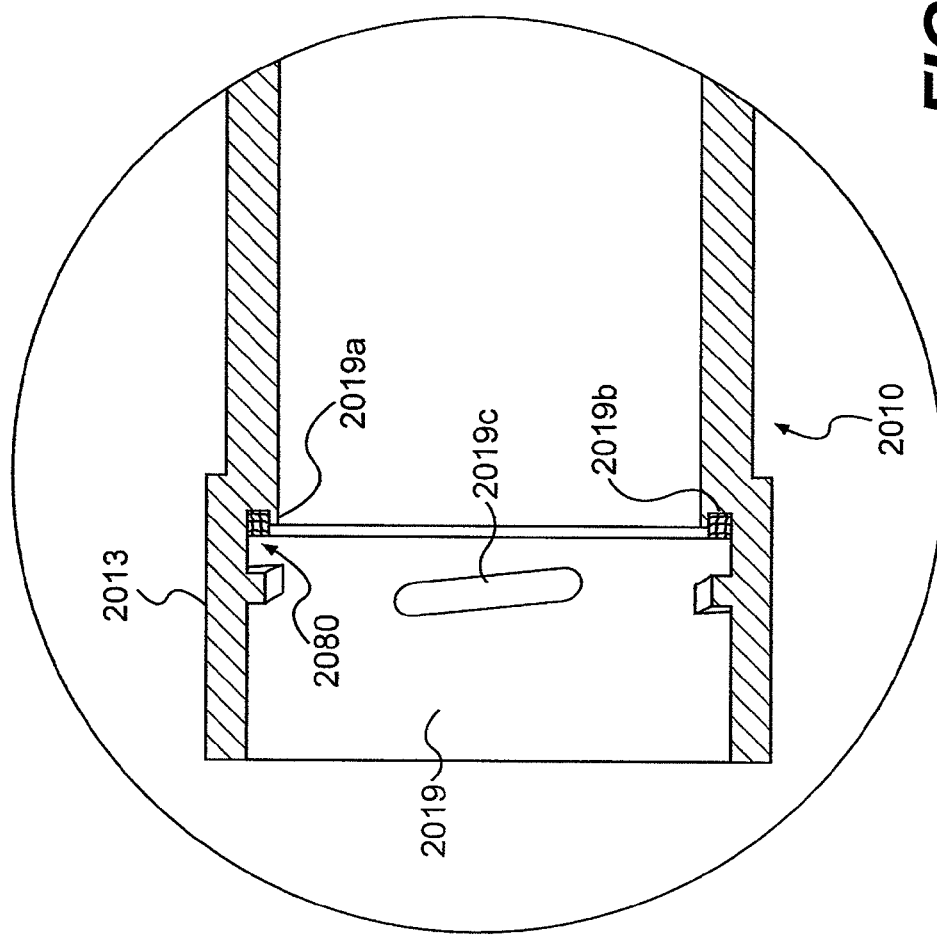
FIG. 50 shows an enlarged view of an optional configuration for a front portion of the barrel in accordance with the invention. This embodiment is similar to that of FIG. 46 except that partial or interrupted thread(s) are used to axially retain the needle assembly on the barrel.
Figure 51:
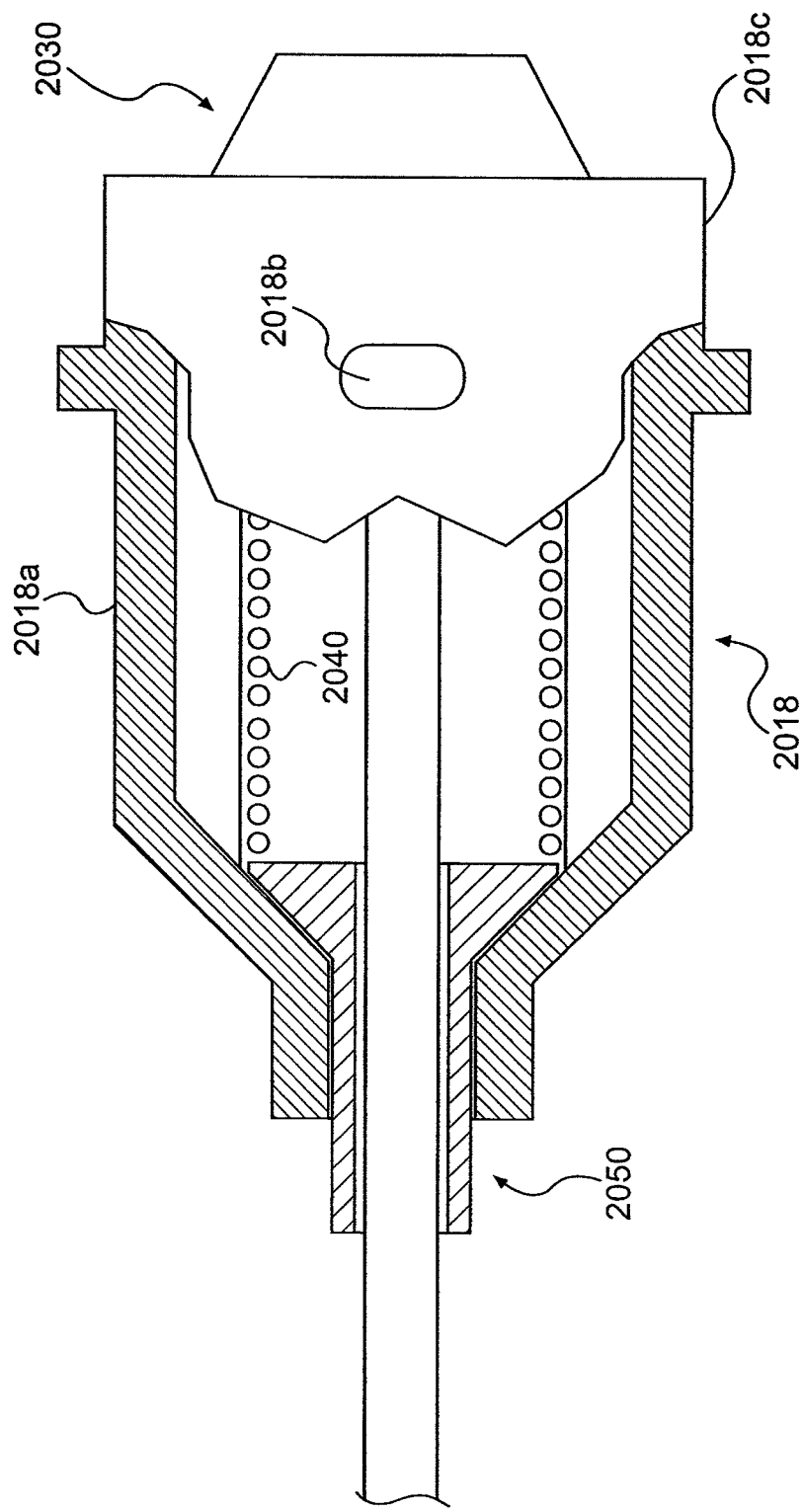
FIG. 51 shows an enlarged view of an optional configuration for a needle assembly in accordance with the invention. This embodiment is similar to that of FIG. 44 except that partial or interrupted projections are used (which can threadably engage with the interrupted threads of FIG. 50) to axially retain the needle assembly on the barrel.

FIGS. 50 and 51 show an optional configuration for a front portion of the barrel and the needle assembly in accordance with the invention. This embodiment is similar to that of FIG. 46 except that partial or interrupted thread(s) 2019*c* are used to axially retain the needle assembly body 2018 on the barrel 2010. The arrangement of FIGS. 50 and 51 functions as follows. When the user wishes to install the needle assembly shown in FIG. 51 in the open end 2013 of the barrel 2010 shown in FIG. 50, he or she slides the needle assembly into the opening 2019 and causes the projections 2018*b* to threadably engage with the partial threads 2019*c*. This forces the projections 2018*b* into contact with the seal member 2080. As with previous embodiments, the seal 2080 is seated in a groove 2019*b* defined by an annular projection 2019*a* and the needle assembly has a body 2018, a sealing member 2050, a spring 2040, an outer generally cylindrical surface 2018*a* having the projections 2018*b*, as well as a distal generally cylindrical surface 2018*c* and a needle unit 2030 which can retract into the plunger (not shown). Moreover, because the projections 2018*b* are spaced apart (and is not a continuous flange), sealing will not be ensured by the sealing member 2080. As such, it is desirable to use sealing in at least one other location such as those shown in, e.g., FIGS. 47, 48, 62 and 64. The arrangement of FIGS. 50 and 51 provides for a quick or easy threaded connection between the needle assembly and the syringe/plunger assembly. This provides for quick connect (and also disconnect—although not necessarily desirable) of the same merely by rotating the needle assembly relative to the barrel by a small angle of rotation.

Figure 52:
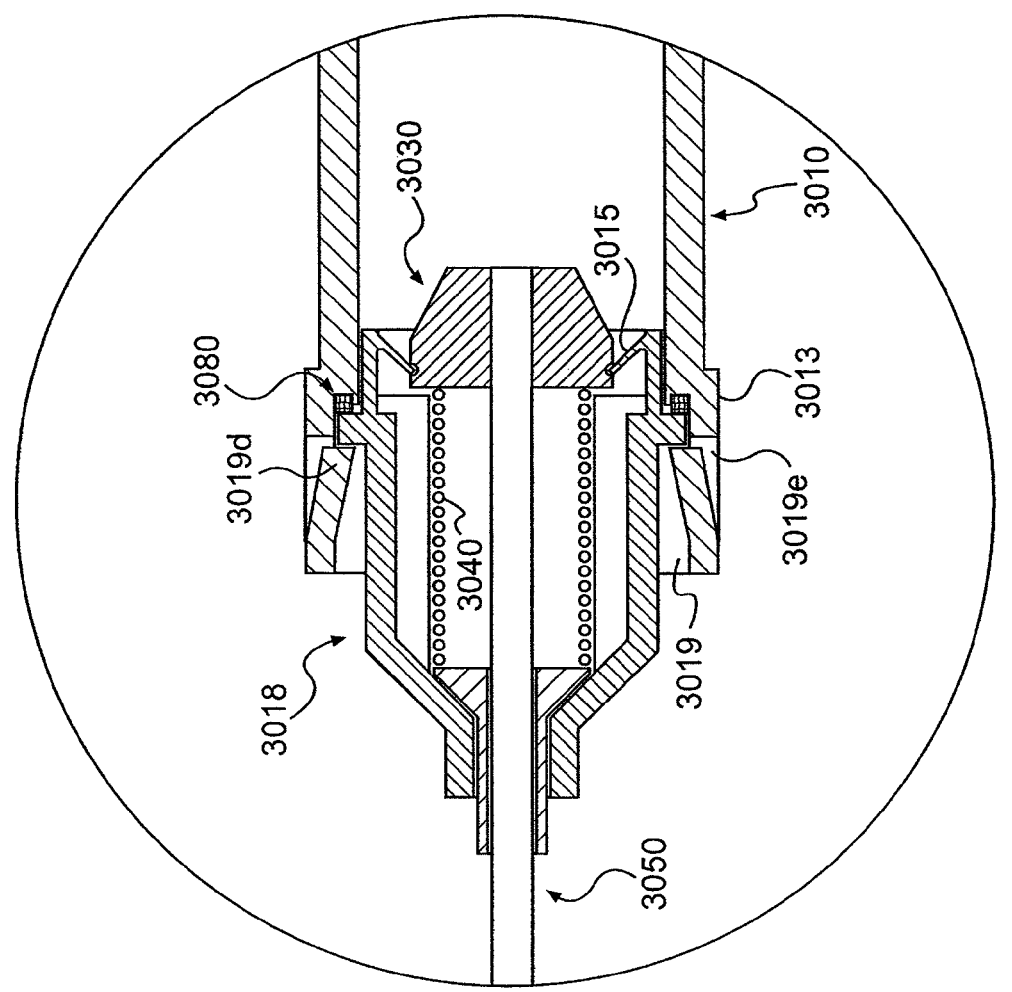
FIG. 52 shows an enlarged view of an optional configuration for a front portion of the injection device in accordance with the invention. This embodiment is similar to that of FIG. 42 except that deflectable locking projections are used to axially and non-removably retain the needle assembly on the barrel.
Figure 53:
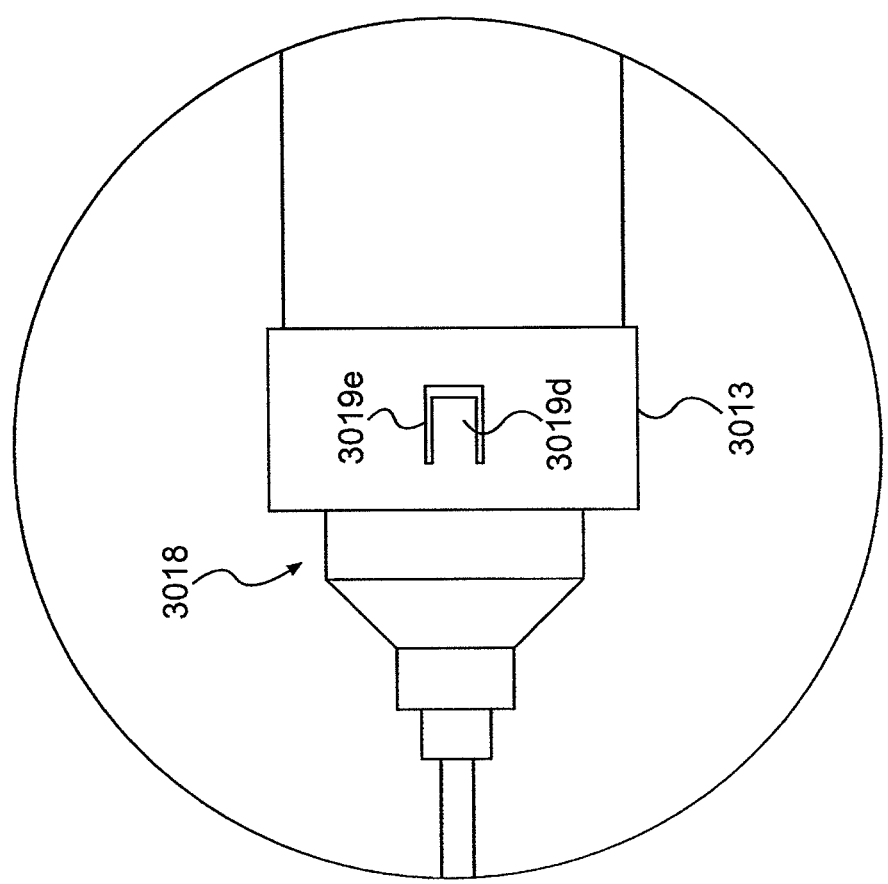
FIG. 53 shows a non cross-section view of FIG. 52.
Figure 54:
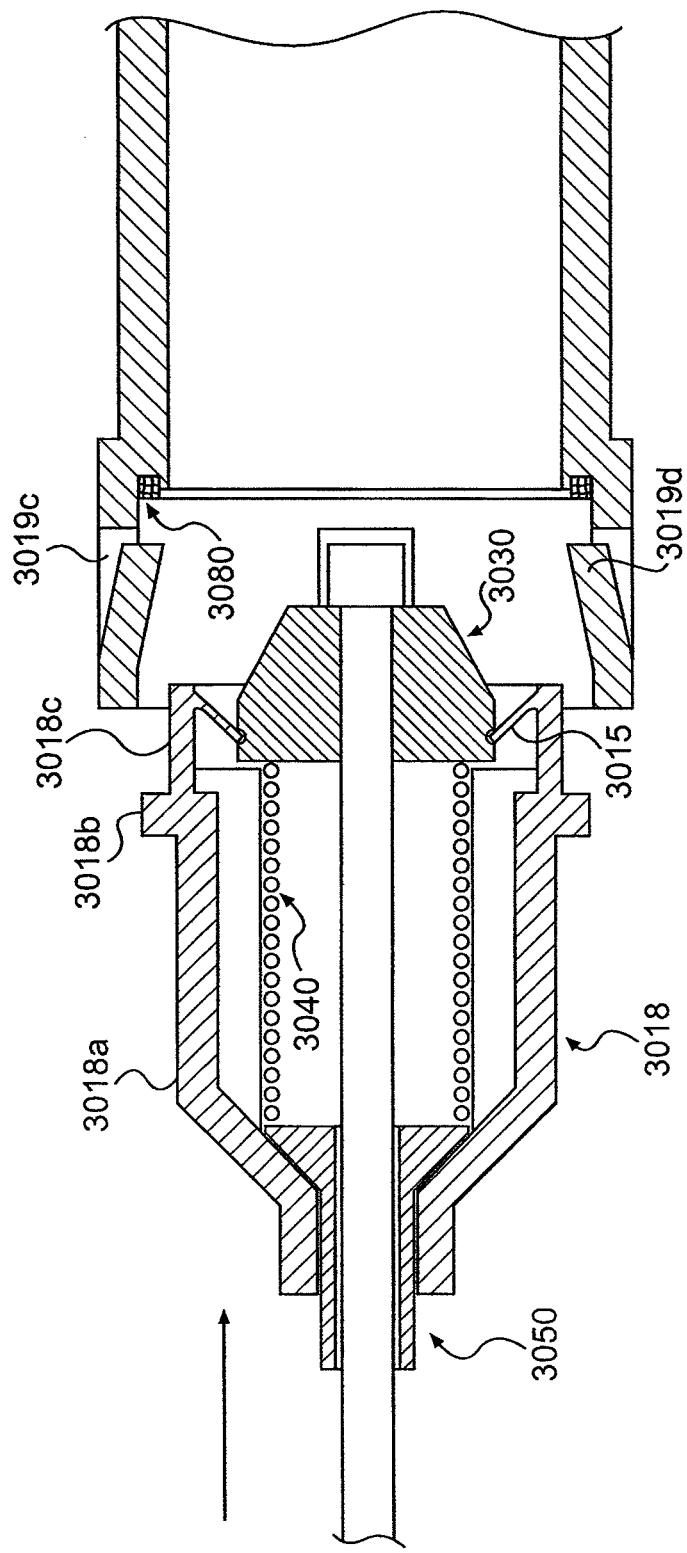
FIG. 54 shows how the needle assembly can be slid (along axial direction of arrow) into the barrel in order to form the device of FIG. 52.

FIGS. 52-54 show an optional configuration for a front portion of the injection device in accordance with the invention. This embodiment is similar to that of FIG. 42 except that deflectable locking projections 3019*d* are used to axially and non-removably retain the needle assembly body 3018 on the barrel 3010. The arrangement of FIGS. 52-54 functions as follows. When the user wishes to install the needle assembly in the manner shown in FIG. 54 in the open end 3013 of the barrel 3010, he or she slides the needle assembly into the opening 3019 and causes the projections 3019*d* to deflect outwardly until the flange 3018*b* contacts the seal 3080. The projections 3019*d* then automatically deflect back inwardly to an original or a locking position shown in FIG. 52. The projections 3018*d* then function to axially press the flange 3018*b* into contact with the seal member 3080. Each projection 3019*d* moves within a space or opening 3019*e* formed in the section 3013 of the barrel 3010. As with previous embodiments, the needle assembly has a body 3018, a sealing member 3050, a spring 3040, an outer generally cylindrical surface 3018*a* having the flange 3018*b*, as well as a distal generally cylindrical surface 3018*c* and a needle unit 3030 which can retract into the plunger (not shown). Sealing will be ensured by the sealing member 3080. However, it may also be desirable to use additional sealing in at least one other location such as those shown in, e.g., FIGS. 47, 48, 62 and 64. The arrangement of FIGS. 52-54 provides for a quick or easy slide-on or snap connection between the needle assembly and the syringe/plunger assembly. This provides for quick non-releasable automatic connection (by preventing disconnection) of the same merely by sliding the needle assembly into the barrel by a predetermined amount—while also ensuring or enabling proper sealing at the same time. The sound, i.e., a click sound, provided by the projections 3019*d* assuming the original locked position shown in FIG. 52 (after being deflected outwardly) provides an indication to the user that the needle assembly is fully and properly installed and that sealing of the same is ensured.

Figure 55:
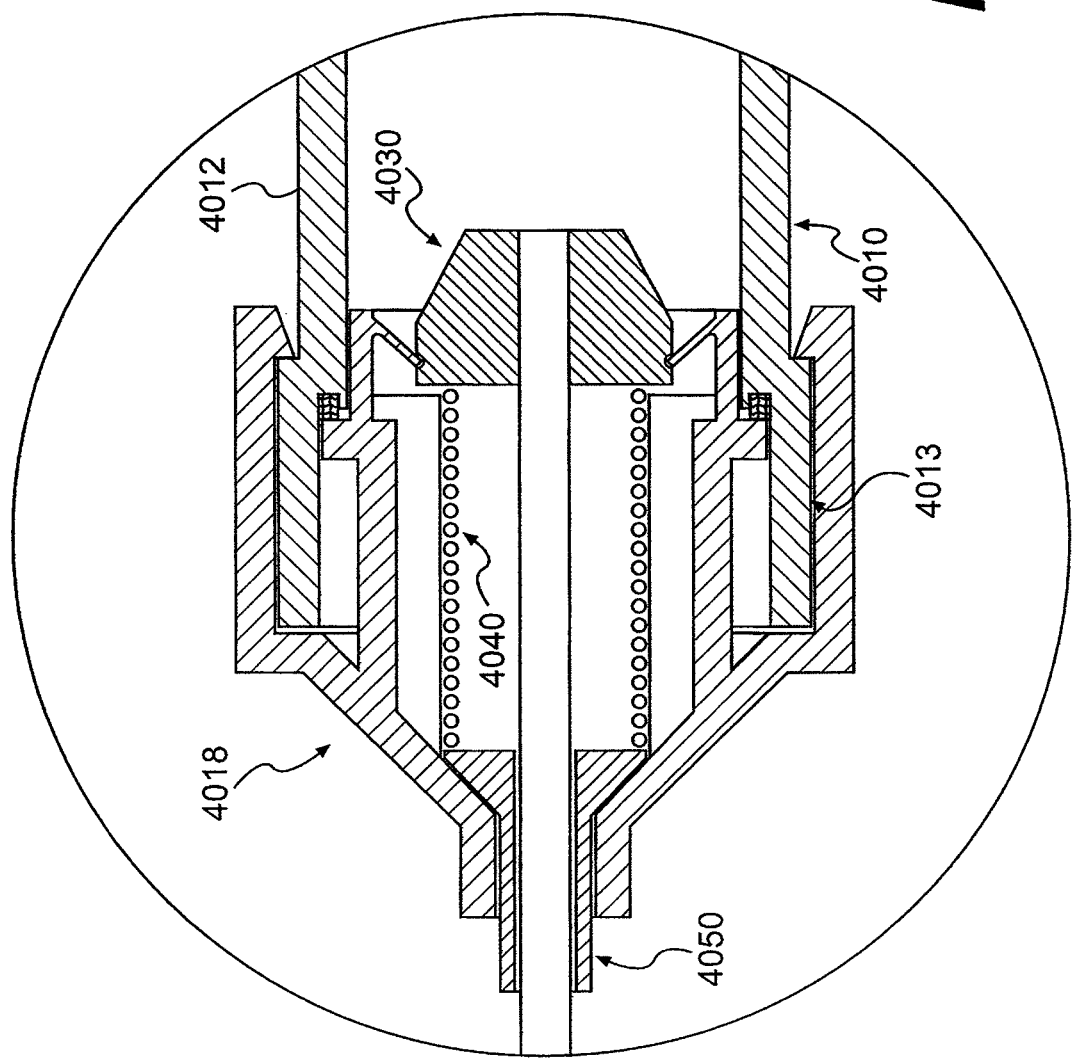
FIG. 55 shows an enlarged view of an optional configuration for a front portion of the injection device in accordance with the invention. This embodiment is similar to that of FIG. 42 except that an outer locking sleeve having deflectable locking projections is used to axially and non-removably retain the needle assembly on the barrel. This embodiment also provides the user with a visual indication that the needle assembly is fully and properly installed on the barrel.
Figure 56:
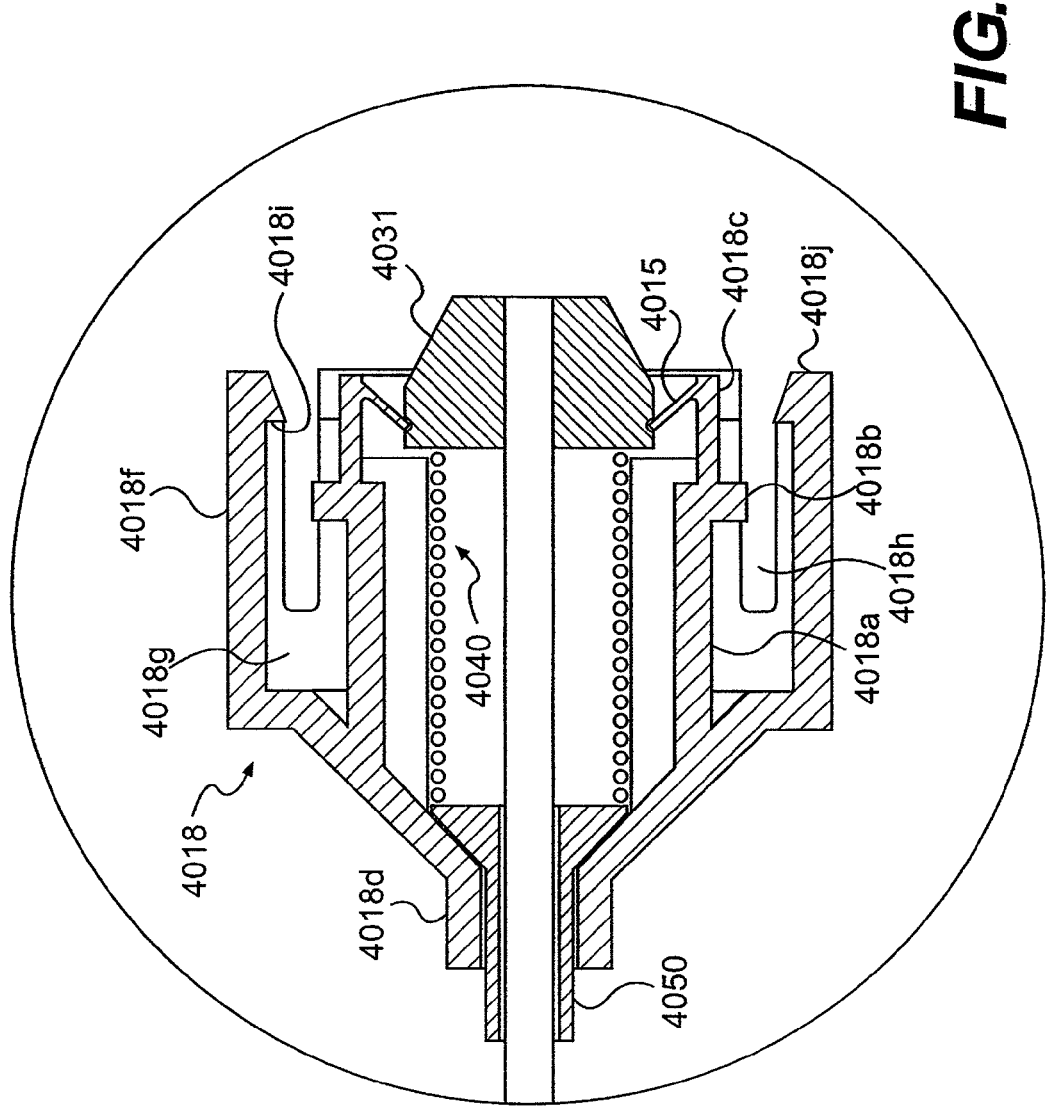
FIG. 56 shows the needle assembly used in the device of FIG. 55.
Figure 57:
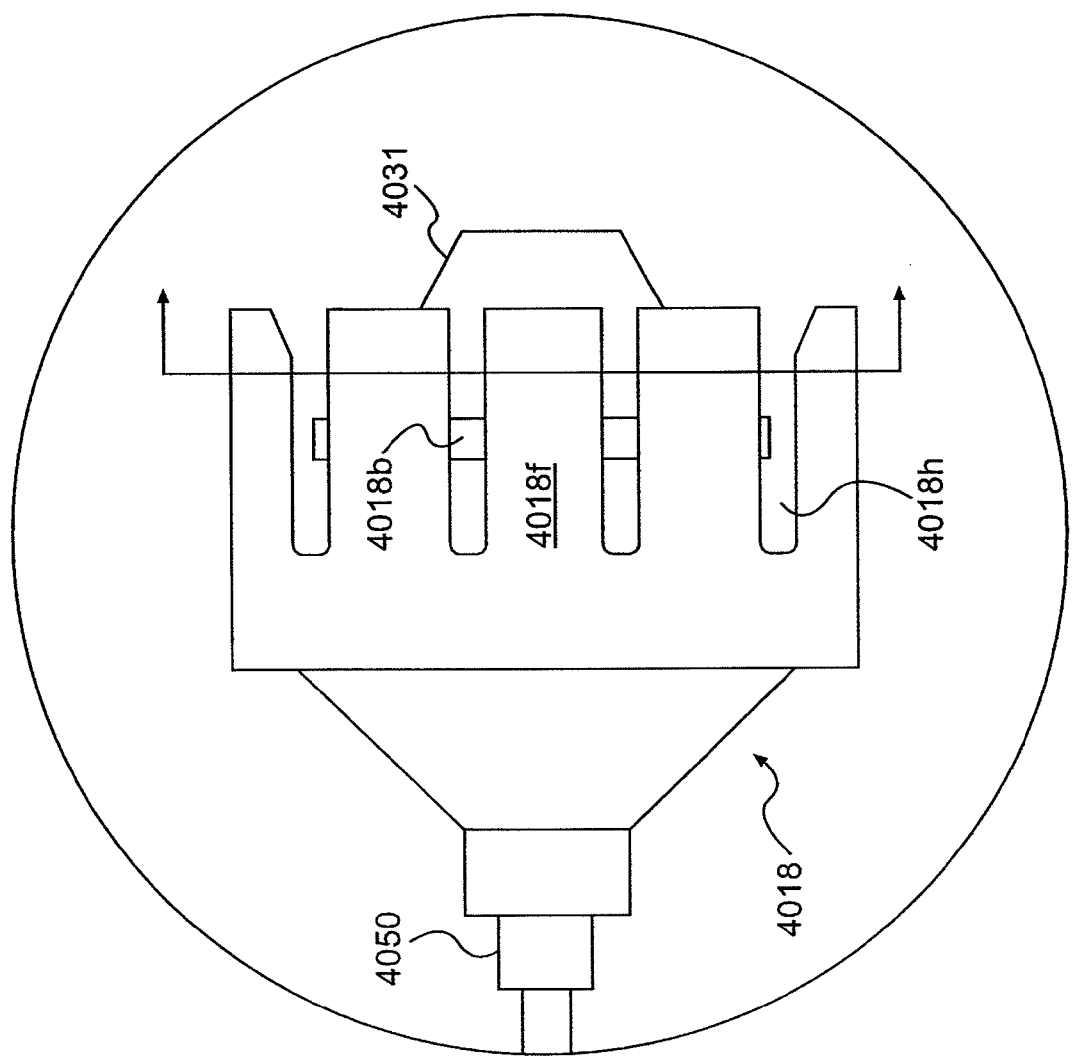
FIG. 57 shows a non cross-section view of FIG. 56.
Figure 58:
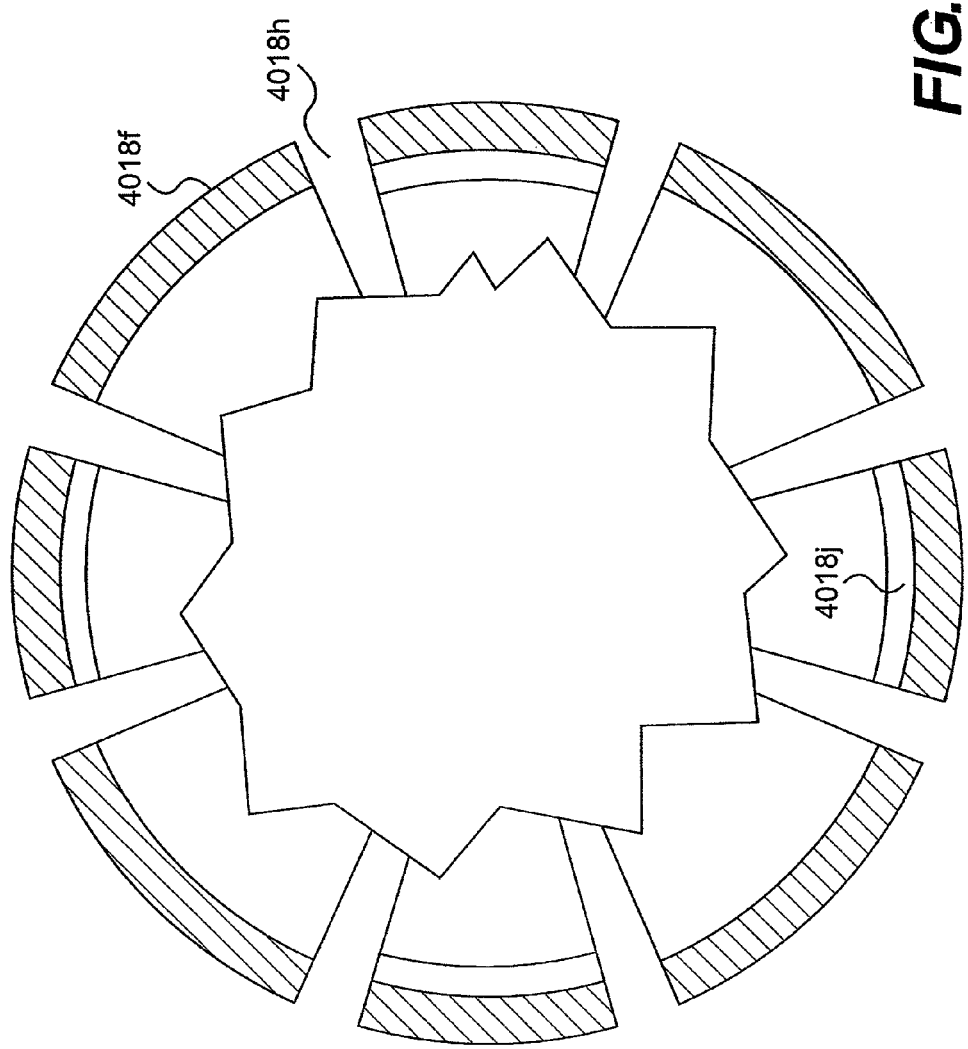
FIG. 58 shows a cross-section view of FIG. 57.

FIGS. 55-58 show another optional configuration for a front portion of the injection device in accordance with the invention. This embodiment is similar to that of FIG. 42 except that an outer locking sleeve 4018*f* is used to axially and non-removably retain the needle assembly body 4018 on the barrel 4010. The arrangement of FIGS. 55-58 functions as follows. When the user wishes to install the needle assembly in the open end 4013 of the barrel 4010, he or she slides the needle assembly onto the open end 4013 and causes the members 4018*j* having projections 4018*i* to deflect outwardly until the projections 40181 lock to the annular shoulder between section 4013 and section 4012 as shown in FIG. 55. The members 4018*j* automatically deflect back inwardly to an original or a locking position shown in FIG. 55 when the needle assembly is fully installed. The projections 4018*i* thus ensure that the flange 4018*b* is pressed into contact with the seal member 4080. Each member 4018*j* can deflect because of slots or openings 4018*h*. An annular space 4018*g* thus receives therein the end 4013 of the barrel 4010. As with previous embodiments, the needle assembly has a body 4018, a sealing member 4050, a spring 4040, a proximal hub section 4018*d*, an outer generally cylindrical surface 4018*a* having the flange 4018*b*, as well as a distal generally cylindrical surface 4018*c* and a needle unit 4030 which can retract into the plunger (not shown). The needle unit 4030 is retained in position by the deflectable members 4015 and includes a needle hub 4031 and a needle. Sealing will be ensured by the sealing member 4080. However, it may also be desirable to use additional sealing in at least one other location such as those shown in, e.g., FIGS. 47, 48, 62 and 64. The arrangement of FIGS. 55-58 provides for a quick or easy slide-on or snap connection between the needle assembly and the syringe/plunger assembly. This provides for quick non-releasable automatic connection (by preventing disconnection) of the same merely by sliding the needle assembly onto the barrel by a predetermined amount—while also ensuring or enabling proper sealing at the same time. The sound, i.e., a click sound, and the visual image of the fingers 4018*j* assuming a generally cylindrical position as provided by the projections 4018*i* assuming the original locked position shown in FIG. 55 (after being deflected outwardly) provides both a visual and audible indication to the user that the needle assembly is fully and properly installed and that sealing of the same is ensured.

Figure 59:
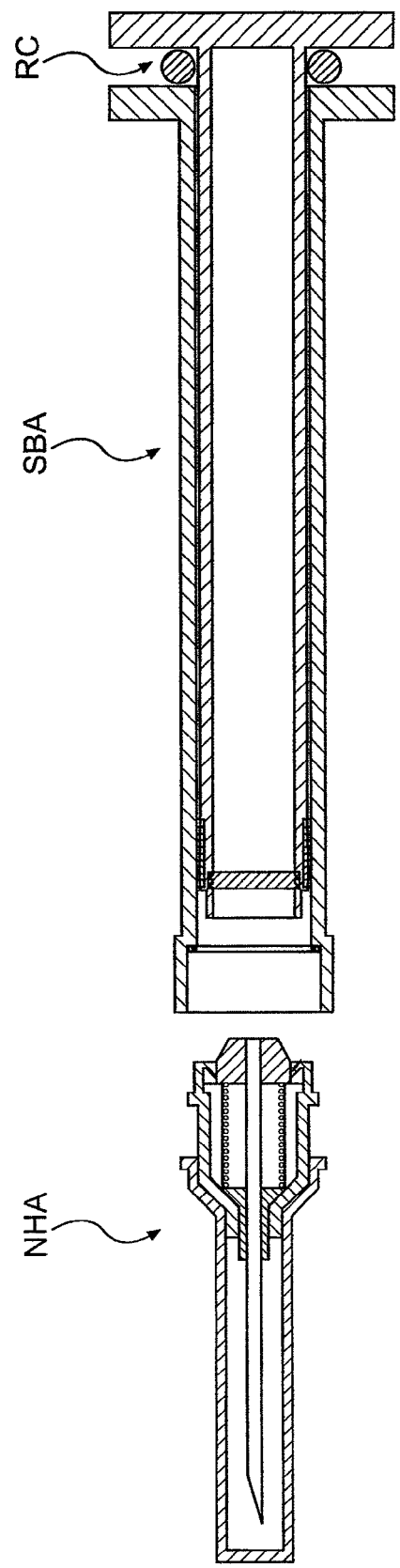
FIG. 59 shows a side cross section view of another embodiment of the invention. This embodiment is similar to that of FIG. 38 except that the device additionally utilizes a removable retaining clip to ensure that the plunger is not fully depressed before or during installation of the needle assembly on the barrel/plunger assembly. Preferably, the user removes the retaining clip just prior to use of the injection device.

FIG. 59 shows another embodiment of the invention. This embodiment is similar to that of FIG. 38 except that the device additionally utilizes a removable retaining clip RC to ensure that the plunger is not fully depressed before or during installation of the needle assembly NHA on the barrel/plunger assembly SBA. Preferably, the user removes the retaining clip RC after installation of the needle assembly NHA on the barrel/plunger assembly SBA and just prior to use of the injection device. The removable retaining clip RC can also be used on any of the other herein disclosed embodiments.

Figure 60:
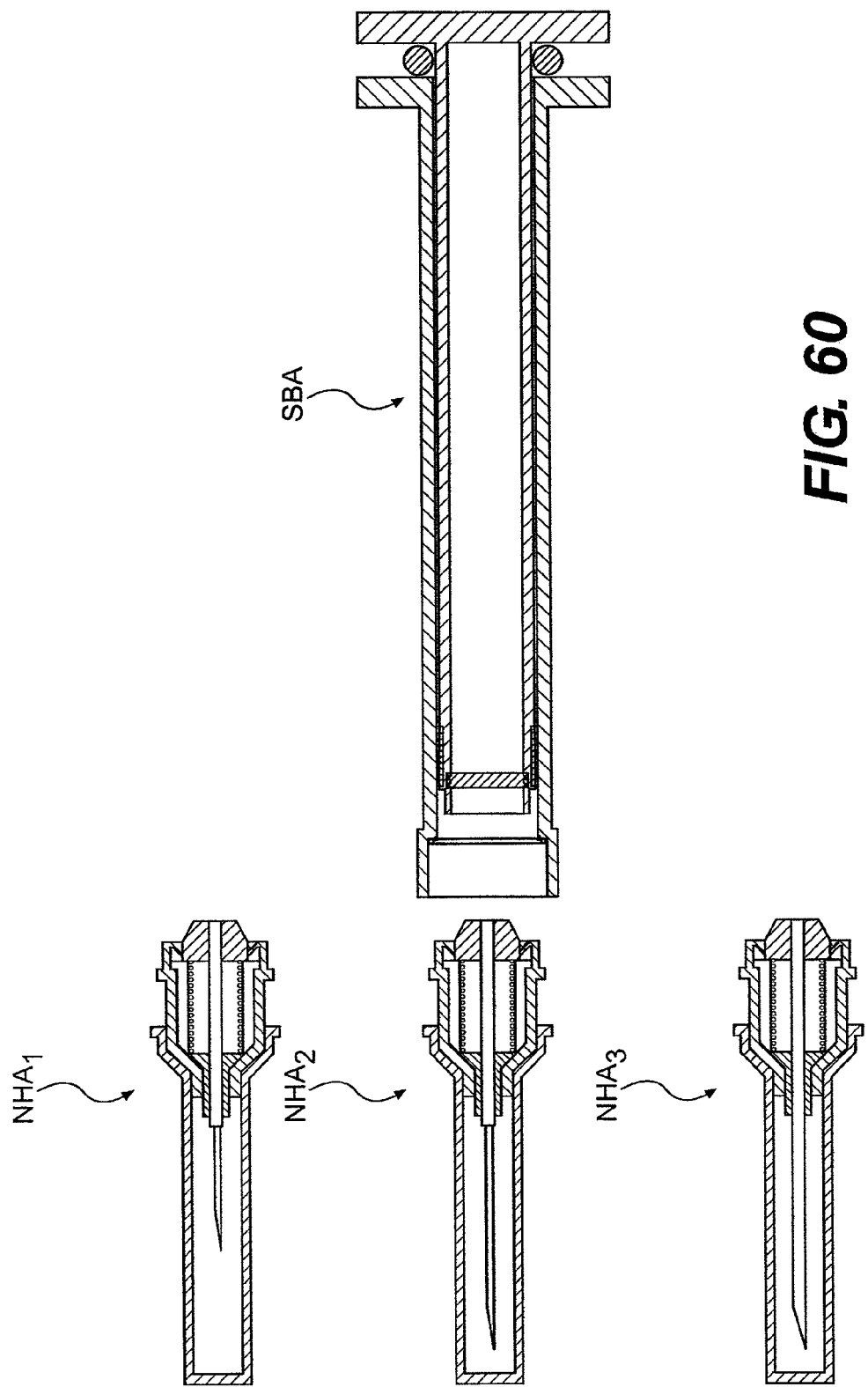
FIG. 60 shows a side cross section view of another embodiment of the invention. This embodiment is similar to that of FIG. 59 except that a number of different needle assembles (i.e., assemblies with different needle lengths and diameters) are shown from which the user can select and install on the barrel/plunger assembly.

FIG. 60 shows an embodiment similar to that of FIG. 59 and utilizing a number of different needle assembles NHA1, NHA2 and NHA3 (i.e., assemblies with different needle lengths and diameters). The user can select one of the needle assemblies and install the selected one on the barrel/plunger assembly SBA. Each needle assembly has the same back-end configuration which allows it to be mounted on a common barrel/plunger assembly SBA. As is apparent from FIG. 60, needle assembly NHA1 utilizes a smaller diameter and shorter length needle than that of needle assembly NHA3. Needle assembly NHA2 utilizes a smaller diameter needle than that of needle assembly NHA3. Preferably, each herein disclosed embodiment allows a user to select from a number of different needle assemblies for mounting on a common barrel/plunger assembly SBA.

Figure 61:
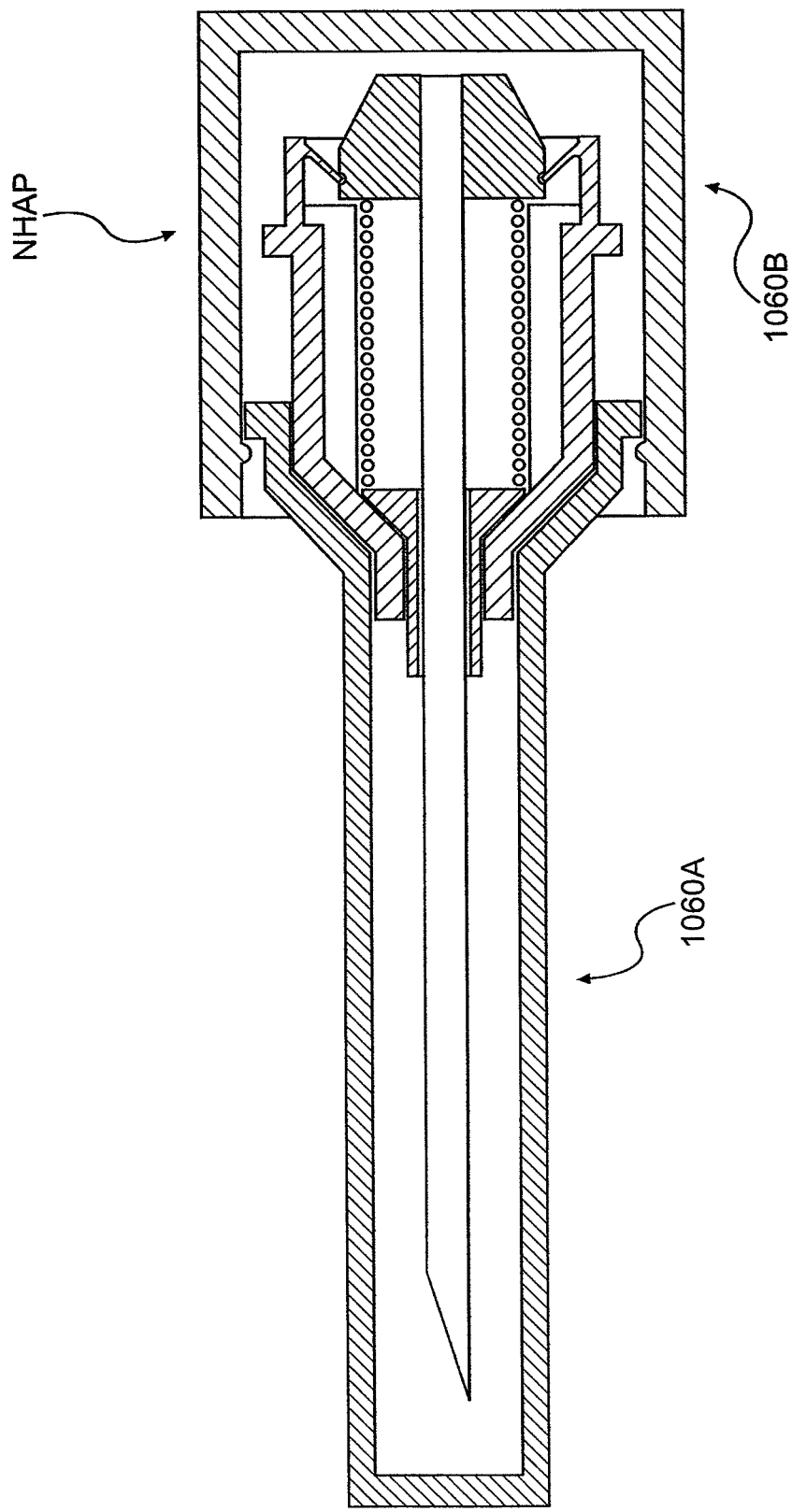
FIG. 61 shows a side cross section view of a packaged needle assembly in accordance with one non-limiting embodiment of the invention. The package utilizes a needle outer cover and a rear cover. When the user wishes to install the needle assembly, she first removes the rear cover from the front cover, installs the needle assembly on the barrel/plunger assembly, and then removes the needle cover.

FIG. 61 shows a packaged needle assembly NHAP in accordance with one non-limiting embodiment of the invention. The package utilizes a needle outer cover 1060A and a rear cover 1060B. When the user wishes to install the needle assembly, he or she first removes the rear cover 1060B from the front cover 1060A, installs the needle assembly on the barrel/plunger assembly, and then removes the needle cover 1060A.

FIGS. 62 and 63 show another optional configuration for a front portion of the injection device in accordance with the invention. This embodiment is similar to that of FIG. 42 except that tapered locking projections LP are used to axially and non-removably retain the needle assembly on the barrel 5010. The projections LP axially retain the flange 5018*b* of the body 5018 and force it against the seal 5080. The needle assembly, like those previously described, includes a spring 5040, deflectable retaining members 5015, and a needle unit 5030. Furthermore, an additional real seal member ASM is arranged in a retaining groove RG and is used to provide additional sealing between the body 5018 and the barrel 5010. In FIG. 62, the additional seal ASM is shown in an installed position. In FIG. 63, the additional seal ASM is shown in a non-installed position. This additional sealing arrangement can be used with any of the embodiments shown or described with reference to FIGS. 38-61.

Figure 64:
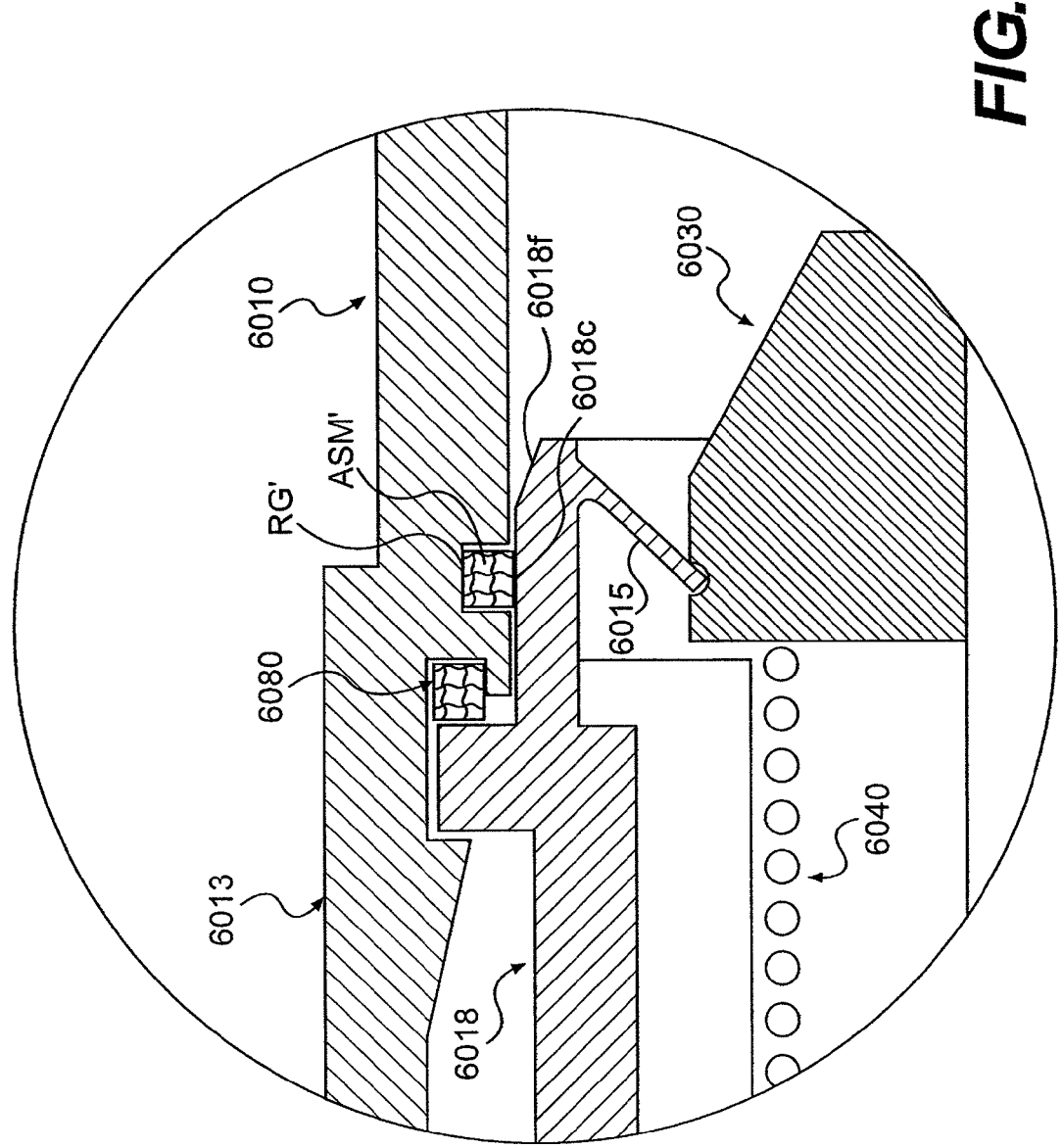
FIG. 64 shows enlarged view of an optional configuration for a front portion of the injection device in accordance with the invention. This embodiment is similar to that of FIG. 62 except that the additional real seal member is arranged in a groove formed in the barrel and the distal generally cylindrical surface of the needle assembly utilizes a tapered section to facilitate insertion of the needle assembly in the barrel.

FIG. 64 shows another optional configuration for a front portion of the injection device in accordance with the invention. This embodiment is similar to that of FIG. 62 except that tapered section 6018*f* is used to help guide the body 6018 into the barrel 6010 during installation and especially into the secondary seal ASM'. The projections axially retain the flange of the body 6018 and force it against the seal 6080. The needle assembly, like those previously described, includes a spring 6040, deflectable retaining members 6015, and a needle unit 6030. Furthermore, the additional real seal member ASM' is arranged in a retaining groove RG' formed in the barrel 6010 and is used to provide additional sealing between the generally cylindrical surface 6018*c* of the body 6018 and the barrel 6010. This additional sealing arrangement can be used with any of the embodiments shown or described with reference to FIGS. 38-61.

FIGS. 65-68 and 83 show a front portion of the injection device in accordance with another embodiment of the invention. This embodiment is similar to that of FIG. 52 except that except that the needle unit is separated into two main components. A first component or assembly 7030A utilizes a needle hub portion 7031 which is axially retained in a front section of the syringe via deflectable members 7015 and has a universal or standard receiving interface SI. The standard receiving interface SI can be of any type such as a luer lock or luer-lok. In this way, the same or different needles (or types of needles) having or sharing a common and/or the same connecting interface can be coupled to the syringe. A second component or assembly 7030B utilizes a needle N and a standard interface hub NH which can be sealingly connected to the standard receiving interface SI of the first component 7030A. A sealing ring 7050 (see FIG. 83) is utilized to seal the member 7031 to the body 7018. A spring 7040 biases the member 7031 towards a retracted position. A needle assembly body 7018 is axially and sealingly retained on the barrel 7010 via members 7019*d* and seal 7080 as in the arrangement of FIG. 52 and functions as follows. When the user wishes to install the needle assembly 7030A/7018 (with or without the needle member 7030B) in the manner similar to that shown in FIG. 54 in the open end 7019 of the barrel 7010, he or she slides the needle assembly into the opening 7019 and causes the projections 7019*d* to deflect outwardly until the flange 7018*b* contacts the seal 7080. The projections 7019*d* then automatically deflect back inwardly to an original or a locking position shown in FIG. 65. The projections 7018*d* then function to axially press the flange 7018*b* into contact with the seal member 7080. Each projection 7019*d* moves within a space or opening formed in the section 7013 of the barrel 7010. As with previous embodiments, the needle assembly has a body 7018, a sealing member 7050, a spring 7040, an outer generally cylindrical surface having the flange 7018*b*, further includes a two-component a needle unit 7030A and 7030B which can retract (see FIG. 68) into the plunger (not shown). The arrangement of FIGS. 65-68 and 83 provides for a quick or easy slide-on or snap connection between the needle assembly and the syringe/plunger assembly and also allows different size or types of needle members 7030B having a common interface to be connected to the syringe. This provides for quick non-releasable automatic connection (by preventing disconnection) of the body 7018 merely by sliding the needle assembly into the barrel by a predetermined amount—while also ensuring or enabling proper sealing at the same time. The sound, i.e., a click sound, provided by the projections 7019*d* assuming the original locked position shown in FIG. 65 (after being deflected outwardly) provides an indication to the user that the needle assembly is fully and properly installed and that sealing of the same is ensured.

Figure 69:
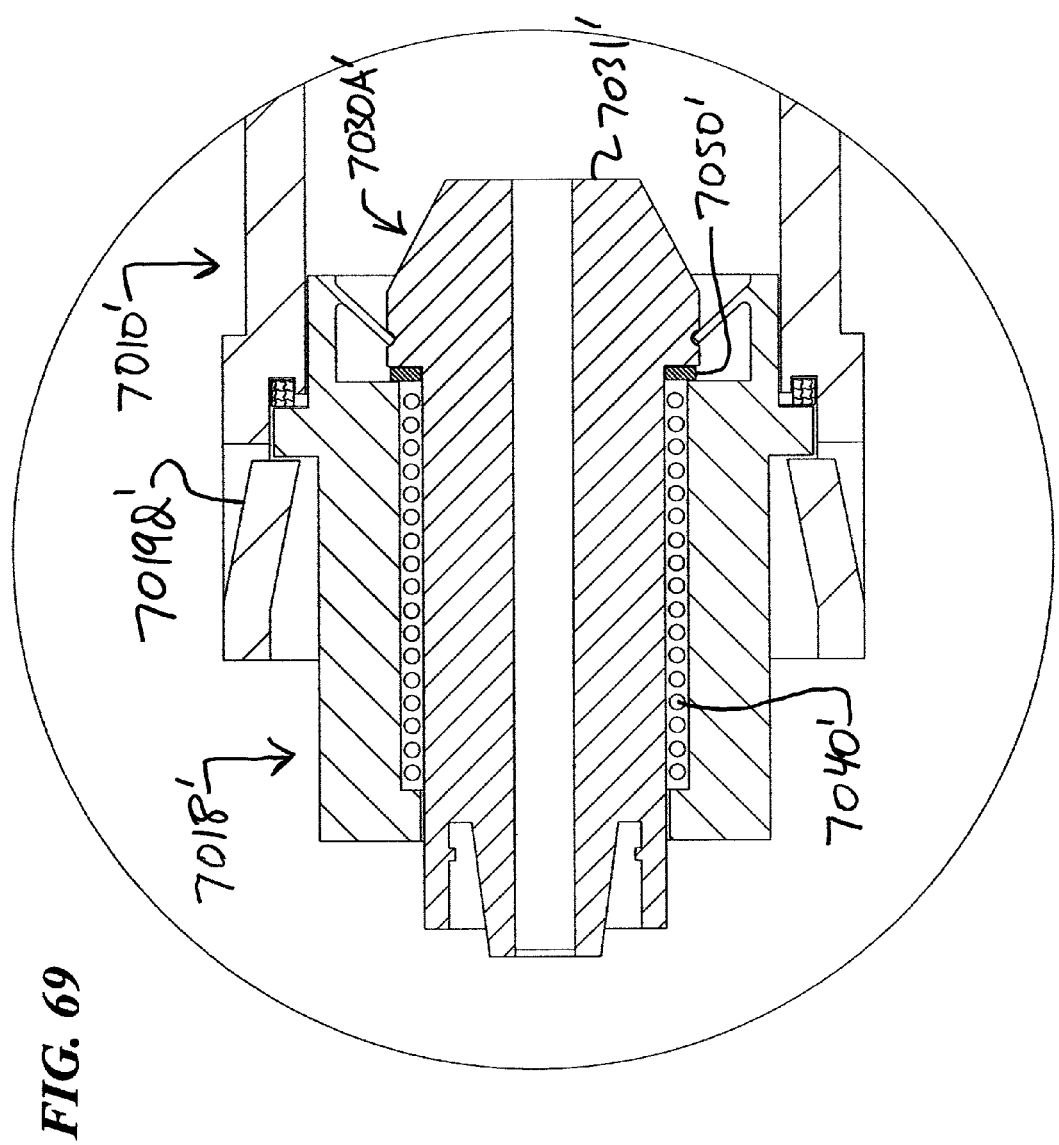
FIG. 69-73 show enlarged views of a configuration for a front portion of the injection device in accordance with other non-limiting embodiments the invention. These embodiments are similar to that of FIG. 65 with the exception of how sealing is provided between the first component and a front part of the syringe body.

FIG. 69 shows a configuration for a front portion of the injection device in accordance with another non-limiting embodiment the invention. This embodiment is similar to that of FIG. 65 with the exception of how sealing is provided between the first component 7030A' and the body 7018'. In this embodiment, a larger seal ring 7050' functions to seal a forward facing axial surface of the member 7031' to a rear-facing annular surface of the body 7018'. A spring 7040' biases the member 7031' towards a retracted position. The needle assembly body 7018' is axially and sealingly retained on the barrel 7010' via members 7019d'.

Figure 70:
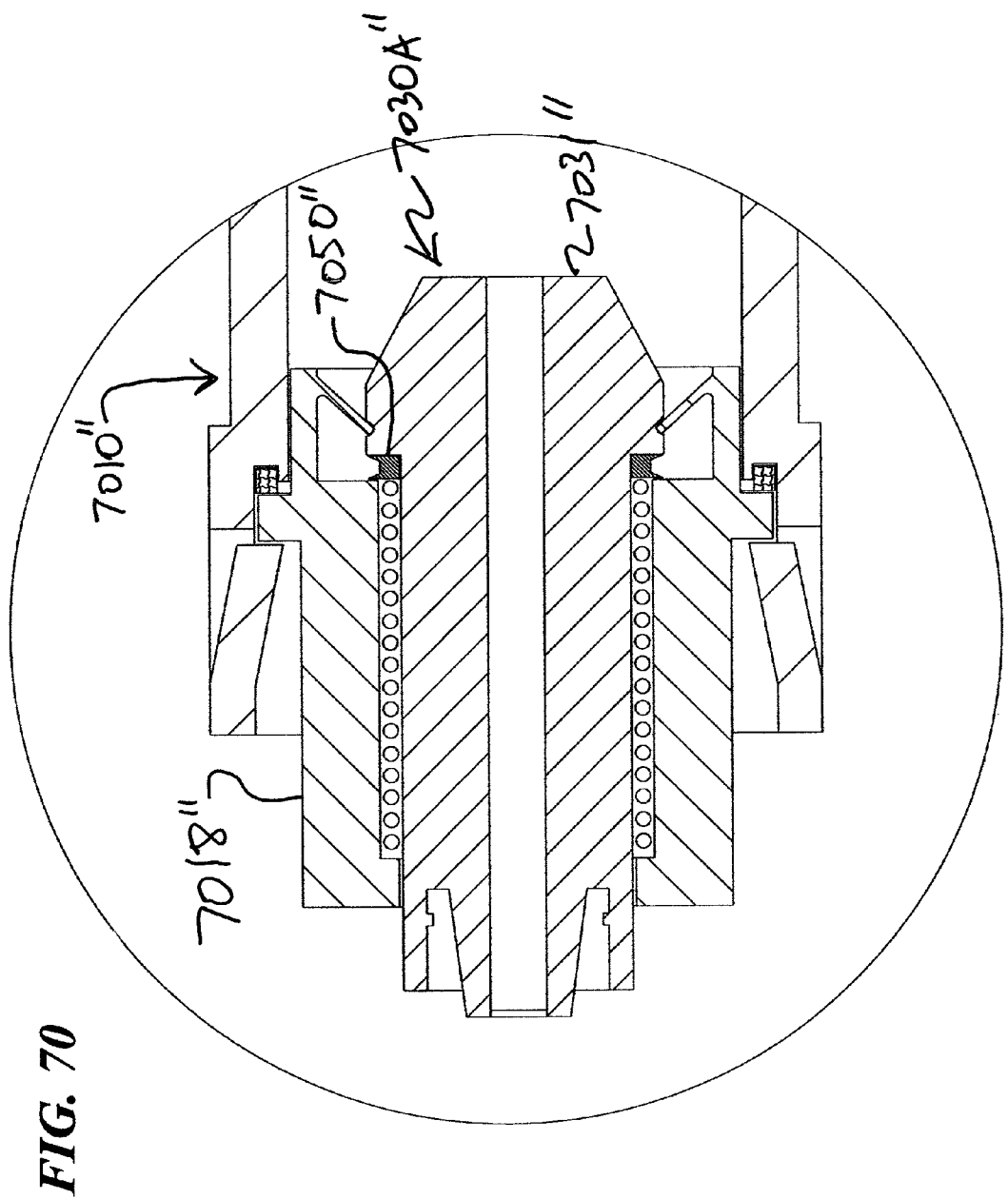

FIG. 70 shows a configuration for a front portion of the injection device in accordance with another non-limiting embodiment the invention. This embodiment is similar to that of FIG. 69 with the exception of how sealing is provided between the first component 7030A" and the body 7018". In this embodiment, a pressure activated seal ring 7050" functions to seal a forward facing axial surface of the member 7031" to a rear-facing annular surface of the body 7018".

Figure 71:
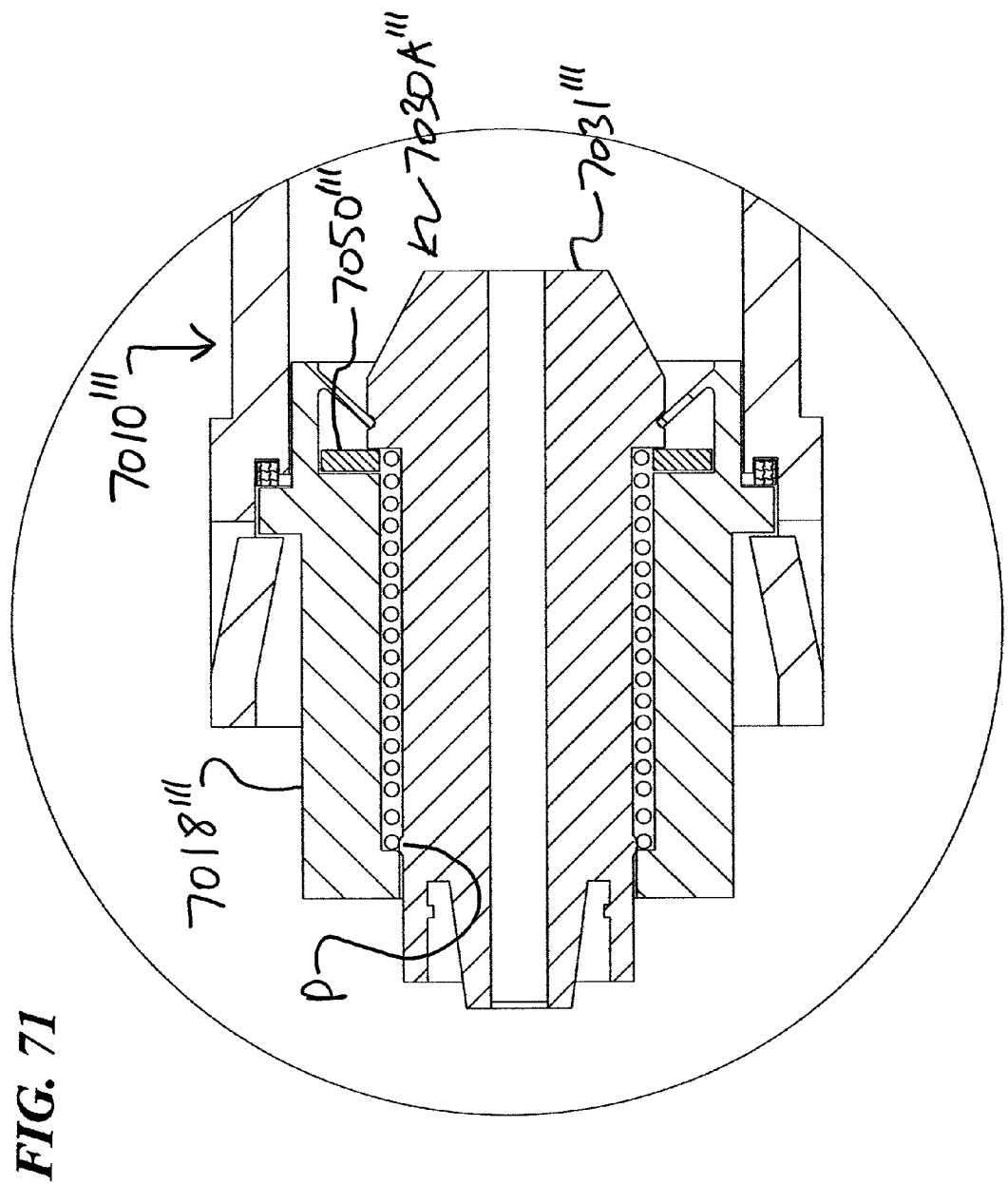

FIG. 71 shows a configuration for a front portion of the injection device in accordance with another non-limiting embodiment the invention. This embodiment is similar to that of FIG. 69 with the exception of how sealing is provided between the first component 7030A''' and the body 7018'. In this embodiment, a larger seal ring 7050'' functions to seal a forward facing axial surface of the member 7031''' to a rear-facing annular surface of the body 7018''. Additional sealing is provided by a circumferential projection P.

Figure 72:
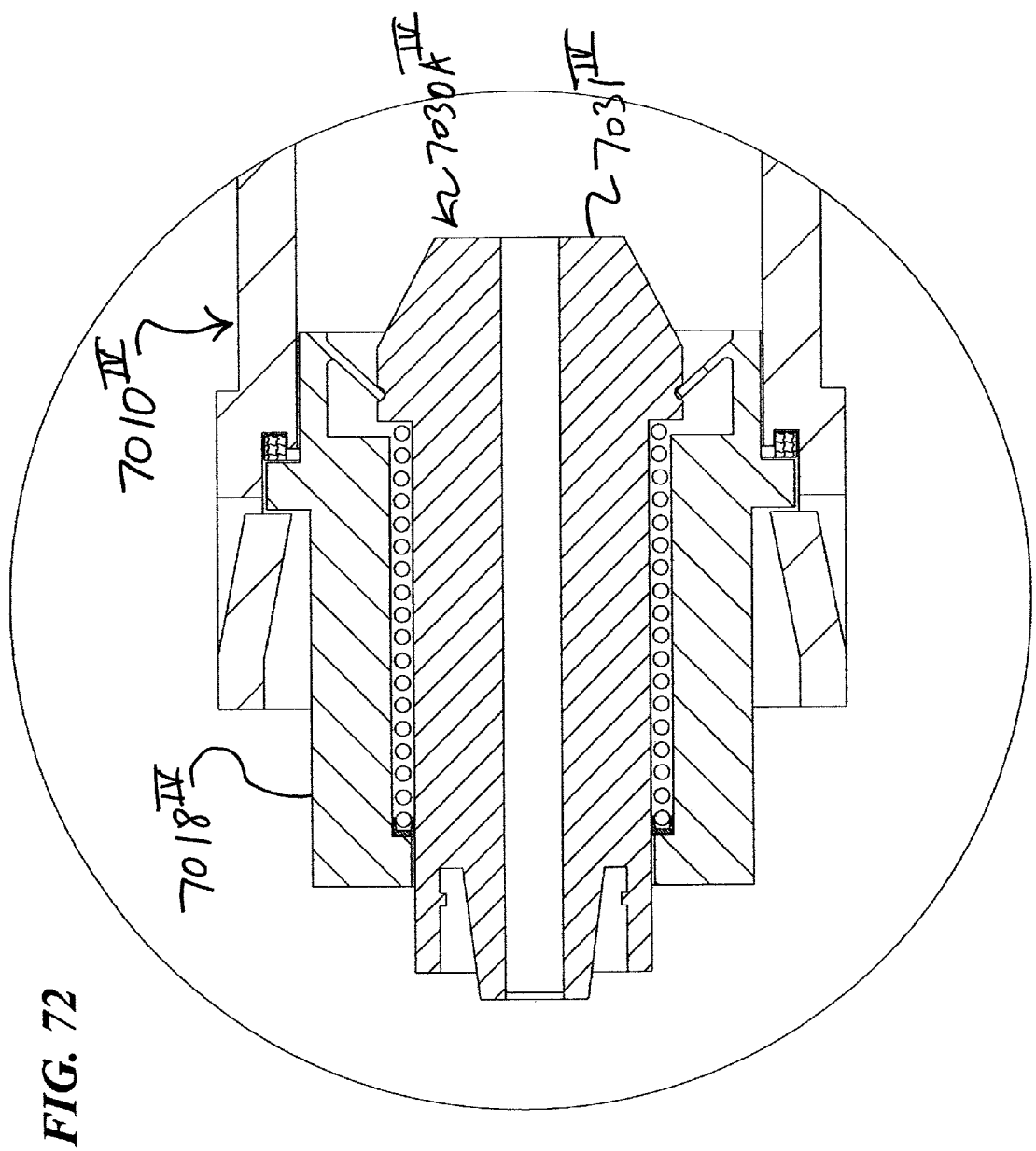
Figure 73:
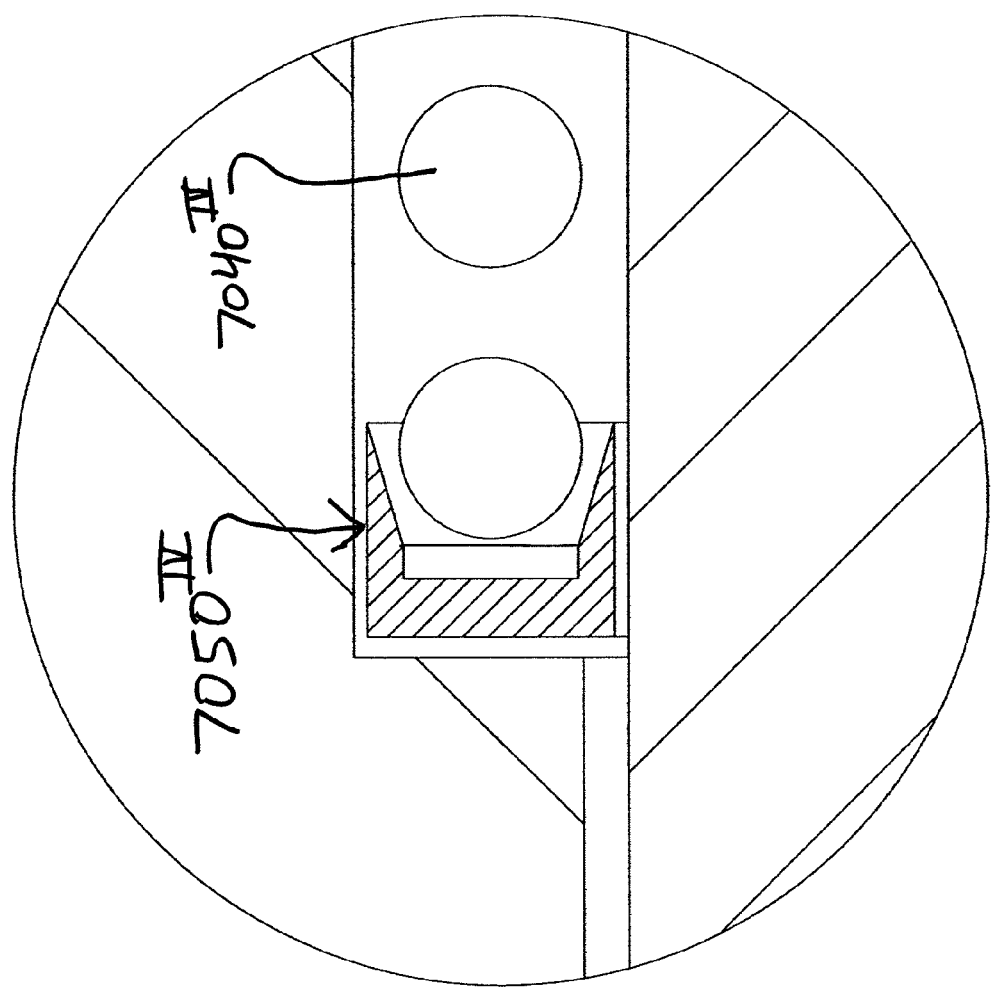

FIGS. 72 and 73 show a configuration for a front portion of the injection device in accordance with another non-limiting embodiment the invention. This embodiment is similar to that of FIG. 69 with the exception of how sealing is provided between the first component $7030A^{IV}$ and the body $7018^{IV}$. In this embodiment, a seal ring $7050^{IV}$ functions to seal an outer circumferential surface of the member $7031^{IV}$ to a rear-facing annular surface of the body $7018^{IV}$. The seal ring $7050^{IV}$ is maintained in sealing position by the spring $7040^{IV}$.

Figure 74:
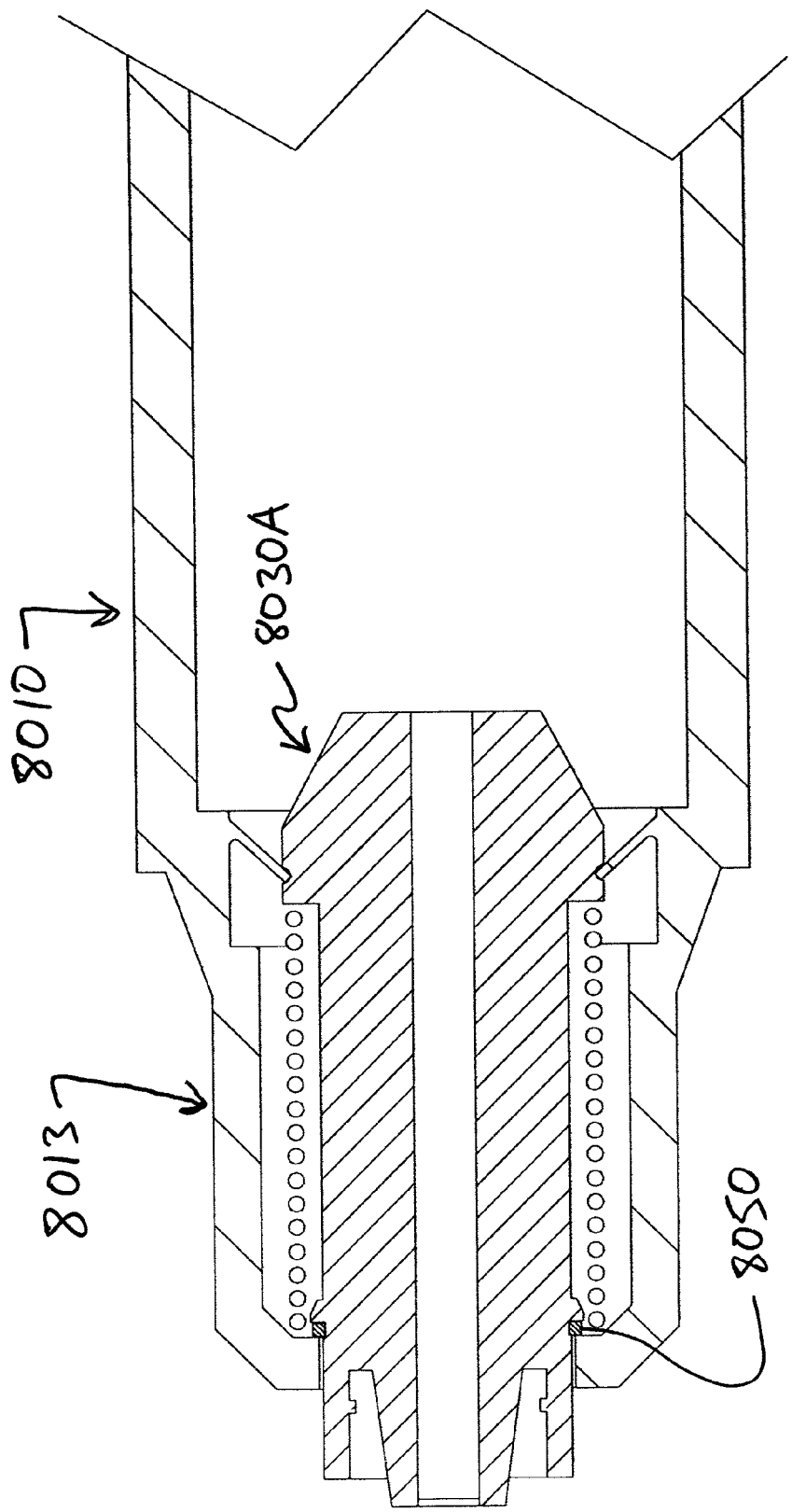
FIG. 74 shows an enlarged view of a configuration for a front portion of the injection device in accordance with another non-limiting embodiment the invention. This embodiment is similar to that of FIG. 1 except that first and second components are utilized as in the embodiment of FIG. 65 and different sealing is provided between the first component and a front part of the syringe body.
Figure 75:
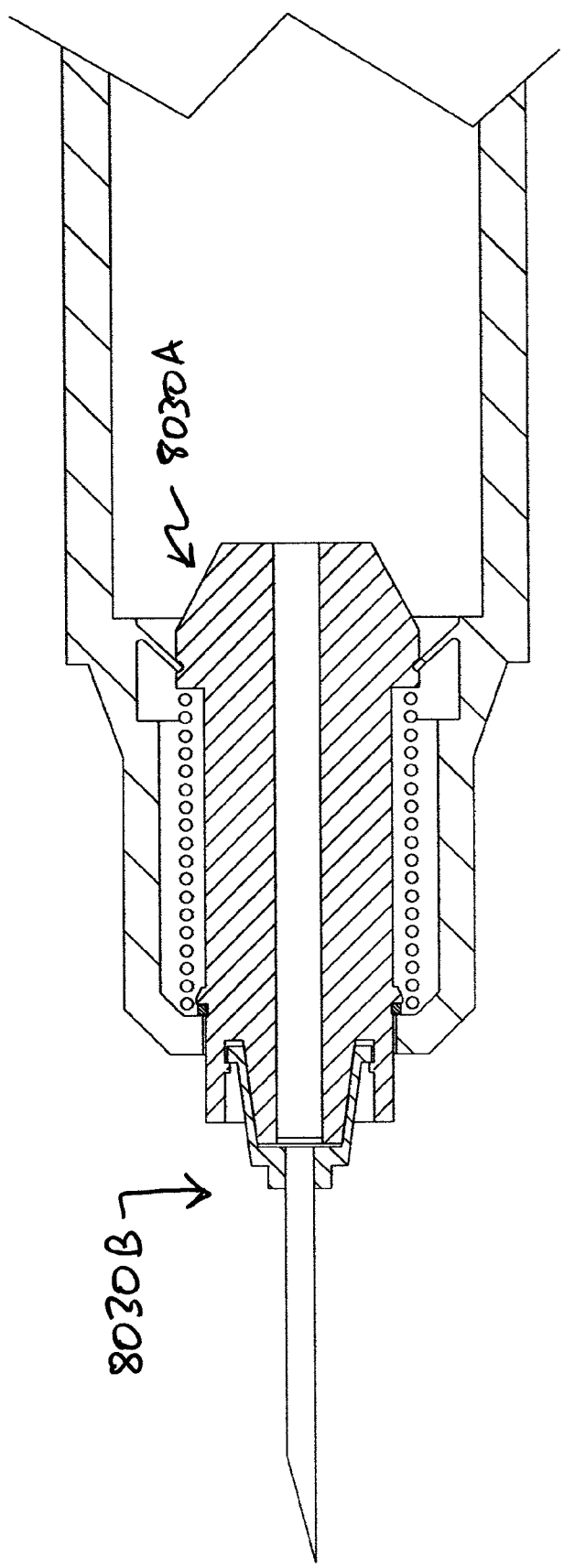
FIG. 75 shows the embodiment of FIG. 74 with the second component connected to the first component. The syringe is now in a ready to use configuration.
Figure 76:
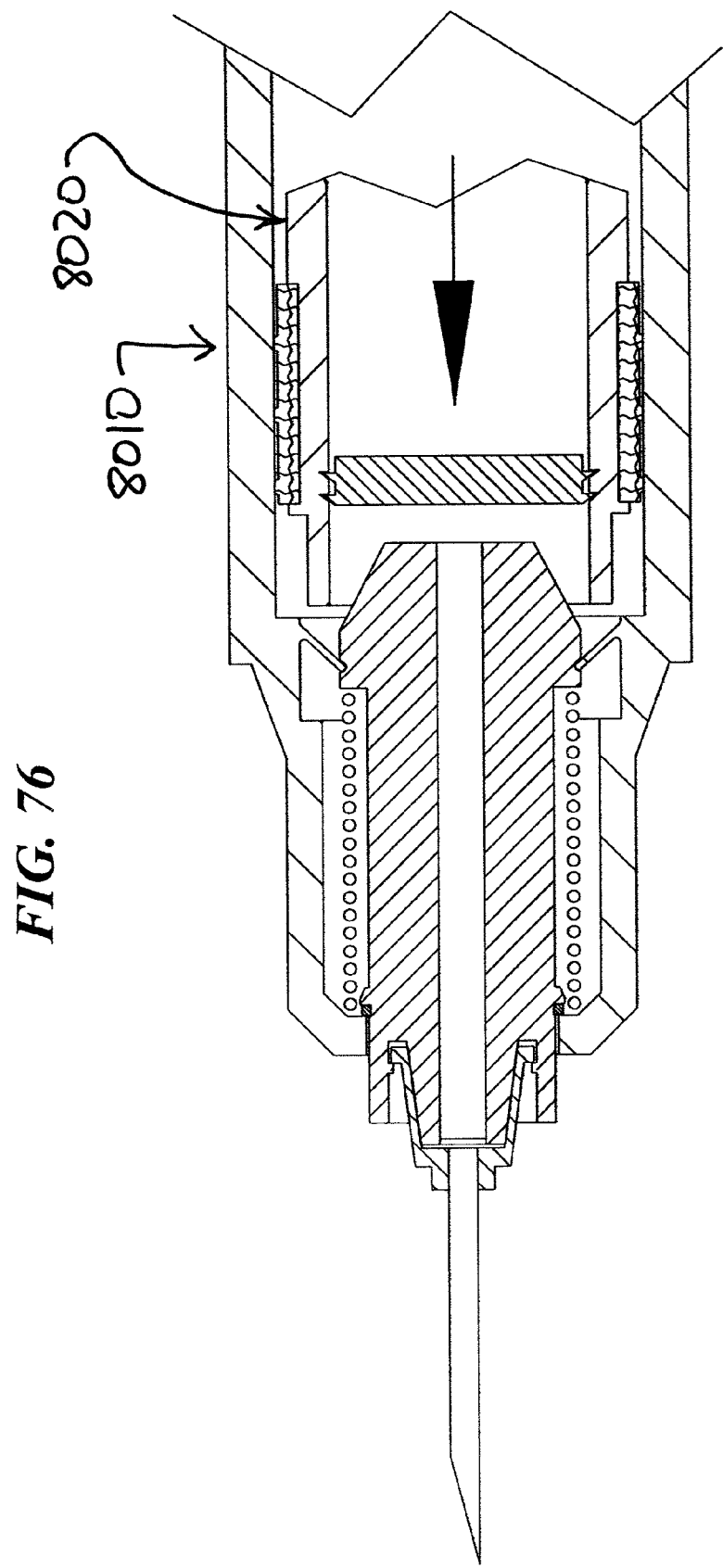
FIG. 76 shows the embodiment of FIG. 74 as the plunger is being moved toward the fully depressed position.

FIGS. 74-76 show a configuration for a front portion of the injection device in accordance with another non-limiting embodiment the invention. This embodiment is similar to that of FIG. 1 except that first and second components are utilized as in the embodiment of FIG. 65. Additionally, different sealing, i.e., seal ring 8050, is provided between the first component 8030A and the integrally formed front part 8013 of the syringe body 8010. The arrangement of FIG. 74 provides for a quick or easy connection between the needle assembly 8030B and the syringe/plunger assembly and also allows different size or types of needle members 8030B having a common interface to be connected to the first component 8030A of the syringe so that both the components 8030A/8030B can retract into the plunger 8020.

Figure 77:
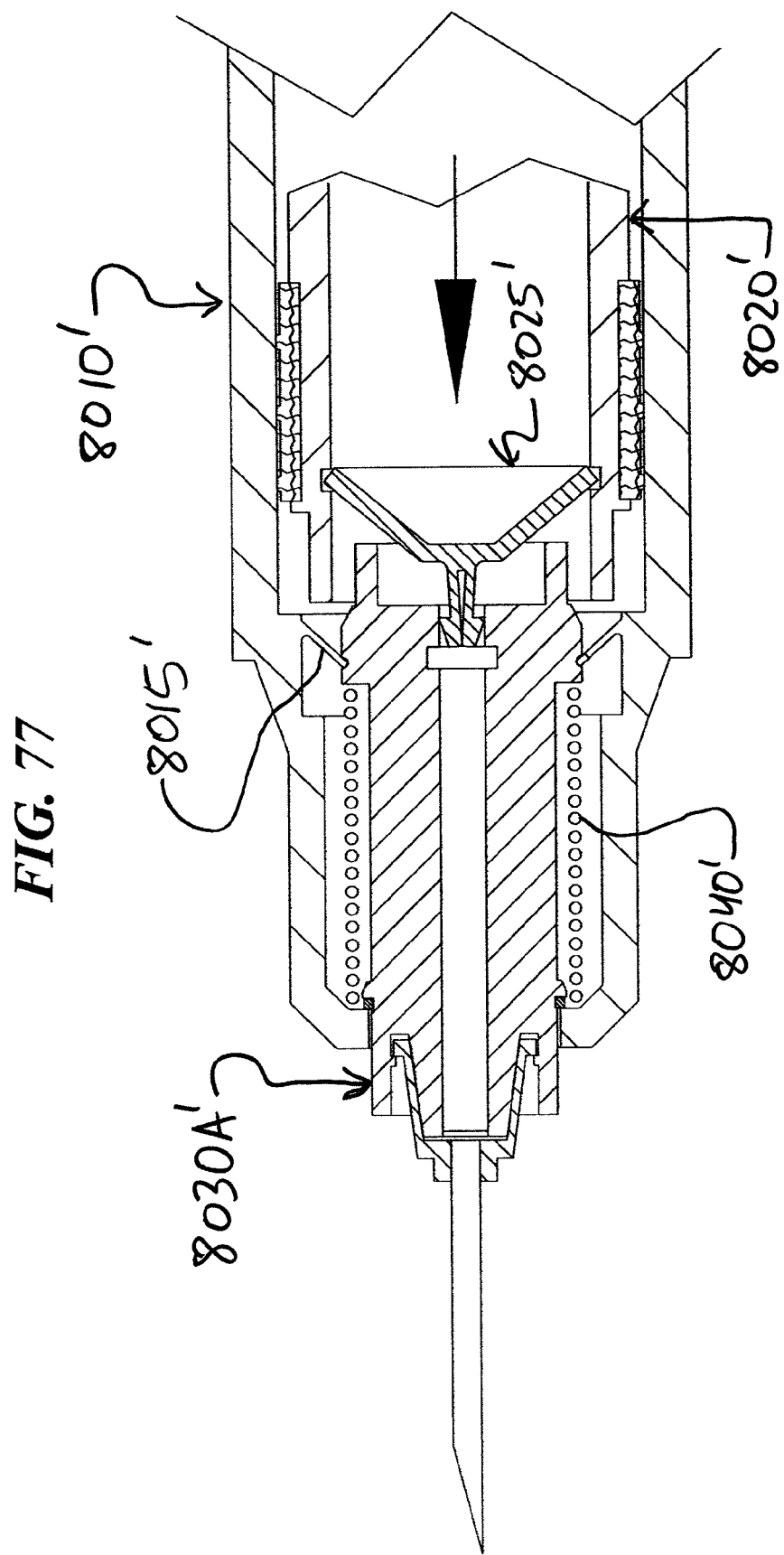
FIG. 77 shows an enlarged view of a configuration for a front portion of the injection device in accordance with another non-limiting embodiment the invention. This embodiment is similar to that of FIG. 74 except that a lockable separable plunger seal is utilized which can lock to the first component.
Figure 78:
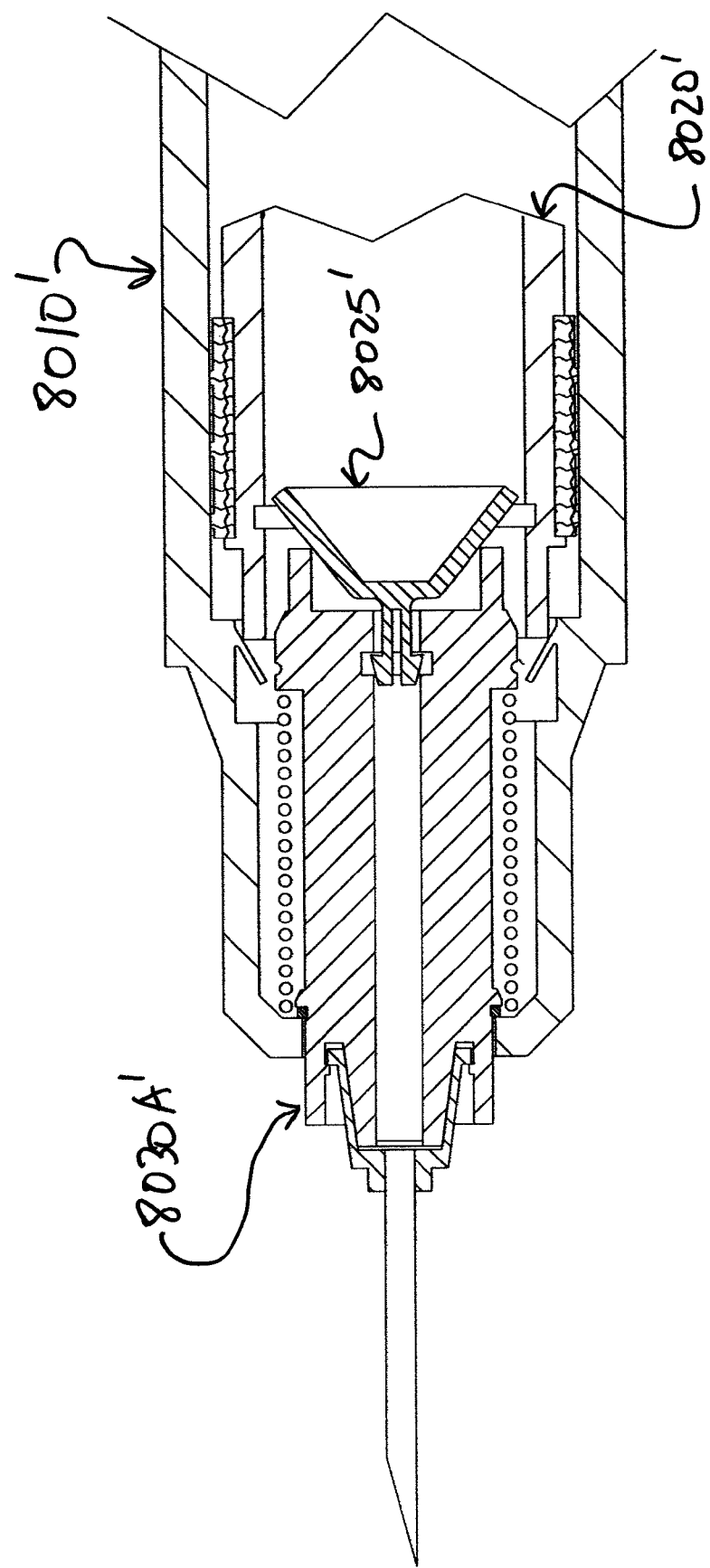
FIG. 78 shows the embodiment of FIG. 77 with the plunger in the nearly fully depressed position and shows the lockable separable plunger seal locked to the first component.

FIGS. 77 and 78 show a front portion of the injection device in accordance with another non-limiting embodiment the invention. This embodiment is similar to that of FIG. 74 except that a lockable separable plunger seal 8025' is utilized which can lock to the first component 8030A'. The arrangement of FIGS. 77 and 78 provides for a quick or easy connection between a needle assembly (shot shown in FIGS. 77 and 78) and the syringe/plunger assembly and also allows different size or types of needle members having a common interface to be connected to the first component 8030A' of the syringe so that both the components 8030A' (with the needle member mated thereto) can retract into the plunger 8020' when the plunger 8020' is fully depressed. As can be appreciated from a review of FIGS. 77 and 78, as the plunger 8020' moves toward the fully depressed position, a forward projecting end of the seal 8025' enters into an opening formed in member 8030A' as shown in FIG. 77. This movement continues until the projecting end locks into the member 8030A'. Simultaneously, a rear-facing annular projecting flange of the member 8030A' engages with the seal 8025' and causes it to deflect radially inwardly and thereby becomes unsealed (or breaks the sealing engagement) with the plunger 8020' as shown in FIG. 78. During this movement, the forward end of the plunger 8020' also causes deflection or disengagement of the members 8015' retaining the member 8030A'. As this point, nothing remains to prevent the spring 8040' from causing the member 8030A' (with the needle member attached to a front end thereof and the seal 8025' locked to a rear end thereof) to retract into the plunger 8020'.

Figure 79:
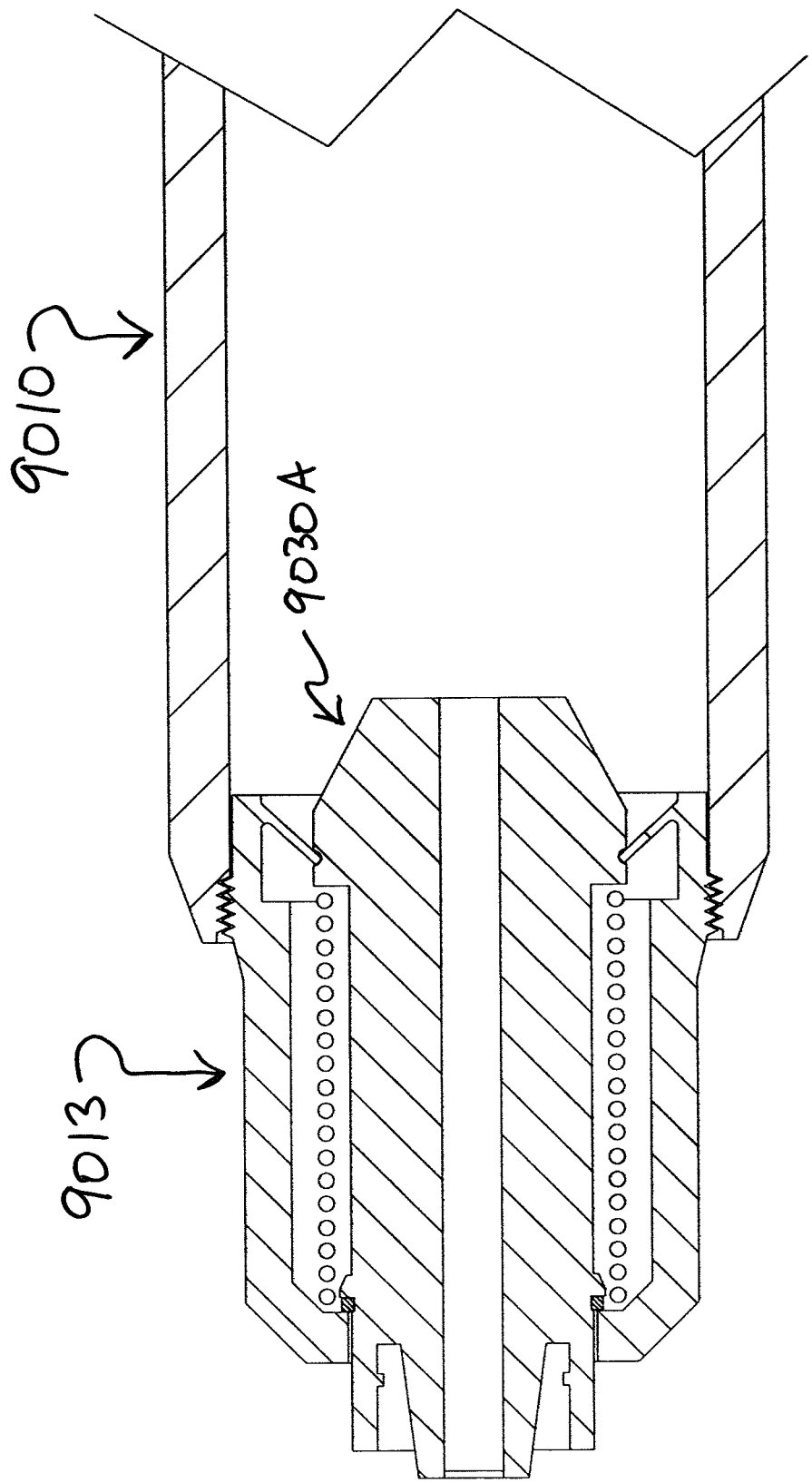
FIG. 79 shows an enlarged view of a configuration for a front portion of the injection device in accordance with another non-limiting embodiment the invention. This embodiment is similar to that of FIG. 74 except that the front portion of the syringe is threadably connected to a front end of the syringe main body.

FIGS. 79 and 80 show a front portion of the injection device in accordance with another non-limiting embodiment the invention. This embodiment is similar to that of FIG. 74 except that the front portion 9013 of the syringe is threadably connected to a front end of the syringe main body 9010. The member 9030A which contains a standard interface is mounted to the front portion 9013. As shown in FIG. 80, external threads ET of the front portion 9013 are configured to threadably engage with internal threads IT of the body 9010. This system or arrangement has at least two advantageous. First, it allows for easier installation of the member 9030A. It also allows a user to attach different types of front sections 9013 onto a common syringe body 9010.

Figure 81:
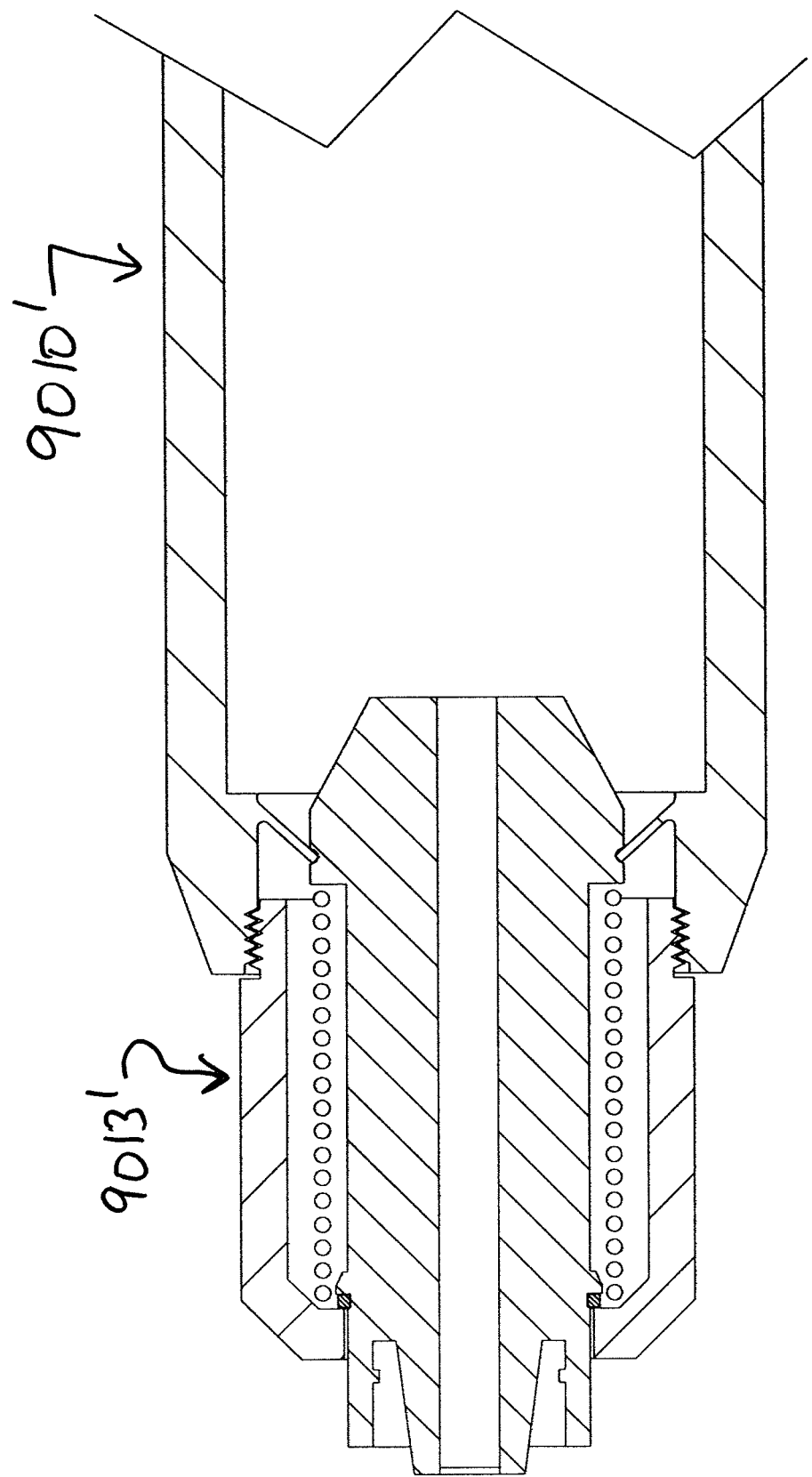
FIG. 81 shows an enlarged view of a configuration for a front portion of the injection device in accordance with another non-limiting embodiment the invention. This embodiment is similar to that of FIG. 79 except that the front portion of the syringe is differently threadably connected to a front end of the syringe main body.
Figure 82:
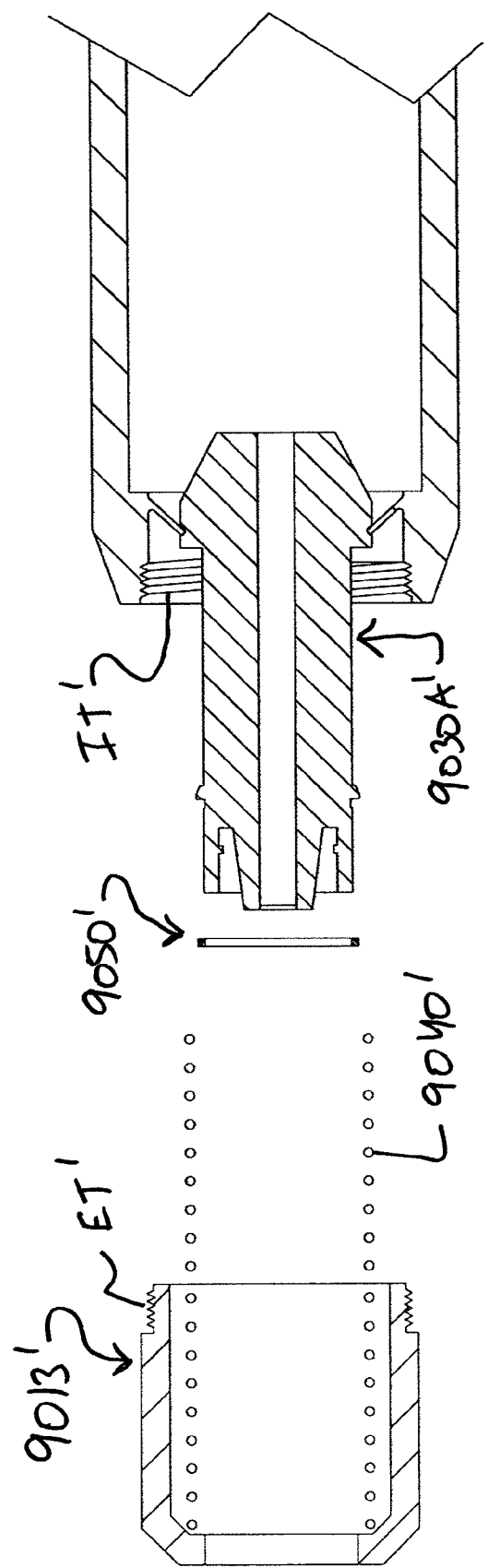
FIG. 82 shows the embodiment of FIG. 81 with various parts thereof being shown in a unconnected/unassembled state.

FIGS. 81 and 82 show a front portion of the injection device in accordance with another non-limiting embodiment the invention. This embodiment is similar to that of FIG. 79 except that it is differently threadably connected to a front end of the syringe main body. The front portion 9013' of the syringe is threadably connected to a front end of the syringe main body 9010'. The member 9030A' which contains a standard interface is however mounted to the front end of the body 9010'. As shown in FIG. 82, external threads ET' of the front portion 9013' are configured to threadably engage with internal threads IT' of the body 9010'. This system or arrangement has at least one advantageous. It allows for easier installation of the member 9030A' during assembly of the syringe. As in the previous embodiment, this embodiment utilizes a spring 9040' and a seal 9050'.

Figure 65:
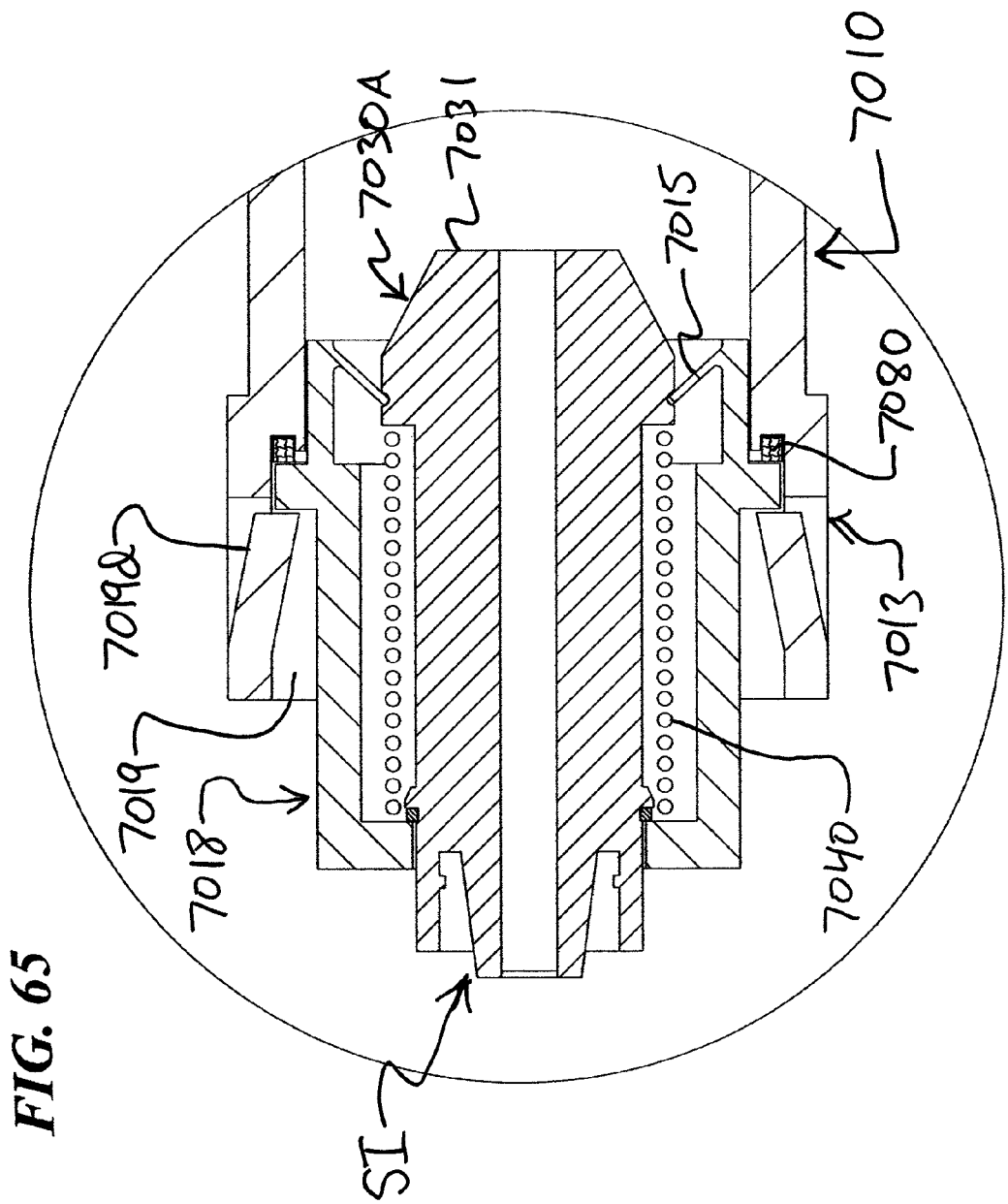
FIG. 65 shows an enlarged view of a configuration for a front portion of the injection device in accordance with another non-limiting embodiment the invention. This embodiment is similar to that of FIG. 52 except that the needle unit is separated into two main components. A first component or assembly utilizes a needle hub portion which is axially retained in a front section of the syringe and has a standard receiving interface. A second component or assembly utilizes a needle and a standard interface hub which can be sealingly connected to the standard receiving interface of the first component.
Figure 67:
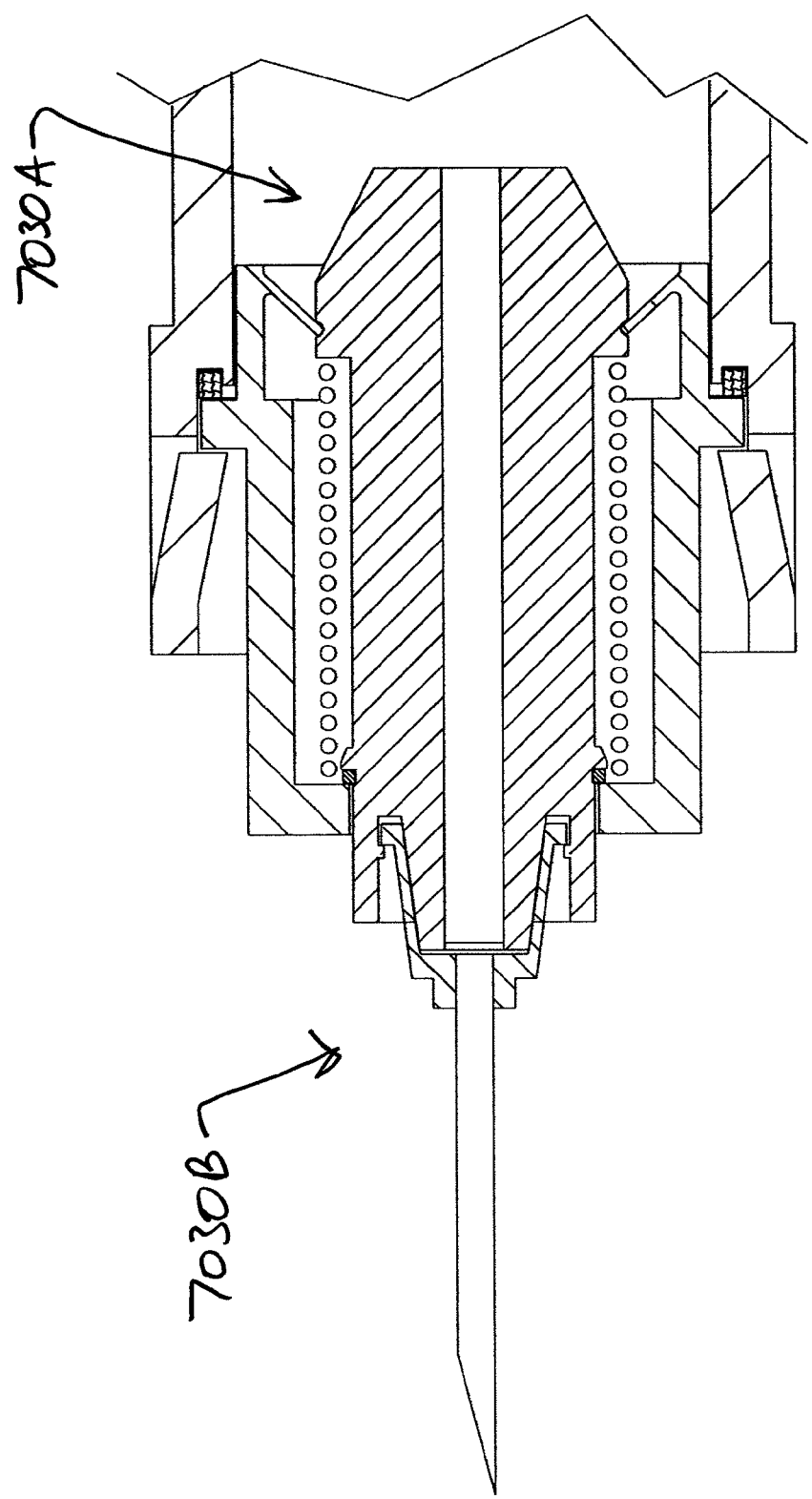
FIG. 67 shows the embodiment of FIG. 65 with the second component connected to the first component. The syringe is now in a ready to use configuration.
Figure 68:
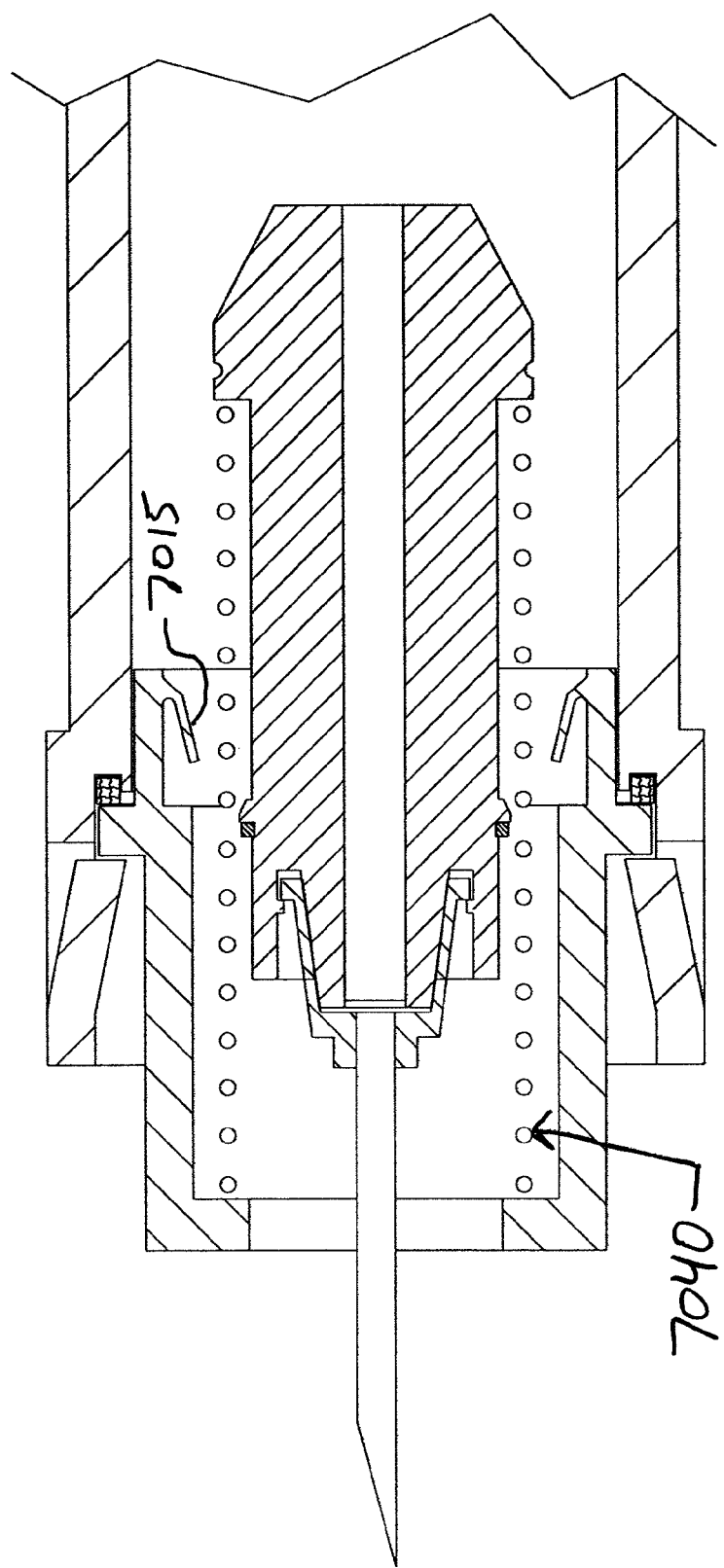
FIG. 68 shows the embodiment of FIG. 67 after the plunger (not shown) has been fully depressed and shows how the connected first and second components can automatically retract into the syringe by the spring.

FIG. 84 shows one way in which a user can mount a front portion, e.g., the embodiment of FIG. 65, on a syringe. According to this embodiment, the user can remove a safety cover NHA' and install a needle member (similar to that shown installed in FIG. 84) in the manner shown in FIG. 67. The safety cover NHA' is used to maintain the interface in a sterile condition until the front portion is installed on the syringe body. To use the syringe shown in FIG. 84, a user removes the safety cover NHA', installs a needle member, and depresses the plunger of the syringe during injection. Once fully depressed, the syringe is rendered un-usable and the needle member remains safely disposed in the plunger.

FIG. 85 shows another way in which a user can mount a front portion of on a syringe. According to this embodiment, the syringe is packaged with a needle member already installed on the standard interface and maintained in a sterile condition by the safety cover NHA'. The user can install the front portion on the syringe body and then remove the safety cover NHA' and use the syringe.

The devices described herein can also utilize one or more features disclosed in prior art documents expressly incorporated by reference in pending U.S. patent application Ser. No. 11/616,196 (Publication No. 2008/0154212). This application and the documents expressly incorporated therein is hereby expressly incorporated by reference in the instant application. Furthermore, one or more of the various parts of the device can preferably be made as one-piece structures by e.g., injection molding, when doing so reduces costs of manufacture. Non-limiting materials for most of the parts include synthetic resins such as those approved for syringes, blood collection devices, or other medical devices. Furthermore, the invention also contemplates that any or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A single-use injection device comprising:
    a barrel;
    a plunger having a portion structured and arranged to move within the barrel and a frangible member arranged within the plunger at a location that is axially spaced from a proximal end of the plunger;
    a needle connecting arrangement that comprises a needle connecting interface adapted to mate with a needle interface, a biasing member, and a body; and
    said body one of:
        containing at least one deflectable member movable between an initial position and a position allowing the needle connecting interface to retract into the barrel under action of the biasing member;
        being capable of being installed on the barrel by a user prior to use; and
        being capable of being non-removably connected with the barrel by a user.

2. The injection device of claim 1, wherein the plunger is a hollow plunger.

3. The injection device of claim 1, wherein the plunger comprises a piston arranged at a proximal area of the plunger and an actuating end arranged in front of the piston.

4. The injection device of claim 3, wherein the plunger further comprises at least one of:
    the piston being an elastomer or rubber piston;
    a hollow space sized and configured to receive therein an injection needle; and
    a locking member adapted to lock with a locking member arranged on the barrel.

5. The injection device of claim 1, wherein the barrel and the plunger each comprise a synthetic resin material.

6. The injection device of claim 1, wherein the at least one deflectable member of the body comprises at least one releasable retaining member.

7. The injection device of claim 6, wherein the at least one releasable retaining member comprises plural radially oriented releasable retaining members.

8. The injection device of claim 1, wherein the at least one deflectable member of the body comprises at least one deflectable retaining member.

9. The injection device of claim 8, wherein the at least one deflectable retaining member comprises plural radially oriented releasable retaining members.

10. The injection device of claim 1, further comprising at least one of:
    a locking arrangement that is structured and arranged to lock a portion of the needle connecting arrangement to a portion of the plunger;
    a locking arrangement selectively locking a portion of the plunger to the barrel upon the plunger reaching a substantially fully depressed position.

11. The injection device of claim 1, wherein, when the plunger is moved to a full injection position, a member arranged within the needle connecting arrangement and coupled to the needle connecting interface is automatically caused to retract into the plunger.

12. The injection device of claim 1, wherein, when the plunger is moved to a full injection position, a member arranged within the needle connecting arrangement is automatically caused to retract into the barrel.

13. The injection device of claim 1, further comprising a system providing an indication to the user in regards to a depressed position of the plunger.

14. The injection device of claim 1, further comprising a system providing an indication to the user that at least one of:
    the plunger has reached a full injection position; and
    the further forward movement of the plunger will cause a member coupled to a needle to automatically retract into the plunger.

15. A method of using the injection device of claim 1, the method comprising:
    installing a needle member having a needle and a connecting interface on the injection device; and
    moving the plunger relative to the barrel so as to cause medicine to exit through the needle,
    wherein the needle member is capable of retracting into the plunger.

* * * * *